Figure 3:
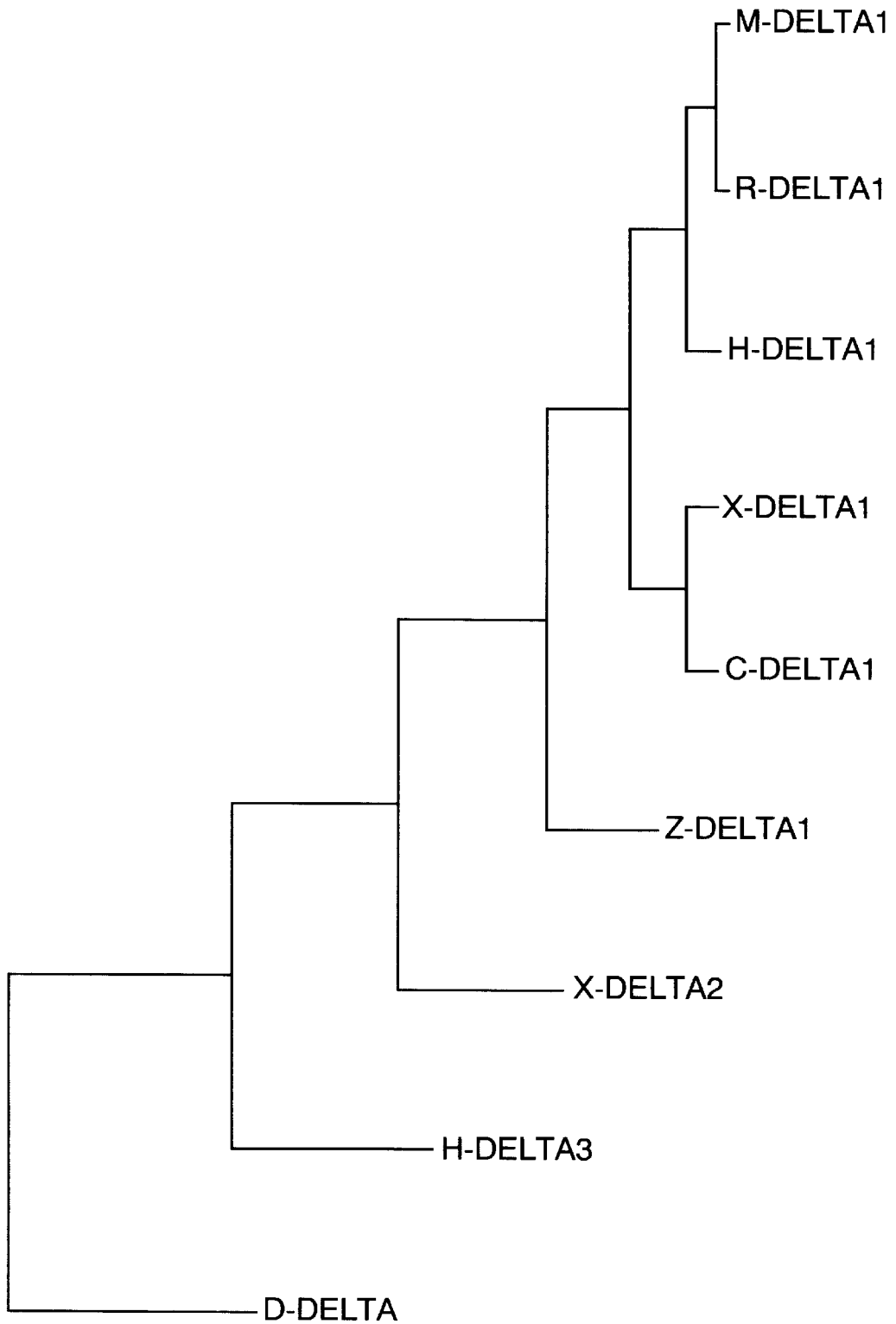

United States Patent [19]
McCarthy et al.

[11] Patent Number: 6,121,045
[45] Date of Patent: Sep. 19, 2000

[54] HUMAN DELTA3 NUCLEIC ACID MOLECULES

[75] Inventors: Sean Anthony McCarthy, Boston; David Paul Gearing, Wellesley, both of Mass.

[73] Assignee: Millennium Biotherapeutics, Inc., Cambridge, Mass.

[21] Appl. No.: 08/872,855

[22] Filed: Jun. 11, 1997

Related U.S. Application Data

[63] Continuation-in-part of application No. 08/832,633, Apr. 4, 1997, abandoned.
[51] Int. Cl.$^7$ .......................... C07H 21/04; C12N 15/63; C12N 15/85
[52] U.S. Cl. .................. 435/325; 435/320.1; 435/252.3; 435/254.11; 536/23.5
[58] Field of Search .................................. 435/70.1, 243, 435/252.3, 325, 320.1, 6, 254.11; 536/23.1, 23.5, 24.3, 24.31, 24.33, 235

[56] References Cited

U.S. PATENT DOCUMENTS

| | | |
|---|---|---|
| 5,580,738 | 12/1996 | Laborda . |
| 5,644,031 | 7/1997 | Laborda . |
| 5,648,464 | 7/1997 | Artavanis-Tsakonas et al. . |
| 5,780,300 | 7/1998 | Artavanis-Tsakonas et al. . |

FOREIGN PATENT DOCUMENTS

| | | |
|---|---|---|
| WO 92/19734 | 11/1992 | WIPO . |
| WO 94/07474 | 4/1994 | WIPO . |
| WO 96/34099 | 10/1996 | WIPO . |
| WO 97/01571 | 1/1997 | WIPO . |
| WO 97/11956 | 4/1997 | WIPO . |
| WO97/19172 | 5/1997 | WIPO . |

OTHER PUBLICATIONS

GenBank Accession Nos. U26590, Aug. 9, 1995, Henrique et al.
GenBank Accession No. U70843, Dec. 1, 1996, Chitins et al.
GenBank Accession No. AA 142228, Jan. 13, 1997, Hillier et al.
GenBank Accession No. T33770, Jan. 5, 1995, Hillier et al.
GenBank Accession No. T33811, Jan. 5, 1995, Hillier et al.
GenBank Accession No. T07963, Sep. 2, 1993, Hillier et al.
GenBank Accession No. R32717, Apr. 30, 1995, Hillier et al.
GenBank Accession No. T07962, Sep. 2, 1993, Hillier et al.
GenBank Accession No. X8903, Sep. 29, 1995, Bettenhausen et al.
GenBank Accession No. U26590, Aug. 9, 1995, Hillier et al.
GenBank Accession No. L42229, Jul. 17, 1995, Hillier et al.
GenBank Accession No. U78889, Dec. 3, 1996, Hillier et al.
Rudinger Jim "Peptide Hormones", Parsons, J.A. ed, University Park Press, Jun. 1976 pp. 1–6.
Hertzog et al, DNA and Cell Biology, 12(6): 465–471, 1993.
Jazin et al, Regulatory Peptides, 47: 247–258, 1993.
Lebo et al, Cold Spring Harbor Symposia on Quantitative Biology vol. LI, Cold Spring Harbor Laboratory, 1986, pp. 169–176.
AA235839 Hillier et al. WashU–Merck EST Project (Mar. 6, 1997).
X63545 MacDonald et al. (Oct. 22, 1995).
Dornseifer et al. (1997) "Overexpression of a zebrafish homolog of the Drosphila neurogenic gene Delta perturbs differentiation of primary neurons and somite development" Mech. Dev. 63:159.
Kopcynski et al. (1988) "Delta, a Drosophila neurogenic gene, is transcriptionally complex and encodes a protein related to blood coagulation factors and epidermal growth factor of vertebrates" Genes & De.v. 2:1723.
Henrique, D. et al. "Expression of a Delta homologue in prospective neurons in the chick" Nature 375:787–790, 1995.
Chitnis, A. et al. "Primary neurogenesis in Xenopus embryos regulated by a homologue of the Drosophila neurogenic gene Delta" Nature 375:761–766, 1995.
Bettenhausen, B. et al. "transient and restricted expression during mouse embryogenesis of DII1, a murine gene closely related to Drosophila Delta" Development 121:2407–2418, 1995.
Joutel, A. et al. "Notch3 mutations in CADASIL, a hereditary adult–onset condition causing stroke and dementia" Nature 383:707–710, 1996.
Gridley, Thomas "Notch, stroke and dementia" Nature 383:673, 1996.
Muskavitch, M.A.T. "Delta–Notch signaling and Drosophila cell fate choice" Dev. Biol. 166:415–430, 1994.
Casaubon, L.K. et al. "The Gene Responsible for a Severe Form of Peripheral Neuropathy and Agenesis of the Corpus Callosum Maps to Chromosome 15q" *Am. J. Hum. Genet.* 58:28–34, 1996.
Boehringer Mannheim Biochemicals, 1991 catalog p. 557.
American Type Culture Collection (ATCC) Catalogue of Cell Lines and Hybridomes, 7$^{th}$ edition, 1992 pp.73 & 267.

*Primary Examiner*—Patricia A. Duffy
*Attorney, Agent, or Firm*—Foley, Hoag & Eliot, LLP; Beth E. Arnold, Esq.; Isabelle M. Clauss, Ph.D.

[57] ABSTRACT

The invention provides nucleic acid molecules which encode polypeptides having homology to proteins in the Delta family of proteins. The invention also provides vectors containing nucleic acid molecules of the invention and host cells containing the vectors.

21 Claims, 9 Drawing Sheets

```
GTCGACCCACGCGTCCGGCTGCGCGCAGGCGGAACACGAGGCCAAGAGCCAGCCCCAGCCGCCTTGGTGCAGCGT      79

ACACCGGCACTAGCCCGCTTGCAGCCCCCAGGATTAGACAGAAGACGCGTCCTCGGCGGTCGCCCCAGCCGTAGTC    158

ACCTGGATTACCTACAGCGGCAGCTGCAGCGGAGCCAGCAGAGAAGGCAGAGAGCGTCCCGAGAGAGCGCCT        237

CTTTTCAGGAGACCCGCCGGCTGGCGGGACGCGCGGGAAAGCGGCGTCGCGAACAGAGCCAGATTGAGGGCCCGGGGTG 316

M   A   A   S   R   S   A   S   G   W   A   L   L         14
GAGAGAGCGACGCCCGAGGGG ATG GCG GCA GCG TCC CGG AGC GCC TCT GGC TGG GCG CTA CTG    379

L   L   V   A   L   W   Q   Q   R   A   A   G   S   G   V   F   Q   L   Q   L    34
CTG CTG GTG GCA CTT TGG CAG CAG CGC GCG GCA GGC TCC GGC GTC TTC CAG CTG CAG CTG  439

Q   E   F   I   N   E   R   G   V   L   A   S   G   R   P   C   E   P   G   C    54
CAG GAG TTC ATC AAC GAG CGC GGC GTA CTG GCC AGT GGG CGG CCT TGC GAG CCC GGC TGC  499

R   T   F   F   R   V   C   L   K   H   F   Q   A   V   V   S   P   G   P   C    74
CGG ACT TTC TTC CGC GTC TGC CTT AAG CAC TTC CAG GCG GTC GTC TCG CCC GGA CCC TGC  559

T   F   G   T   V   S   T   P   V   L   G   T   N   S   F   A   V   R   D   D    94
ACC TTC GGG ACC GTC TCC ACG CCG GTA TTG GGC ACC AAC TCC TTC GCT GTC CGG GAC GAC  619

S   S   G   G   R   N   P   L   Q   L   P   F   N   F   T   W   P   G   T   V   114
AGT AGC GGG GGC CGC AAC CCT CTC CAA CTG CCT TTC AAT TTC ACC TGG CCG GGT ACC      679
```

FIG. 1A

```
F   S   L   I   I   E   A   W   H   A   P   G   D   D   L   R   P   E   A   L       134
TTC TCG CTC ATC ATC GAA GCT TGG CAC GCG CCA GGA GAC GAC CTG CGG CCA GAG GCC TTG      739

P   P   D   A   L   I   S   K   I   A   I   Q   G   S   L   A   V   G   Q   N       154
CCA CCA GAT GCA CTC ATC AGC AAG ATC GCC ATC CAG GGC TCC CTA GCT GTG GGT CAG AAC      799

W   L   D   E   Q   T   S   T   L   T   R   L   R   Y   S   Y   R │ V   I │         174
TGG TTA GAT GAG CAA ACC AGC ACC CTC ACA AGG CTG CGC TAC TCT TAC CGG │GTC ATC│        859
                                        DSL

C   S   D   N   Y   Y   G   D   N   C   S   R   L   C   K   K   R   N   D   H       194
TGC AGT GAC AAC TAC TAT GGA GAC AAC TGC TCC CGC CTG TGC AAG AAG CGC AAT GAC CAC      919

F   G   H   Y   V   C   Q   P   D   G   N   L   S   C   L   P   G   W   T   G       214
TTC GGC CAC TAT GTG TGC CAG CCA GAT GGC AAC TTG TCC TGC CTG CCC GGT TGG ACT GGG      979
                                                    I

│E   Y   C │ Q   Q   P   I │ C   L   S   G   C   H   E   Q   N   G   Y   C   S       234
│GAA TAT TGC│CAA CAG CCT ATC│TGT CTT TCG GGC TGT CAT GAA CAG AAT GGC TAC TGC AGC     1039
                                                                              II

K   P   A   E   C   L   C   R   P   G   W   Q   G   R   L   C │ N   E   C   I │     254
AAG CCA GCA GAG TGC CTC TGC CGC CCA GGC TGG CAG GGC CGG CTG TGT│AAC GAA TGC ATC│    1099

P   H   N   G   C   R   H   G   T   C   S   T   P   W   Q   C   T   C   D   E       274
CCC CAC AAT GGC TGT CGC CAC GGC ACC TGC AGC ACT CCC TGG CAA TGT ACT TGT GAT GAG     1159
```

FIG. 1B

| | | | | | | | | | | |
|---|---|---|---|---|---|---|---|---|---|---|
| G | W | G | G | L | F | C | D | Q | D | L | N | Y | C | T | H | H | S | P | C | 294 |
| GGC | TGG | GGA | GGC | CTG | TTT | TGT | GAC | CAA | GAT | CTC | AAC | TAC | TGC | ACC | CAC | CAC | TCC | CCA | TGC | 1219 |

III

| K | N | G | A | T | C | S | N | S | G | Q | R | S | Y | T | C | T | C | R | P | 314 |
| AAG | AAT | GGG | GCA | ACG | TGC | TCC | AAC | AGT | GGG | CAG | CGA | AGC | TAC | ACC | TGC | ACC | TGT | CGC | CCA | 1279 |

| G | Y | T | G | V | D | C | E | L | S | E | C | D | S | N | P | C | R | 334 |
| GGC | TAC | ACT | GGT | GTG | GAC | TGT | GAG | CTC | AGC | GAG | TGT | GAC | AGC | AAC | CCC | TGT | CGC | 1339 |

IV

| N | G | G | S | C | K | D | Q | E | D | G | Y | H | C | L | C | P | P | G | Y | 354 |
| AAT | GGA | GGC | AGC | TGT | AAG | GAC | CAG | GAG | GAT | GGC | TAC | CAC | TGC | CTG | TGT | CCT | CCG | GGC | TAC | 1399 |

| Y | G | L | H | C | E | H | S | T | L | S | C | A | D | S | P | C | F | N | G | 374 |
| TAT | GGC | CTG | CAT | TGT | GAA | CAC | AGC | ACC | TTG | AGC | TGC | GCC | GAC | TCC | CCC | TGC | TTC | AAT | GGG | 1459 |

V

| G | S | C | R | E | R | N | Q | C | E | K | K | V | D | R | C | T | S | N | P | 394 |
| GGC | TCC | TGC | CGG | GAG | CGC | AAC | CAG | TGC | GAG | AAG | AAA | GTG | GAC | AGG | TGC | ACC | AGC | AAC | CCC | 1519 |

| C | P | P | N | F | 414 |
| T | G | S | N | C | T | E | C | P | P | N | F | 414 |
| ACC | GGC | TCC | AAC | TGC | ACC | GAG | TGT | CCC | CCC | AAC | TTC | 1579 |

VI

| G | Q | C | L | N | R | G | P | S | R | M | C | R | C | A | N | G | 434 |
| GGA | CAG | TGC | CTG | AAC | CGA | GGT | CCA | AGC | CGC | ATG | TGC | CGC | TGT | GCC | AAC | GGG | 1639 |

| P | G | F | T | G |
| CCT | GGA | TTC | ACG | GGC |

FIG. 1C

|     |     |     |     |     |     |     |     |     |     | VII |     |     |     |     |     |     |     |     |     |      |
|-----|-----|-----|-----|-----|-----|-----|-----|-----|-----|-----|-----|-----|-----|-----|-----|-----|-----|-----|-----|------|
| T   | Y   | C   | E   | L   | H   | V   | S   | D   | C   | A   | R   | N   | P   | C   | A   | H   | G   | G   | T   | 454  |
| ACC | TAC | TGT | GAA | CTC | CAC | GTC | AGC | GAC | TGT | GCC | CGT | AAC | CCT | TGC | GCC | CAC | GGT | GGC | ACT | 1699 |

| C   | H   | D   | L   | E   | N   | G   | L   | M   | C   | T   | C   | P   | A   | G   | F   | S   | G   | R   | R   | 474  |
|-----|-----|-----|-----|-----|-----|-----|-----|-----|-----|-----|-----|-----|-----|-----|-----|-----|-----|-----|-----|------|
| TGC | CAT | GAC | CTG | GAG | AAT | GGG | CTC | ATG | TGC | ACC | TGC | CCT | GCC | GGC | TTC | TCT | GGC | CGA | CGC | 1759 |

VIII

| C   | E   | V   | R   | T   | S   | I   | D   | A   | C   | A   | S   | S   | P   | C   | F   | N   | R   | A   | T   | 494  |
|-----|-----|-----|-----|-----|-----|-----|-----|-----|-----|-----|-----|-----|-----|-----|-----|-----|-----|-----|-----|------|
| TGT | GAG | GTG | CGG | ACA | TCC | ATC | GAT | GCC | TGT | GCC | TCG | AGT | CCC | TGC | TTC | AAC | AGG | GCC | ACC | 1819 |

| C   | Y   | T   | D   | L   | S   | T   | D   | T   | F   | V   | C   | N   | C   | P   | Y   | G   | F   | V   | G   | 514  |
|-----|-----|-----|-----|-----|-----|-----|-----|-----|-----|-----|-----|-----|-----|-----|-----|-----|-----|-----|-----|------|
| TGC | TAC | ACC | GAC | CTC | TCC | ACA | GAC | ACC | TTT | GTG | TGC | AAC | TGC | CCT | TAT | GGC | TTT | GTG | GGC | 1879 |

TM

| S   | R   | C   | E   | F   | P   | V   | G   | L   | L   | V   | L   | P   | S   | F   | P   | W   | V   | A   | V   | S   | L   | 534  |
|-----|-----|-----|-----|-----|-----|-----|-----|-----|-----|-----|-----|-----|-----|-----|-----|-----|-----|-----|-----|-----|-----|------|
| AGC | CGC | TGC | GAG | TTC | CCC | GTG | GGC | TTG | CTG | GTA | CTG | CCG | TCG | TTC | CCC | TGG | GTG | GCC | GTC | TCG | CTG | 1939 |

| G   | V   | G   | L   | A   | V   | L   | L   | V   | L   | G   | M   | V   | A   | V   | R   | Q   | 554  |
|-----|-----|-----|-----|-----|-----|-----|-----|-----|-----|-----|-----|-----|-----|-----|-----|-----|------|
| GGT | GTG | GGG | CTG | GCA | GTG | CTG | CTG | GTA | CTG | GGC | ATG | GTG | GCA | GTG | CGG | CAG | 1999 |

| L   | R   | L   | R   | R   | P   | D   | D   | G   | S   | R   | E   | A   | M   | N   | N   | L   | S   | D   | F   | 574  |
|-----|-----|-----|-----|-----|-----|-----|-----|-----|-----|-----|-----|-----|-----|-----|-----|-----|-----|-----|-----|------|
| CTG | CGG | CTT | CGA | CGG | CCG | GAC | GAC | GGC | AGC | AGG | GAA | GCC | ATG | AAC | AAC | TTG | TCG | GAC | TTC | 2059 |

| Q   | K   | D   | N   | L   | I   | P   | A   | A   | Q   | L   | K   | N   | T   | N   | Q   | K   | K   | E   | L   | 594  |
|-----|-----|-----|-----|-----|-----|-----|-----|-----|-----|-----|-----|-----|-----|-----|-----|-----|-----|-----|-----|------|
| CAG | AAG | GAC | AAC | CTG | ATT | CCT | GCC | GCC | CAG | CTT | AAA | AAC | ACA | AAC | CAG | AAG | AAG | GAG | CTG | 2119 |

FIG. 1D

```
E   V   D   C   G   L   D   K   S   N   C   G   K   Q   Q   N   H   T   L   D     614
GAA GTG GAC TGT GGC CTG GAC AAG TCC AAC TGT GGC AAA CAG CAA AAC CAC ACA TTG GAC    2179

Y   N   L   A   P   G   P   L   G   R   G   T   M   P   G   K   F   P   H   S     634
TAT AAT CTG GCC CCA GGG CCC CTG GGG CGG GGG ACC ATG CCA GGA AAG TTT CCC CAC AGT    2239

D   K   S   L   G   E   K   A   P   L   R   L   H   S   E   K   P   E   C   R     654
GAC AAG AGC TTA GGA GAG AAG GCG CCA CTG CGG TTA CAC AGT GAA AAG CCA GAG TGT CGG    2299

I   S   A   M   C   S   P   R   D   S   M   Y   Q   S   V   C   L   I   S   E     674
ATA TCA GCG ATG TGC TCC CCC AGG GAC TCC ATG TAC CAG TCT GTG TGT TTG ATA TCA GAG    2359

E   R   N   E   C   V   I   A   T   E   V   *                                     686
GAG AGG AAT GAA TGT GTC ATT GCC ACG GAG GTA TAA                                    2395

GGCAGGAGAGCCTACTGGACATCCCCTGCTCAGCCCCCGCGGCTGGACCTTCCTTCTGCATTGTTTACATTGCATCCTGGAT 2474

GGGACGTTTTTCATATGCAACGTGCTGCTCTCAGGAGGAGGGAATGCAGGAACCGGACAGACTGTGAACTTGCCA        2553

AGAGATGCAATACCCCTTCCACACCTTTGGGTGTCTGTCTCTGGCATCAGATTGGCAGCTGCACCAACCAGAGAGGAACAGAAG 2632

AGAAGAGAGTGCAGTAGCCCCATGGGGCCCTGCTGTGGCCTCCACTGGCATCCGTGTTTCCAAAAGTGCCTTT          2711

GGCCCCAGCCAAGGGTGCCAGGCCTAACTGGGGCACTCAGGGCAGTGTGTTGGAAATTCCACTGAGGGGAAATCAGGTG   2790

CTGCGGCCGC                                                                         2800
```

FIG. 1E

FIG. 2A

```
              1                                                                                                  100
M-DELTA1     ....MGRRSA LALAVVSALL ..CQWSSGV FELKLQEFVN KKGLLGNRNC CRGGSG.... .......... .PPCACRTFF RVCLKHYQAS VSPEPPCTYG SAVTPVLGVD
R-DELTA1     ....MGRRSA LALAVVSALL ..CQWSSGV FELKLQEFVN KKGLLGNRNC CRGGSG.... .......... .PPCACRTFF RVCLKHYQAS VSPEPPCTYG SAVTAVLGVD
H-DELTA1     .......... .......... .......... .......... .......... .......... .......... .......... .......... .......... ..........
X-DELTA1     ....MGQQRM LTLIVLSAVL ..CQISCSGL FELRLQEFVN KKGLLGNMNC CRPGSL..AS LQRCECKTFF RICLKHYQSN VSPEPPCTYG GAVTPVLGTN
C-DELTA1     ....MGGRFL LTLALLSALL CRCQVDGSGV FELKLQEFVN KKGLLSNRNC CRGGGPGGAG QQQCDCKTFF RVCLKHYQAS VSPEPPCTYG SAITPVLGAN
Z-DELTA1     .......MGR LMIAVLLCVM I.SQGFCSGV FELKLQEFLN KKGVTGNANC CKGSAAEG.. .......... .HQCECKTFF RICLKHYQAN VSPDPPCTYG GAVTPVLGSN
X-DELTA2     .......MASP LLLVYVAATL CLPLVYPAGV FELKIHSF.. .......... ...STPRPAC AAGKSCNIFF RVCLKHAQPV VSPDPPCTFG SAVSDILPSD
X-DELTA3     MAAASRSASG WALLLIVALW QQRAA.GSGV FQLQLQEFIN ERGVLASGRP CEPG...... .......... ....CRTFF RVCLKHFQAV VSPG.PCTFG TVSTPVLGTN
H-DELTA      ....MHWIK CLLITAFICFT VIVQVHSSGS FELRLKYFSN DHGRDNEGRC CSGESDGATG KCLGSCKTRF RVCLKHYQAT IDTTSQCTYG DVITPILGEN 101                                                                                                 200
M-DELTA1     SFSLPDGAG. IDPAFSNPIR FPFGFTWPGT FSLIIEALHT DSPDDLATEN ..PERLISRL TTQRHLITVGE EWSQDLHSSG RTDLRYSYRF VCDEHYYGEG
R-DELTA1     SFSLPDGAG. IDPAFSNPIR FPFGFTWPGT FSLIIEALHT DSPDDLATEN ..PERLISRL TTQRHLITVGE EWSQDLHSSG RTDLRYSYRF VCDEHYYGEG
H-DELTA1     .......... .......... .......... .......... .......... .......... .......... .......... .......... ..........
X-DELTA1     SFVPES..SN ADPTFSNPIR FPFGFTWPGT FSLIIEAIHA DSADDINLTEN ..PERLISRL ATQRHLITVGE QWSQDLHSSD RTELKYSYRF VCDEYYYGEG
C-DELTA1     SFSVPDGAGG ADPAFSNPIR FPFGFTWPGT FSLIIEALHT DSPDDLITEN ..PERLISRL ATQRHLAVGE EWSQDLHSSG RTDLKYSYRF VCDEHYYGEG
Z-DELTA1     SFQVPESFP. .DSSFTNPIP FAFGFTWPGT FSLIIEALHT DSTDDLSTEN ..PDRLISRM EWSQDLQVGG RTELKYSYRF VCDEHYYGEG
X-DELTA2     SKAITD.... ......SSPIR VPFHKFWPGI FSLIIESWTT NSAEQ.STEN .PDNLLSRL ATRRRLSIGE DWSQDIHLGQ QSELRYSYHV SCDEHYYGDS
X-DELTA3     SFAVRDDSSG GGR...NPLQ LPFNFTWPGT FSLIIEAWHA .PGDDLRPEA LPPDALISKI AIQGSLAVGQ NWLLDEQTST LTRLRYSYRV ICSDNYYGDN
D-DELTA      SVNLTDAQRF QNKGFTNPIQ FPFSFSWPGT FSLIVEAWHD TNNSGNARTN ...KLLIQRL LVQQVLEVSS EWKTNKSESQ YTSLEYDFRV TCDLNYYGSG

201   DSL                                                                               I                    II                  300
M-DELTA1     CSVFCRPRDD AFGHFTCGDR GEKMCDPGWK GQYCTDPICL PGCDDQHGYC DKPGECKCRV GWQGRYCDEC IRYPGCLHGT CQQPWQCNCQ EGWGGLFCNQ
R-DELTA1     CSVFCRPRDD AFGHFTCGER GEKMCDPGWK GQYCTDPICL PGCDDQHGYC DKPGECKCRV GWQGRYCDEC IRYPGCLHGT CQQPWQCNCQ EGWGGLFCNQ
H-DELTA1     .......... .......... .......... .......... .......... .......... .......... .......... .......... ..........
X-DELTA1     CSDYCRPRDD AFGHFSCGEK GEKLCNPGWK GLYCTEPICL PGCDEHHGYC DKPGECKCRV GWQGRYCDEC IRYPGCLHGT CQQPWQCNCQ EGWGGLFCNQ
C-DELTA1     CSVFCRPRDD RFGHFTCGER GEKVCNPGWK GQYCTEPICL PGCDEQHGFC DKPGECKCRV GWQGRYCDEC IRYPGCLHGT CQQPWQCNCQ EGWGGLFCNQ
Z-DELTA1     CSVFCRPRDD TFGHFTCGER GEIICNSGWK GQYCNEPICL PGCDEDHGFC DKPGECKCRV GFSGKYCDDC IRYPGCLHGT CQQPWQCNCQ EGWGGLFCNQ
X-DELTA2     CSDYCRPRDD NFGHYTCDEQ GNRLCMSGWK GEYCAEPICL PGCSESHGFC ELPGECKCRM GWQGELCDEC LRYPGCQHGS CSQPWECICQ EGWGGLFCDQ
X-DELTA3     CSRLCKKRND HFGHYVCQPD GNLSCLPGWT GEYCQQPICL SGCHEQNGYC SKPAECLCRP GWQGRLCNEC IPHNGCRHGT CSTPWQCTCD EGWGGLFCDQ
D-DELTA      CAKFCRPRDD SFGHSTCSET GEIICLTGWQ GDYCHIPKCA KGCE..HGHC DKPNQCVCQL GWKGALCNEC VLEPNCIHGT CNKPWTCICN EGWGGLYCNQ
```

```
                 301                                                                                                400
                                      III                                                    IV
M-DELTA1    DLNYCTHHKP CRNGATCTNT GQGSYTCSCR PGYTGANCEL EVDECAP..S PCKNGASCTD LED...SFSC TCPPGFYGKV CELSAMTCAD GPCFNG....
R-DELTA1    DLNYCTHHKP CRNGATCTNT GQGSYTCSCR PGYTGANCEL EVDECAP..S PCRNGGSCTD LED...SYSC TCPPGFYGKV CELSAMTCAD GPCFNG....
H-DELTA1    .......... .......... .......... .......... .......... .......... .EN...SYSC TCPPGFYGKI CELSAMTCAD GPCFNG....
X-DELTA1    DLNYCTHHKP CENGATCTNT GQGSYTCSCR PGYTGSNCEI EVNECDA..N PCKNGGSCSD LEN...SYTC SCPPGFYGKN CELSAMTCAD GPCFNG....
C-DELTA1    DLNYCTHHKP CKNGATCTNT GQGSYTCSCR PGYTGSSCEI EINECDA..N PCKNGGSCTD LEN...SYSC TCPPGFYGKN CELSAMTCAD GPCFNG....
Z-DELTA1    DLNYCTHHKP CQNGATCTNT GQGSYTCSCR PGFTGDSCEI EVNECSG..S PCRNGGSCTD LEN...TYSC TCPPGFYGRN CELSAMTCAD GPCFNG....
X-DELTA2    DLNYCTNHQP CRNGASCINI GQGSYSCSCR AGFTGTNCEI DINECAS..N PCKNGGSCND LEN...DYEC VCPRGFYGKN CDISAMTCED GPCFNG....
X-DELTA3    DLNYCTHHSP CKNGATCSNS GQRSYTCTCR PGYTGVDCEL ELSECDS..N PCRNGGSCKD QED...GYHC LCPPGYYGLH CEHSTLSCAD SPCFNG....
H-DELTA3    DLNYCTNHRP CKNGGTCFNT GEGLYTCKCA PGYSGDDCEN EIYSCDADVN PCQNGGTCID EPHTKTGYKC HCANGWSGKM CEEKVLTCSD KPCHQGICRN
D-DELTA     .......... .......... .......... .......... .......... .......... .......... .......... .......... ..........

401                                                                                                500
                                       V                                                      VI
M-DELTA1    GRCSDNPDG. GYTCHCPLGF SGFNCEKKMD LCGSSP.... .......... .......... .CSNGAKCVD LGNSYLCRCQ AGFSGRYCED
R-DELTA1    GRCSDNPDG. GYTCHCPAGF SGFNCEKKID LCSSSP.... .......... .......... .CSNGAKCVD LGNSYLCRCQ TGFSGRYCED
H-DELTA1    GRCSDSPDG. GYSCRCPVCY SGFNCEKKID YCSSSP.... .......... .......... .CSNGAKCVD LGDAYLCRCQ AGFSCRHCDD
X-DELTA1    GRCADNPDG. GYICFCPVGY SGFNCEKKID YCSSNP.... .......... .......... .CANGARCED LGNSYICQCQ EGFSGRNCDD
C-DELTA1    GRCTDNPDG. GYSCRCPLGY SGFNCEKKID YCSSSP.... .......... .......... .CANGAQCVD LGNSYICQCQ AGFTGRHCDD
Z-DELTA1    GHCADNPEG. GYFCQCPMGY AGFNCEKKID HCSSNP.... .......... .......... .CSNDAQCLD LVDSYLCQCP EGFTGTHCED
X-DELTA2    GTCIEKSSGV GYVCRCPFNY HGSNCEKKID RCTNSP.... .......... .......... .CLNGGQCLD MGRNVLCKCR PGFSGPRCEL
X-DELTA3    GSCRERNQGA NYACECPPNF TGSNCEKKVD RCTSNP.... .......... .......... .CANGGQCLN RGPSRMCRCR PGFTGTYCEL
H-DELTA3    VRPGLGSKGQ GYQCECPIGY SGPNCDLQLD NCSPNPCING GSCQPSGKCI CPAGFSGTRC ETNIDDCLGH QCENGGTCID MVNQYRCQCV PGFHGTHCSS
D-DELTA     .......... .......... .......... .......... .......... .......... .......... .......... .......... ..........

501                                                                                                600
                                      VII                                                    VIII
M-DELTA1    NVDDCASSPC ANGGTCRDSV NDFSCTCPPG YTGKNCS..A PVSRCEHAPC HNGATCHQ.. RGQRYMCECA QGYGGPNCQF LLPEPPPGPM VVDLSERH..
R-DELTA1    NVDDCASSPC ANGGTCRDSV NDFSCTCPPG YTGRNCS..A PVSRCEHAPC HNGATCHQ.. RGQRYMCECA QGYGGANCQF LLPEPPPDLI V.........
H-DELTA1    NVDDCASSPC ANGGTCRDGV NDFSCTCPPG YTGRNCS..A PASRCEHAPC HNGATCHE.. RGHRY..... .......... .......... ..........
X-DELTA1    NLDDCTSFPC QNGGTCQDGI NDYSCTCPPG YIGKNCS..M PITKCEHNPC HNGATCHE.. RNNRYVCQCA RGYGGNNCQF LLPE..EKPV VVDLTEKY..
C-DELTA1    NVDDCASFPC VNGGTCQDGV NDYSCTCPPG YNGKNCS..T PVSRCEHNPC HNGATCHE.. RSNRYVCECA RGYGGLNCQF LLPEPPQGPV IVDFTEKY..
Z-DELTA1    NIDECATYPC QNGGTCQDGL SDYTCTCPPG YTGKNCT..S AVNKCLHNPC HNGATCHE.. MDNRYVCACI PGYGGRNCQF LLPENPQGQA IVEGADKRYS
X-DELTA2    NIDDCASSPC ANGGTCVDAV NSYTCSCTLG YGGKDCT..L RVDACSSKPC KNGGTCYT.. HFTGNVCQCP TGFMGTSCEF RVHDPTPASH RADSSNT...
X-DELTA3    HVSDCARNPC AHGGTCHDLE NGLMCTCPAG FSGRRCEVRT SIDADASSPC FNRATCYTDL STDTFVCNCP YGFVGSRCEF PVGLPP.... ..........
H-DELTA3    KVDLCLIRPC ANGGTCLNLN NDYQCTCRAG FTGKDCS..V DIDECSSGPC HNGGTCMN.. RVNSFECVCA NGFRGKQCD. ...EESYDSV TFDAHQYGAT
```

FIG. 2B

FIG. 2C

```
          601                                                                                              700
M-DELTA1  MESQGGPFPW VAVCAGVVLV L...LLLLGC AAVVVCVRLK LQKHQPPPEP CGGETETMNN LANCQ.REKD VSVSIIGATQ IKNTNKKADF ..HGDHGAK
R-DELTA1  .AAQGGSFPW VAVCAGVVLV L...LLLLGC AAVVVCVRLK LQKHQPPPDP CGGETETMNN LANCQ.REKD VSVSIIGATQ IKNTNKKADF ..HGDHGAD
H-DELTA1  .......... .......... .......... .......... .......... .......... .......... .......... .......... ..........
X-DELTA1  TEGQSGQFPW IAVCAGIVLV L...MLLLGC AAVVVCVRVR VQKRRHQPEA CRGESKTMNN LANCQ.REKD ISVSFIGTTQ IKNTNKKIDF ..LSESNNE
C-DELTA1  TEGQNSQFPW IAVCAGIILV L...MLLLGC AAIVVCVRLK VQKRRHQPEA CRSETETMNN LANCQ.REKD ISISVIGATQ IKNTNKKVDF ..HSD.NSD
Z-DELTA1  YEEDDGGFPW TAVCAGIILV L...LVLIGG SVFVIYIRLK LQQRSQQID. SHSEIETMNN LTNNRSREKD LSVSIIGATQ VKNINKKVDF ..QSD..GD
X-DELTA2  .......... LTMVVCLGLL T...FFLLGC GVFMV.MRGM RGHFNEKGR VNNDLEPKNN LIE...KEPH FKMPNPDYLR EKSSSKQKLL ..QG......
H-DELTA3  ......SFPW VAVSLGVGLA V...LLVLLG MVAVAVRQLR LRRPD..... .DGSREAMNN LSDFQKDN.. ...LIPAAQ LKNTNQKKEL ..EVDCGLD
D-DELTA   TQARADGLTN AQVVLIAVFS VAMPLVAVIA ACVVFCMKRK RKRAQEKDDA EARKQNEQNA VATMHHNGSG VGVALASASL GGKTGSNSGL TFDGGNPNII 701                                                                                              800
M-DELTA1  KSSF.KVRYP TVDYNLVRDL KGDEATVRDT HSKRDTKCQS QSSAGEEKIA PTLRGGEIPD RKRPESVYST SKDTKYQSVY VLSAEKDECV IATEV.....
R-DELTA1  KSSF.KARYP TVDYNLIRDL KGDEATVRDA HSKRDTKCQS QGSVGEEKST STLRGGEVPD RKRPESVYST SKDTKYQSVY VLSAEKDECV IATEV.....
H-DELTA1  .......... .......... .......... .......... .......... .......... .......... .......... .......... ..........
X-DELTA1  KNGY.KPRYP SVDYNLVHEL KNEDS.PKEE RSKCEAKCSS NDSDSEDVNS VHSK.RDSSE RRRPDSAYST SKDTKYQSVY VISDEKDECI IATEV.....
C-DELTA1  KNGY.KVRYP SVDYNLVHEL KNEDS.VKEE HGKCEAKCET YDSEAEEKSA VQLKSSDTSE RKRPDSVYST SKDTKYQSVY VISEEKDECI IATEV.....
Z-DELTA1  KNGF.KSRYS LVDYNLVHEL KQEDLGKEDS ERSEATKCEP LDSDSEEKHR NHLK.SDSSE RKRTESLC.. .KDTKYQSVF VLSEEKDECI IATEV.....
X-DELTA2  .......... .......... .......... .......... ..SESEEERS GR.RTDRKPD TKQCNPTSRY PEDGAYHPIY ILP.EPEQCI FATEV.....
H-DELTA3  KSNCGKQQNH TLDYNL.... ...APGPLIG RGTMPGKFPH SDKSLGEKAP LRLHSEKPEC R...ISAICS PRDSMYQSVC LISEERNECV IATEV.....
D-DELTA   KNTWDKSVNN ICASAAAAAA AAAAADECLM YGGYVASVAD NNNANSDFCV APLQRAKSQK QLNTDPTLMH RGSPAGSSAK GASGGGPGAA EGKRISVLGE 801                          850
M-DELTA1  .......... .......... .........
R-DELTA1  .......... .......... .........
H-DELTA1  .......... .......... .........
X-DELTA1  .......... .......... .........
C-DELTA1  .......... .......... .........
Z-DELTA1  .......... .......... .........
X-DELTA2  .......... .......... .........
H-DELTA3  .......... .......... .........
D-DELTA   GSYCSQRWPS LAAAGVAGAC SSQLMAAASA AGTDGTAQQQ RSVVCGTPHM
```

HUMAN DELTA3 NUCLEIC ACID MOLECULES

RELATED APPLICATIONS

This application is a continuation-in-part of U.S. Ser. No. 08/832,633 filed Apr. 4, 1997 now abandoned entitled "Novel Human Delta3 Compositions and Therapeutic and Diagnostic Uses Therefor", the teachings of which are incorporated herein by reference.

1. BACKGROUND OF THE INVENTION

In developed countries, stroke is the third leading cause of death and the primary cause of acquired physical or cognitive impairment. Vascular dementia is the second leading cause of dementia, after Alzheimer's disease. CADASIL (for cerebral autosomal dominant arteriopathy with lubcortical infarcts and leukoencephalopathy) causes a type of stroke and dementia whose key features include recurrent subcortical ischaemic events, progressive vascular dementia, craniofacial paralysis, migraine and mood disorders with severe depression (Chabriat, H. et al., (1995) Lancet 346: 934–939). These symptoms usually start to appear at about 45 years of age, and patients typically die by 65. The condition is believed to be largely undiagnosed and therefore the prevalence is not precisely known.

CADASIL is associated with diffuse white-matter abnormalities on neuroimaging (Tournier-Lasserve, E. et. al., (1991) Stroke 22:1297–1302). Pathological examination reveals multiple small, deep cerebral infarcts, a leukoencephalopathy and a non-atherosclerotic, non-amyloid angiopathy involving mainly the small cerebral arteries. (Baudrimont, M. et al., (1993) Stroke 24: 122–125). Severe alterations of vascular smooth muscle cells are evident on ultrastructural analysis (Ruchoux, M. M. et al., (1995) Acta. Neuropathol. 89:500–512).

It has recently been shown that the human Notch3 gene, located on chromosome 19, is mutated in CADASIL patients (Joutel. A. et al., (1996) Nature 383: 707–710). Most of the mutations cause amino acid changes in the extracellular domain. Therefore, disruption of the Notch signaling pathway appears to be responsible for CADASIL stroke and dementia.

Defects in the Notch signaling pathway may also be involved in other neurological diseases, e.g., Alzheimer's disease. In fact, approximately 10% of cases of Alzheimer's disease are associated with mutations in genes encoding the amyloid precursor proteins, presenilin 1 (PS1) and presenilin 2 (PS2). About 25% of early-onset familial Alzheimer's cases are associated with a mutation in PS1. PS1 and PS2 are transmembrane proteins which are homologous to the C. elegans protein encoded by the sel-12 gene, which has been shown to be genetically linked to the C. elegans lin-12 gene, which encodes a Notch-family receptor (Levitan, D. and I. Greenwald (1995) Nature 377:351–354; PS1 and PS2 are further described in PCT Application WO 96/34099; Sel12 is further described in PCT Application WO 97/11956). Furthermore, targeted disruption of PS1 in mice results in reduced expression of mRNA encoding Notch1 and Delta-like gene 1 (Dll1), a vertebrate Notch ligand, in the presomitic mesoderm compared to control mice (Wong et al. (1997) Nature 387:288). This indicates that PS1 is required for the spatiotemporal expression of genes involved in the Notch signaling pathway.

The Notch signaling pathway comprises Notch proteins, which are membrane proteins, and proteins interacting with Notch proteins, termed Delta proteins. The product of the Delta gene, acting as a ligand, and that of the Notch gene, acting as a receptor, are key components in a lateral-inhibition signaling pathway that regulates the detailed patterning of many different tissues in Drosophila (Vassin, H., et al., (1987) EMBO J 6:3431–3440; Kopczynski, C. et al., (1988) Genes Dev. 2:1723–1735; Fehon, R. G. et al., (1990) Cell 61:523–534; Artavanis-Tsakonas, S. et., al., (1991) Trends, Genet. Sci. 7:403–407; Heitzler, P. et. al., (1991) Cell 64: 1083–1092; Greenwald, I. et al., (1992) Cell 68: 271–281; Fortini, M et al., (1993) Cell 75: 124501247; and Muskavitch, M. (1994) Devl. Biol. 166:415–430). During neurogenesis in particular, neural precursors, by expressing Delta, inhibit neighboring Notch-expressing cells from becoming committed to a neural fate. Mutations leading to a failure of lateral inhibition cause an overproduction of neurons, giving rise to a phenotype termed the "neurogenic phenotype" in Drosophila. For example, loss of Notch1 leads to somite defects and embryonic death in mice, whereas constitutively active mutant forms of Notch1 appear to inhibit cell differentiation in Xenopus and in cultured mammalian cells (Swiatek et al. (1994) Genes Dev. 8:707; Conlon et al. (1995) J. Development 121:1533; Lopan et al. (1994) Development 120:2385; and Nye et al. (1994) Development 120:2421). Similarly, reduced activity of X-Delta1 causes more cells to become primary neurons, whereas raised activity causes fewer cells to become primary neurons (Chitnis et al. (1995) Nature 375:761). Furthermore, loss of Dll1 function in mice leads to excessive neuronal differentiation, resulting in severe patterning defects in the paraxial mesoderm and a hyperplastic central nervous system (CNS) (Hrabe de Angelis et al. (1997) Nature 386:717). Thus, the Notch signaling pathway, in particular Delta proteins, mediate lateral inhibition during neurogenesis so that only a limited proportion of cells having the potential to become neurons will in fact differentiate into neurons.

The Notch family of proteins are transmembrane receptors containing several conserved peptide motifs. The extracellular domains contain many tandemly repeated copies of an epidermal growth factor (EGF) like motif. The intracellular domains contain six copies of another conserved motif, termed the Cdc10/ankyrin repeat. Both the EGF and the ankyrin-repeat motifs are found in many different proteins and, in at least some cases, they have been shown to be involved in protein-protein interactions.

The Drosophila Notch protein encodes a glycosylated transmembrane receptor having a molecular mass 350 KD, which is involved in cell-fate specification during development (Wharton, K. A. et al., (1985) Cell 43:567–581); Artavanis-Tsakonas, S. et al., (1995) Science 268: 225–232). Based on analysis of *Drosophila mutants*, it is thought that Notch is a receptor having different functional domains, with the intracellular domain having the intrinsic signal-transducing activity of the intact protein and the extracellular domain a regulating activity (Rebay, I et al., (1993) Cell 74: 319–329).

Several Notch homologues have been identified in vertebrates (Larsson, C., et al., (1994) Genomics 24: 253–258). Three Notch proteins (Notch1, also called TAN1, Notch2, and Notch3) have been characterized in humans (Ellisen, L. W. et al., (1991) Cell 66:649–661; Stifani, S. et al., (1992) Nature Genet. 2: 119–127). Notch1 gene translocations have been associated with a minority of T-cell lymphoblastic leukemias (Aster, J. (1994) Cold Spring Harb. Symp. Quant. Biol. 59:125–136) and Notch3 has been linked with CADASIL.

A protein interacting with Notch was first discovered in Drosophila and has been called Delta protein. This protein encodes a transmembrane protein ligand, which contains tandem arrays of epidermal growth factor-like repeats in the extracellular domain. The Delta and Notch proteins can directly bind to each other and specific EGF-like repeats are sufficient and necessary for this binding (Fehon, R. G. et al., (1990) Cell 61:523–534; Rebay I., et al., (1991) Cell 67:687–699; and Lieber, T., et al., (1992) Neuron 9: 847–859).

In addition to the Drosophila Delta protein, a chick Delta homologue, C-Delta protein (Henrique, D et al., (1995) Nature 375: 787–790 and GenBank Accession No. U26590) two Xenopus homologues, X-Delta-1 and X-Delta-2 (Chitnis, A. et al., (1995) Nature 375:761–766 and GenBank Accession Nos. L42229 and U70843), a mouse homologue (GenBank Accession No. X80903), a delta-like human gene 1(Dlk) (Bettenhausen, B. et al., (1995) Development 121:2407–2418) a rat homologue (GenBank Accession No. U78889), and a Zebrafish homologue (GenBank Accession No. Y11760) have been identified. Xenopus, chick and mouse Delta genes are also disclosed in International Patent Application No. PCT/US96/11178 (Publication No. WO 97/01571. The patent application also discloses a partial and error prone human Delta homolog (hD1). Nucleotide sequence of human Notch genes are disclosed in International Patent Application No. PCT/US92/03651 (Publication No. WO 92/19734) and International Patent Application No. PCT/US93/09338 (Publication No. WO 94/07474).

Notch signaling pathway therapeutics, in particular Delta therapeutics are highly desirable for treating various diseases and disorders, including neurological and vascular disorders.

2. SUMMARY OF THE INVENTION

The invention is based at least in part on the discovery of a human gene encoding a novel Delta protein which differs substantially from the previously described Delta proteins. Accordingly, the novel Delta protein of the invention is referred to herein as Delta3. Thus, the invention provides Delta3 proteins, and nucleic acids encoding Delta3 proteins. An exemplary hDelta3 is contained in a plasmid which was deposited with the American Type Culture Collection (ATCC) on Mar. 5, 1997, and has been assigned ATCC accession number 98348.

Based on Northern blot analysis of RNA prepared from a number of human tissues, a 3.5 kb message was expressed in fetal brain, lung, liver and kidney; and adult heart, placenta, lung, skeletal muscle, kidney, pancreas, spleen, thymus, prostate, testis, ovary, small intestine and colon. In addition, the hDelta3 gene was found to be expressed at relatively high levels in at least some tumor cells (e.g. colon carcinoma) and its expression could be up-regulated in response to various growth factors (e.g., bFGF and VEGF). Furthermore, the expression of hDelta3 was also shown to be increased in response to a signal induced differentiation of endothelial cells, indicating a role for hDelta3 in modulating the growth and/or differentiation of cells, in particular endothelial cells.

As described herein, the hDelta3 gene has been localized on human chromosome 15, close to framework markers D15S1244 and D15S144, a chromosomal region that has been associated with the neurological disease Agenesis of the Corpus Callosum with Peripheral Neuropathy (ACCPN) (Casaubon et al. (1996) Am J. Hum. Genet. 58:28). Accordingly, polymorphisms in Delta3 are thought to be involved in this neurological disease. As described further herein, Delta3 is also likely to be involved in other neurological diseases as well as in non-neurological diseases.

In one aspect, the invention features isolated Delta3 nucleic acid molecules, e.g., human Delta3 nucleic acids. The disclosed molecules can be non-coding, (e.g., probe, antisense or ribozyme molecules) or can encode a functional Delta3 polypeptide, e.g. a polypeptide which can modulate at least one bioactivity of a Delta3 polypeptide. In one embodiment, the nucleic acid molecules hybridize to the Delta3 gene contained in the plasmid having ATCC Accession No. 98348. In another embodiment, the claimed nucleic acid is capable of hybridizing to the nucleotide sequence set forth in SEQ ID No. 1 and/or SEQ ID No: 3 or to the complement thereof. In a preferred embodiment, the hybridization is conducted under mildly stringent or stringent conditions.

In further embodiments, the nucleic acid molecule is a Delta3 nucleic acid that is at least about 50%, 60%, 70%, preferably 80%, more preferably 85%, and even more preferably at least about 95% homologous in sequence to the nucleic acids shown as SEQ ID Nos: 1 and/or 3 or to the complement of the nucleic acids shown as SEQ ID Nos: 1 and/or 3. In another embodiment, the nucleic acid molecule encodes a polypeptide that is at least about 50%, 60%, 70%, preferably 80%, more preferably 85%, and even more preferably at least about 90 or 95% similar or identical in sequence to the polypeptide shown in SEQ ID No. 2. In a further embodiment, the nucleic acid molecule is a nucleic acid that is at least about 70%, preferably 80%, more preferably 85% and even more preferably at least about 90% or 95% similar in sequence to the hDelta3 gene contained in the plasmid having ATCC Accession Number 98348.

Preferred nucleic acids of the invention comprise a nucleotide sequence encoding at least one domain or motif of a Delta 3 protein, i.e., a domain or motif selected from the group consisting of a signal peptide, a Delta similarity (DSL) domain, Epidermal Growth Factor (EGF) like repeat 1, EGF-like repeat 2, EGF-like repeat 3, EGF-like repeat 4, EGF-like repeat 5, EGF-like repeat 6, EGF-like repeat 7, and EGF-like repeat 8, a transmembrane domain (TM), and a cytoplasmic domain. Other preferred nucleic acids encode soluble Delta3 proteins, e.g. Delta3 proteins comprising at least a portion of the extracellular domain of a Delta3 protein. These soluble polypeptides may or may not comprise a signal peptide. Even more preferred nucleic acids encode soluble fusion proteins comprised of Delta3 proteins and a heterologous peptide, e.g., an immunoglobulin constant region.

The invention also provides probes and primers comprising substantially purified oligonucleotides, which correspond to a region of nucleotide sequence which hybridizes to at least about 6 consecutive nucleotides of the sequences set forth as SEQ ID Nos: 1 or 3 or complements of the sequences set forth as SEQ ID Nos 1 and/or 3, or naturally occurring mutants thereof. In preferred embodiments, the probe/primer further includes a label group attached thereto, which is capable of being detected.

For expression, the subject Delta3 nucleic acids can include a transcriptional regulatory sequence, e.g. at least one of a transcriptional promoter (e.g., for constitutive expression or inducible expression) or transcriptional enhancer sequence, the regulatory sequence is operably linked to the Delta3 gene sequence. Such regulatory sequences in conjunction with Delta3 nucleic acid molecules can be useful in vectors for gene expression. This invention also describes host cells transfected with said expression vectors whether prokaryotic or eukaryotic, also in vitro (e.g. cell culture) and in vivo (e.g. transgenic) methods for producing Delta3 proteins by employing said expression vectors.

In another aspect, the invention features isolated Delta3 polypeptides, preferably substantially pure preparations, e.g. of plasma purified or recombinantly produced Delta3 polypeptides. In preferred embodiments, the subject polypeptides are capable of modulating an activity of a Delta3 polypeptide, e.g., cell growth and/or differentiation or induction of apoptosis. In preferred embodiments, the subject Delta3 polypeptides can modulate neurogenesis (e.g. by inhibiting Notch expressing cells from becoming committed to a neural fate). In addition, Delta3 polypeptides which specifically antagonize the activity of a native Delta3 polypeptide, such as may be provided by truncation mutants or other dominant negative mutants, are also specifically provided herein.

In one embodiment, the polypeptide is identical or substantially similar to a Delta3 protein represented in SEQ ID No. 2. Preferably, a Delta3 polypeptide has an amino acid sequence, which is at least about 50%, 60%, 70%, preferably at least about 80%, more preferably at least about 90%, and even more preferably at least about 95% homologous or identical to the polypeptide represented by SEQ ID No. 2. In a preferred embodiment, the Delta3 polypeptide is encoded by a nucleic acid which hybridizes with a nucleic acid sequence represented in one of SEQ ID Nos. 1 or 3 or with the nucleic acid contained in the plasmid having ATCC Accession No. 98348. The subject Delta3 proteins also include modified proteins, which are resistant to post-translational modification, as for example, due to mutations which alter modification sites (such as tyrosine, threonine, serine or asparagine residues), or which prevent glycosylation of the protein, or which prevent interaction of the protein with intracellular proteins involved in signal transduction.

The Delta3 polypeptide can comprise a full length protein, such as represented in SEQ ID No. 2, or it can comprise a fragment corresponding to one or more particular motifs/domains, or to arbitrary sizes, e.g., at least 5, 10, 25, 50, 100, 150, 200, 250, 300, 350, 400, 450, 500, 550, 600 or 650 amino acids in length.

Another aspect of the invention features chimeric molecules (e.g. fusion proteins) comprised of a Delta3 protein. For instance, the Delta3 protein can be provided as a recombinant fusion protein which includes a second polypeptide portion, e.g., a second polypeptide having an amino acid sequence unrelated (heterologous) to the Delta3 polypeptide, (e.g. the second polypeptide portion is glutathione-S-transferase, an enzymatic activity such as alkaline phosphatase or an epitope tag).

Preferred fusion proteins are Delta3 immunoglobulin (Delta3-Ig) fusion proteins. For example, a Delta3 fusion protein can comprise the extracellular portion of a Delta3 protein fused to the constant region of an immunoglobulin molecule. Preferred extracellular portions comprise at least one domain selected from the group consisting of a signal peptide, a DSL domain, and the eight EGF-like repeats of a Delta3 protein. An even more preferred extracellular domain comprises an amino acid sequence from about amino acid 1 to about amino acid 529 of SEQ ID No. 2. Yet other preferred Delta3 fusion proteins comprise a portion of a Delta3 protein that is sufficient for binding to a second protein, e.g., a Notch protein.

Yet another aspect of the present invention concerns an immunogen comprising a Delta3 polypeptide in an immunogenic preparation, the immunogen being capable of eliciting an immune response specific for a Delta3 polypeptide, e.g. a humoral response, an antibody response and/or cellular response. In preferred embodiments, the immunogen comprises an antigenic determinant, e.g. a unique determinant, from the protein represented by SEQ ID No. 2.

A still further aspect of the present invention features antibodies and antibody preparations specifically reactive with an epitope of the Delta3 protein. In preferred embodiments, the antibody specifically binds to an epitope represented in SEQ ID No: 2.

The invention also features transgenic non-human animals which include (and preferably express) a heterologous form of a Delta3 gene described herein, or which misexpress an endogenous Delta3 gene (e.g., an animal in which expression of one or more of the subject Delta3 proteins is disrupted). Such a transgenic animal can serve as an animal model for studying cellular or tissue disorders comprising mutated or misexpressed Delta3 alleles or for use in drug screening. For example, the transgenic animals of the invention can be used as an animal model to study a neurological disease, e.g., ACCPN. Alternatively, such a transgenic animal can be useful for expressing recombinant polypeptides.

In yet another aspect, the invention provides assays, e.g., for screening test compounds to identify agonists, or alternatively, antagonists, of a bioactivity. For example, the test compound may positively or negatively influence an interaction between a Delta3 protein and a Delta3 target molecule, for example, a Notch protein. An exemplary method includes the steps of (i) combining a Delta3 polypeptide or bioactive fragment thereof, a Delta3 target molecule, e.g., Notch, and a test compound, e.g., under conditions wherein, but for the test compound, the Delta3 protein and target molecule are able to interact; and (ii) detecting the formation of a complex which includes the Delta3 protein and the target molecule either by directly quantitating the complex, by measuring inductive effects of the Delta3 protein, or, in the instance of a substrate, measuring the conversion to product. A statistically significant change, such as a decrease, in the interaction of the Delta3 and target molecule in the presence of a test compound (relative to what is detected in the absence of the test compound) is indicative of a modulation (e.g., suppression or potentiation of the interaction between the Delta3 protein and the target molecule).

The invention provides yet other methods for identifying compounds which modulate a Delta activity. For example, a compound interacting with a Delta3 protein can be identified by contacting a Delta3 protein with a test compound. Either the test compound or the Delta3 protein can be labeled and/or optionally attached to a solid phase support. Binding of the test compound to the Delta3 protein can then be determined, e.g. by measuring the amount of label. Such a Delta3 binding molecule can be an agonist or an antagonist. In one embodiment, an agonist of a Delta3 activity is identified by contacting a cell having a Delta3 protein with a test compound and measuring a Delta3 activity, e.g., expression of a gene which is regulated by binding of a protein, e.g., a Notch protein, to Delta3. An increased expression of the gene when the cell is incubated with the test compound relative to incubation in the absence of the test compound indicates that the test compound is a Delta3 agonist. The gene that is monitored can also be a reporter gene transfected to a cell, the reporter gene being under the control of a promoter of a gene which is regulated by Delta3.

Yet another aspect of the present invention concerns methods for treating diseases or conditions that are caused or contributed to by an aberrant Delta3 activity, e.g., aberrant cell proliferation, degeneration or differentiation in a subject, by administering to the subject an effective amount of an agonist or antagonist of a Delta3 bioactivity. In one embodiment, an agonist or antagonist can modulate Delta3 protein levels, by, e.g., modulating expression of a Delta3 gene. For example, administration of a therapeutic comprised of a Delta3 agonist can be useful for promoting the tissue regeneration or repair needed to effectively treat a nerve injury, neurodegenerative disease, or neurodevelopmental disorder including but not limited to peripheral neuropathies, e.g., ACCPN, stroke, dementia, Alzheimer's disease, Parkinson's disease, Huntington's chorea, amylotrophic lateral sclerosis, an the like, as well as spinocerebellar degenerations. Alternatively, administration of a Delta3 antagonist may be to effectively treat a neoplastic or hyperplastic disease, particularly of endothelial tissue.

The invention also provides methods for treating diseases or conditions associated with one or more specific Delta alleles, e.g., mutant allele, comprising administering to the subject an effective amount of a therapeutic compound. In one embodiment, the therapeutic compound is capable of compensating for the effect of the specific Delta allele. In another embodiment, the therapeutic compound is capable of modulating a Delta3 activity. In a preferred embodiment, the Delta allele is a Delta3 allele. In an even more preferred embodiment, the disease or condition is a neurological disease, e.g., ACCPN.

A further aspect of the present invention provides a method for determining whether a subject is at risk for developing a disease or condition, which is caused by or contributed to by an aberrant Delta3 activity, e.g. aberrant cell proliferation, degeneration or differentiation. In a preferred embodiment, the disease or condition is a neurological disease, e.g., ACCPN. The method includes detecting, in a tissue of the subject, the presence or absence of a genetic lesion characterized by at least one of (i) a mutation of a gene encoding a Delta3 protein, e.g. represented in one of SEQ ID Nos: 1 or 3 or a homolog thereof; or (ii) the mis-expression of a Delta3 gene. In preferred embodiments, detecting the genetic lesion includes ascertaining the existence of at least one of the following: a deletion of one or more nucleotides from a Delta3 gene; an addition of one or more nucleotides to the gene, a substitution of one or more nucleotides of the gene, a gross chromosomal rearrangement of the gene; an alteration in the level of a messenger RNA transcript of the gene; the presence of a non-wild type splicing pattern of a messenger RNA transcript of the gene; and/or a non-wild type level of the protein.

In a preferred embodiment, the invention provides a method for determining whether a subject has or is at risk of developing a disease or condition associated with a specific Delta allele, comprising determining the identity of a Delta allele in the subject. A preferred Delta allele is a Delta3 allele. In an even more preferred embodiment, the disease or condition is a neurological disease, e.g., ACCPN. In another preferred embodiment, the disease is a vascular disorder.

For example, detecting the genetic lesion or determining the identity of a Delta allele, e.g., a Delta3 allele, can include (i) providing a probe/primer comprised of an oligonucleotide which hybridizes to a sense or antisense sequence of a Delta3 gene or naturally occurring mutants thereof, or 5' or 3' flanking sequences naturally associated with the Delta3 gene; (ii) contacting the probe/primer with an appropriate nucleic acid containing sample; and (iii) detecting, by hybridization of the probe/primer to the nucleic acid, the presence or absence of the genetic lesion; e.g. wherein detecting the lesion comprises utilizing the probe/primer to determine the nucleotide sequence of the Delta3 gene and, optionally, of the flanking nucleic acid sequences. For instance, the primer can be employed in a polymerase chain reaction (PCR) or in a ligation chain reaction (LCR).

In another diagnostic method of the invention, at least a portion of a Delta3 gene of a subject is sequenced and the nucleotide sequence is compared to that of a wild-type Delta3 gene, to determine the presence of a genetic lesion. Another preferred diagnostic method of the invention is single strand conformation polymorphism (SSCP) which detects differences in electrophoretic mobility between mutant and wild-type nucleic acids.

In alternate embodiments, the diagnostic methods comprise determining the level of a Delta3 protein in an immunoassay using an antibody which is specifically immunoreactive with a wildtype or mutant Delta3 protein.

Other features and advantages of the invention will be apparent from the following detailed description and claims.

3. BRIEF DESCRIPTION OF THE FIGURES

FIGS. 1A–1C show a DNA sequence of the human Delta3 gene including 5' and 3' noncoding sequences (SEQ ID No 1), as well as the deduced amino acid sequence of the human Delta3 protein (SEQ ID No 2). The various domains of the protein are indicated.

FIG. 2 shows a multiple sequence alignment of the novel human Delta3 protein (h-Delta3 ) (SEQ ID No 2) with the mouse Delta1 protein (m-delta1) (SEQ ID No 4), the rat Delta1 protein (r-delta1) (SEQ ID No 5), the partial human Delta1 (WO 97/01571) protein (SEQ ID No 6), the Xenopus Delta1 protein (x-delta1) (SEQ ID No 7), the chick Delta1 protein (c-delta1) (SEQ ID No 8), the zebrafish Delta1 protein (z-delta1) (SEQ ID No 9) the Xenopus Delta2 protein (x-delta2) (SEQ ID No 10) and the Drosophila Delta1 protein (d-delta1) (SEQ ID No 11). Conservation of the Delta3 similarity (DSL) domain, the epidermal growth factor-like (EGF) repeats (numbered I–VIII) and the transmembrane domain (TM) is indicated. The GenBank Accession No. of each of these Delta proteins (with the exception of the partial human sequence, which is not in GenBank) is indicated in Table I.

FIG. 3 shows a phylogenic tree indicating the relationship of hDelta3 with the partial human delta1 (WO 97/01571) protein, the mouse Delta1 protein (m-delta1), the rat Delta1 protein (r-delta1), the Xenopus Delta1 protein (x-delta1), the chick Delta1 protein (c-delta1), the Xenopus Delta2 protein (x-delta2), the zebrafish Delta1 protein (z-delta1), and the Drosophila Delta1 protein (d-delta1). The GenBank Accession No. of each of these Delta proteins (with the exception of the partial human sequence, which is not in GenBank) is indicated in Table I.

4. DETAILED DESCRIPTION OF THE INVENTION

1. General

The present invention is based at least in part on the discovery of a novel gene encoding a human Delta protein, referred to herein as "hDelta3 " polypeptide. An exemplary hDelta3 has been deposited under the Budapest Treaty with the American Type Culture Collection (ATCC) 10801 University Boulevard, Manassas Va. 20110-2209 on Mar. 5, 1997 and has been assigned ATCC accession number 98348. The human Delta3 gene maps to human chromosome 15.

FIG. 1 shows the DNA sequence of the human Delta3 gene including 5' and 3' noncoding sequences (SEQ ID No. 1), the coding sequence (SEQ ID No. 3), as well as the deduced amino acid sequence of the human Delta3 protein (SEQ ID No. 2).

Human Delta3 is expressed in endothelial cells and in fact was cloned from a human microvascular endothelial cell library. Northern blot analysis of RNA prepared from a number of different human tissues, indicate that a 3.5 kb Delta3 mRNA transcript is present in fetal brain, lung, liver and kidney, and adult heart, placenta, lung, skeletal muscle, kidney, pancreas, spleen, thymus, prostate, testis, ovary, small intestine and colon. Low levels of Delta3 mRNA was also detected in adult brain and adult liver. However, no Delta3 mRNA was detected in peripheral blood leukocytes. These results indicate that Delta3 is expressed in a tissue specific manner. Further, expression in human MV endothelial cells was found to be up-regulated (about 2–3 fold) in cells that had been stimulated with certain growth factors (e.g. basic fibroblast growth factor (bFGF) or vascular endothelial growth factor (VEGF)). In addition, strong expression of human Delta3 was observed in the colorectal carcinoma cell line, SW480. Furthermore, expression of hDelta3 has been shown to be induced in response to proliferation and differentiation signals (See Examples). Thus, hDelta3 gene is a gene whose expression in a cell changes with the state of proliferative and/or differentiative state of cells.

As predicted from the nucleotide sequence of the nucleic acid encoding hDelta3, the full length hDelta3 polypeptide comprises 685 amino acids and is similar in sequence and structure to Delta proteins obtained from other organisms (See FIG. 2 and discussed below). An amino acid sequence analysis of the human Delta3 protein predicts that the protein comprises at least the following structural domains: a signal peptide, corresponding to about amino acid 1 to about amino acid 17 of SEQ ID No. 2, a Delta Similarity (DSL) motif corresponding to about amino acid 173 to about amino acid 217 of SEQ ID NO: 2 (FIG. 2), eight epidermal growth factor (EGF)-like repeats corresponding essentially to the sequences indicated in FIG. 2, a transmembrane domain corresponding to about amino acid 530 to about amino acid 553 of SEQ ID No. 2 (FIG. 2), and a cytoplasmic domain corresponding to about amino acid 554 to about amino acid 685 of SEQ ID No. 2 (FIG. 2). Accordingly, the amino acid sequence of hDelta3 predicts that the protein is a transmembrane protein having an extracellular domain corresponding to about amino acid 1 or amino acid 18 to about amino acid 529 of SEQ ID No. 2 (FIG. 2) comprising the DSL motif and the EGF-like repeats, a transmembrane domain and a cytoplasmic domain. It is possible that the signal peptide comprises more than 17 amino acids of SEQ ID No. 2, since the region from amino acid 1 to about amino acid 20 form a hydrophobic region.

It is possible that soluble forms of the protein also exist. Such soluble isoforms can arise through variable splicing of the Delta3 gene or alternatively as a result of proteolysis of a membranous isoform. In fact, a splice variant of a chicken Delta protein have been described in PCT Application PCT/US96/11178 having Publication No. WO 97/01571. Furthermore, the human Delta-like polypeptide Dlk is a soluble protein (Jansen et al. [1994] Eur. J. Biochem. 225:83–92).

Human Delta3 protein is similar in structure and in sequence to the Delta proteins identified in Drosophila, Xenopus, zebrafish, chicken, rat, mouse, rat, and human. An alignment of the amino acid sequences of the Delta proteins known to date is shown in FIG. 2. This alignment contains the following Delta proteins, encoded by genes for which the GenBank Accession Nos. are shown in Table I: a mouse Delta1 protein (m-delta1), rat Delta-1 protein (r-delta1), human Delta-1 protein (h-delta1), a Xenopus Delta1 protein (x-delta1), a chicken Delta1 protein (c-delta1), a zebrafish Delta1 protein (z-delta1), a second Xenopus Delta protein (x-delta2), the human Delta3 protein (h-delta3), and a Drosophila Delta1 protein (d-delta1). The amino acid sequence of h-delta1 is the amino acid sequence published in PCT application WO 97/01571 which is incomplete and contains numerous errors, as stated in the application. Since the amino acid sequence alignment has been done using the pileup computer program (GCG Package), the order of the amino acid sequences in the figure reflects the homology between the different Delta proteins. Accordingly, the Drosophila protein, which corresponds to the bottom sequence in the alignment is most distant from the other Delta proteins. Thus, FIG. 2 shows that hDelta3, which is listed second last in FIG. 2, is the second most distant Delta protein from the previously identified mouse, rat, human, Xenopus, zebrafish, and chicken delta protein. Accordingly, hDelta3 protein is significantly different from the previously described human Delta protein, as well as the Delta proteins from the other species. Interestingly, the hDelta3 protein has an amino acid sequence which is equally distant from both Xenopus proteins, i.e., Delta1 and Delta2, indicating that hDelta3 does not correspond to either of the Xenopus Delta proteins. Therefore, the newly isolated polypeptide has been termed hDelta3 and the previously identified mouse, rat, human, zebrafish, and Xenopus Delta proteins are termed Delta1 proteins herein and the two Xenopus proteins are termed Delta1 and Delta2 proteins. The difference between hDelta3 protein and previously isolated Delta proteins can also be visualized by comparing the percentage homology or identity between hDelta3 and the previously identified Delta1 and Delta2 proteins on one hand (Table I), and the percent homology or identity of a Delta1 protein with the other Delta1 and Delta2 proteins (Table II).

TABLE I

Percentage similarity between the amino acid sequence of human Delta3 (SEQ ID No. 2) and that of the various Delta proteins

|  | GenBank Accession No. | % identity | % similarity |
| --- | --- | --- | --- |
| human Delta1 | N.A. | 50 | 66 |
| mouse Delta1 | X80903 | 53 | 70 |
| rat Delta1 | U78889 | 54 | 70 |
| chicken Delta1 | U26590 | 52 | 68 |
| Xenopus Delta1 | L42229 | 51 | 68 |
| zebrafish Delta1 | Y11760 | 48 | 67 |
| Xenopus Delta2 | U70843 | 47 | 65 |
| Drosophila Delta1 | AA142228 | 40 | 58 |
| hDelta-like (dlk) | U15979 | 33 | 55 |

Table II indicates the percent similarity and identity between human Delta1 disclosed in PCT Application PCT/US96/11178 (Publication No. WO 97/01571) and non-human Delta1 proteins. Since the amino acid sequence of the human Delta1 protein that is disclosed in this PCT application is incomplete, the percentage similarity and identity was determined using a portion of the human Delta1 amino acid sequence which seems most reliable. The portion of the amino acid sequence used corresponds to amino acids 214–370 of the human Delta1 amino acid sequence shown in FIG. 14A of the PCT application.

TABLE II

Percentage similarity between human Delta1 and the various non-human Delta1 or Delta2 proteins

| | GenBank Accession No. | % identity | % similarity |
|---|---|---|---|
| human Delta1 | N.A. | 100 | 100 |
| mouse Delta1 | X80903 | 86 | 95 |
| rat Delta1 | U78889 | 88 | 94 |
| chicken Delta1 | U26590 | 85 | 89 |
| Xenopus Delta1 | L42229 | 78 | 84 |
| zebrafish Delta1 | Y11760 | 69 | 80 |
| Xenopus Delta2 | U70843 | 57 | 70 |
| Drosophila Delta1 | AA142228 | 45 | 62 |
| hDelta-like (dlk) | U15979 | 37 | 55 |

Accordingly, Table I indicates that hDelta3 is only approximately 66% similar to the human Delta1 protein; approximately 70% similar to the mouse Delta1 protein; approximately 70% similar to the rat Delta1 protein; approximately 68% similar to the chick Delta1 protein; approximately 68% similar to the Xenopus Delta1 protein, approximately 70% similar to the Xenopus Delta2 protein and approximately 58% similar to the Drosophila Delta1 protein. However, as shown in Table II, the human-Delta1 protein is very similar to the mouse, rat, chick, Xenopus, zebrafish, and Drosophila Delta1 and the Xenopus Delta2 proteins. In addition, mouse and rat Delta1 proteins are about 95% similar. Thus, the amino acid sequence of Delta1 proteins share more homology with each other than with the human Delta3 protein of the invention, indicating that at least two families of Delta proteins exist.

The difference between the newly isolated hDelta3 protein and the previously identified Delta1 and Delta2 proteins can also be seen by creating a phylogenic tree using the Growtree Phylogram computer program (GCG Package). The result of this analysis, which is shown in FIG. 3, indicate that h-Delta3 is on a different "branch" in the phylogenic tree from the other Delta proteins, thus confirming that hDelta3 protein is more distant from the other Delta1 and Delta2 proteins than they are distant from each other. According to the analysis, and as predicted by the sequence alignment, only the Drosophila Delta protein is more distantly related to the previously identified mouse, rat, Xenopus, chicken, zebrafish and human Delta proteins than hDelta3. Thus, the newly isolated hDelta3 protein is a member of a different subspecies of the family of Delta proteins.

Notwithstanding that each animal species is likely to have at least two or three members (e.g. Delta1, Delta 2, and Delta3), it can be seen from FIG. 2, that the DSL region, the eight EGF repeats and the TM appear to be highly conserved throughout. However, as can be seen in FIG. 2, these domains of the hDelta3 protein differ more from the corresponding domains in the other Delta proteins than the corresponding domains in the other Delta differ from one another.

The DSL region or motif is shared by all known members of the family of presumed ligands of Notch-like proteins (Delta1 and Serrate in Drosophila; Lag-2 and Apx-1 in *Caenorhabditis elegans*) (Henderson et al. (1994) Development 120:2913; Tax et al. (1994) Nature 368:150; Fleming et al. (1990) Genes Dev. 4:2188; Thomas et al. (1991) Development 11:749; Mello et al. (1994) Cell 77:95). The DSL motif is located in the amino terminal portion of the protein which is closely related to a similar domain in the Drosophila Delta1 protein and which has been described as being necessary and sufficient for in vitro binding to Notch (Henrique et al. (1995) Nature 375:787; Muskavitch (1994) Dev. Biol. 166:415).

Furthermore, as set forth in Example, 5.5., Delta3 has been localized to human chromosome 15 in a region close to the framework markers D15S1244 and D15S144. Interestingly, the region on chromosome 15 that is flanked by the markers D15S1040 and D15S 118 has been shown to be genetically linked with the disease called Agenesis of the Corpus Callosum with Peripheral Neuropathy (ACCPN) (Casaubon et al., supra). No specific gene has so far been linked to this disease. Accordingly, since Delta3 is localized to a chromosomal region genetically linked to ACCPN and Delta3 is a member of the Notch signaling pathway, defects in which have been associated with a number of neurological diseases or conditions, Delta3 is likely to be the gene involved in ACCPN.

ACCPN, which is also termed Andermann syndrome (MIM 218000), is an autosomal recessive disorder that occurs with a high prevalence in the French Canadian population in the Charlevoix and Saguenay-Lac St Jean region in Quebec. The disease is characterized by a progressive peripheral neuropathy caused by axonal degeneration and a central nervous system (CNS) malformation characterized by the absence of hypoplasia of the corpus callosum. The disorder appears early in life, is progressive and results in death in the third decade of life of the subject.

Accordingly, certain aspects of the present invention relate to Delta3 proteins, nucleic acid molecules encoding Delta3 proteins, antibodies immunoreactive with Delta3 proteins, and preparations of such compositions. In addition, drug discovery assays are provided for identifying agents that modulate the biological function of Delta proteins, e.g., Delta3 proteins (i.e. agonists or antagonists), such as by binding to Delta3 or by altering the interaction of Delta3 with either downstream or upstream elements in the Delta/Notch signal transduction pathway by altering the interaction between Delta3 and a Delta3 binding protein. Such agents can be useful therapeutically, for example, to alter cell growth and/or differentiation or induction of apoptosis. Moreover, the present invention provides diagnostic and therapeutic assays and reagents for detecting and treating disorders involving an aberrant Delta3 activity, for example, aberrant expression (or loss thereof) of Delta3 gene or which are associated with a specific Delta allele, e.g., a Delta3 allele. Other aspects of the invention are described below or will be apparent to one of skill in the art in light of the present disclosure.

4.2 Definitions

For convenience, the meaning of certain terms and phrases employed in the specification, examples, and appended claims are provided below.

The term "allele", which is used interchangeably herein with "allelic variant" refers to alternative forms of a gene or portions thereof. Alleles occupy the same locus or position on homologous chromosomes. When a subject has two identical alleles of a gene, the subject is said to be homozygous for the gene or allele. When a subject has two different alleles of a gene, the subject is said to be heterozygous for the gene. Alleles of a specific gene can differ from each other in a single nucleotide, or several nucleotides, and can include substitutions, deletions, and insertions of nucleotides. An allele of a gene can also be a form of a gene containing a mutation.

The term "allelic variant of a polymorphic region of a Delta gene" refers to a region of a Delta gene having one of several nucleotide sequences found in that region of the gene in other individuals.

The term "agonist", as used herein, is meant to refer to an agent that upregulates (e.g. potentiates or supplements) a Delta3 bioactivity. A Delta3 agonist can be a compound that upregulates expression of a Delta3 gene. Alternatively, a Delta3 agonist can be a compound which increases signalling from a Delta3 protein, e.g., a compound bound to Delta3, such as a stimulatory form of a toporythmic protein or a small molecule. A Delta3 agonist can also be a compound which modulates the expression or activity of a protein which is located downstream of Delta3 or which interacts with Delta3.

"Antagonist" as used herein is meant to refer to an agent that downregulates (e.g. suppresses or inhibits) a Delta3 bioactivity. A Delta3 antagonist can be a compound that downregulates expression of a Delta3 gene. Alternatively, Delta3 antagonist can be a compound which decreases signalling from a Delta3 protein, e.g., a compound binding to Delta3 such as an inhibitory form of a toporythmic protein, or a small molecule. A preferred Delta3 antagonist inhibits the interaction between a Delta3 protein and another molecule, e.g., a toporythmic protein. A Delta3 antagonist can also be a compound which modulates the expression or activity of a protein which is located downstream of Delta3 or which interacts with Delta3.

"Biological activity" used interchangeably with the terms "bioactivity" or "activity" for the purposes herein means an effector or antigenic function that is directly or indirectly performed by a Delta3 polypeptide (whether in its native or denatured conformation), or by any subsequence thereof. Effector functions include receptor binding or activation, induction of differentiation, mitogenic or growth promoting activity, induction of apoptosis, signal transduction, immune modulation, DNA regulatory functions and the like, whether presently known or inherent. Antigenic functions include possession of an epitope or antigenic site that is capable of cross-reacting with antibodies raised against a naturally occurring or denatured Delta3 polypeptide or fragment thereof. Accordingly, a biological activity of a Delta3 protein can be binding to a receptor, such as Notch. A biological activity of a Delta3 protein can also be modulation of cell proliferation and/or differentiation, or cell death in a target cell having an appropriate receptor. A target cell can be, e.g., a neural cell, an endothelial cell, or a cancer cell.

Biologically active Delta3 polypeptides include polypeptides having both an effector and antigenic function, or only one of such functions. Delta3 includes antagonist polypeptides and native Delta3, provided that such antagonists include an epitope of a native Delta3 or antagonize a biologic activity of native Delta3.

The term "aberrant Delta3 activity" or "abnormal Delta3 activity" is intended to encompass an activity of Delta3 which differs from the same Delta3 activity in a healthy subject. An aberrant Delta3 activity can result, e.g., from a mutation in the protein, which results, e.g., in lower or higher binding affinity to a receptor. An aberrant Delta3 activity can also result from a lower or higher level of Delta3 on cells, which can result, e.g., from aberrant transcription, splicing, or translation of the Delta3 gene. For example, an aberrant Delta3 activity can result from an abnormal promoter activity. An aberrant Delta3 activity can also result from an aberrant signalling through the cytoplasmic domain of the Delta3 protein, such that, e.g., an aberrant signal is transduced. Aberrant signalling can result from a mutation in the cytoplasmic domain of Delta3 or, alternatively, from the contact with an abnormal cytoplasmic protein. An aberrant Delta3 activity can also result from contact of a Delta3 protein with an aberrant receptor, e.g., abnormal Notch protein.

"Cells," "host cells" or "recombinant host cells" are terms used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

A "chimeric protein" or "fusion protein" is a fusion of a first amino acid sequence encoding one of the subject Delta3 polypeptides with a second amino acid sequence defining a domain (e.g. polypeptide portion) foreign to and not substantially homologous with any domain of one of the Delta3 proteins. A chimeric protein may present a foreign domain which is found (albeit in a different protein) in an organism which also expresses the first protein, or it may be an "interspecies", "intergenic", e.g. fusion of protein structures expressed by different kinds of organisms. In general, a fusion protein can be represented by the general formula X-Delta3-Y, wherein Delta3 represents a portion of the protein which is derived from one of the Delta3 proteins, and X and Y are independently absent or represent amino acid sequences which are not related to one of the Delta3 sequences in an organism, including naturally occurring mutants. A preferred Delta3 fusion protein is a Delta3-Ig fusion protein.

"Complementary" sequences as used herein refer to sequences which have sufficient complementarity to be able to hybridize, forming a stable duplex.

A "delivery complex" shall mean a targeting means (e.g. a molecule that results in higher affinity binding of a gene, protein, polypeptide or peptide to a target cell surface and/or increased cellular uptake by a target cell). Examples of targeting means include: sterols (e.g. cholesterol), lipids (e.g. a cationic lipid, virosome or liposome), viruses (e.g. adenovirus, adeno-associated virus, and retrovirus) or target cell specific binding agents (e.g. ligands recognized by target cell specific receptors). Preferred complexes are sufficiently stable in vivo to prevent significant uncoupling prior to internalization by the target cell. However, the complex is cleavable under appropriate conditions within the cell so that the gene, protein, polypeptide or peptide is released in a functional form.

As is well known, genes for a particular polypeptide may exist in single or multiple copies within the genome of an individual. Such duplicate genes may be identical or may have certain modifications, including nucleotide substitutions, additions or deletions, which all still code for polypeptides having substantially the same activity. The term "DNA sequence encoding a Delta3 polypeptide" may thus refer to one or more genes within a particular individual. Moreover, certain differences in nucleotide sequences may exist between individual organisms, which are called alleles. Such allelic differences may or may not result in differences in amino acid sequence of the encoded polypeptide yet still encode a protein with the same biological activity.

The term "Delta3 therapeutic" refers to various compositions of Delta3 polypeptides, as well as peptidomimetics, small molecules and nucleic acids which are capable of mimicking or potentiating (agonizing) or inhibiting (antagonizing) the effects of a naturally-occurring Delta3 protein. A Delta3 therapeutic which mimics or potentiates the activity of a wild-type Delta3 protein is a "Delta3 agonist". Conversely, a Delta3 therapeutic which inhibits the activity of a wild-type Delta3 protein is a "Delta3 antagonist".

The terms "Delta3 polypeptide" and "Delta3 protein" are intended to encompass Delta3 polypeptides which have at least one biological activity, i.e., antagonizing at least one biological activity of a native Delta3 polypeptide.

As used herein, the term "gene" or "recombinant gene", as applied to Delta3, refers to a nucleic acid molecule comprising an open reading frame encoding one of the Delta3 polypeptides of the present invention, including both exon and (optionally) intron sequences. A "recombinant Delta3 gene" refers to nucleic acid encoding a Delta3 polypeptide and comprising Delta-encoding exon sequences, though it may optionally include intron sequences which are either derived from a chromosomal Delta3 gene or from an unrelated chromosomal gene. Exemplary recombinant genes encoding the subject Delta3 polypeptides are represented in the appended Sequence Listing. The term "intron" refers to a DNA sequence present in a given Delta3 gene which is not translated into protein and is generally found between exons.

The term "growth state" of a cell refers to the proliferative state of a cell as well as to its differentiative state. Accordingly, the term refers to the phase of the cell cycle in which the cell is, e.g., G0, G1, G2, prophase, metaphase, or telophase, as well as to its state of differentiation, e.g., undiffereniated, partially differentiated, or fully differentiated. Without wanting to be limited, differentiation of a cell is usually accompanied by a decrease in the proliferative rate of a cell.

"Homology" or "identity" or "similarity" refers to sequence similarity between two peptides or between two nucleic acid molecules. Homology can be determined by comparing a position in each sequence which may be aligned for purposes of comparison. When a position in the compared sequence is occupied by the same base or amino acid, then the molecules are identical at that position. A degree of homology or similarity or identity between nucleic acid sequences is a function of the number of identical or matching nucleotides at positions shared by the nucleic acid sequences. A degree of identity of amino acid sequences is a function of the number of identical amino acids at positions shared by the amino acid sequences. A degree of homology or similarity of amino acid sequences is a function of the number of conserved amino acids at positions shared by the amino acid sequences. A sequence which is "unrelated" or "non-homologous" with one of the hDelta3 sequences of the present invention is a sequence which shares less than 40% identity, though preferably less than 25% identity with one of the hDelta3 sequences of the present invention.

The term "interact" as used herein is meant to include detectable interactions between molecules, such as can be detected using, for example, a yeast two hybrid assay. The term interact is also meant to include "binding" interactions between molecules. Interactions may be protein-protein, protein-nucleic acid, protein-small molecule, or nucleic acid-small molecule in nature.

The term "isolated" as used herein with respect to nucleic acids, such as DNA or RNA, refers to molecules separated from other DNAs, or RNAs, respectively, that are present in the natural source of the macromolecule. For example, an isolated nucleic acid encoding one of the subject Delta3 polypeptides preferably includes no more than 10 kilobases (kb) of nucleic acid sequence which naturally immediately flanks the Delta3 gene in genomic DNA, more preferably no more than 5 kb of such naturally occurring flanking sequences, and most preferably less than 1.5 kb of such naturally occurring flanking sequence. The term isolated as used herein also refers to a nucleic acid or peptide that is substantially free of cellular material, viral material, or culture medium when produced by recombinant DNA techniques, or chemical precursors or other chemicals when chemically synthesized. Moreover, an "isolated nucleic acid" is meant to include nucleic acid fragments which are not naturally occurring as fragments and would not be found in the natural state. The term "isolated" is also used herein to refer to polypeptides which are isolated from other cellular proteins and is meant to encompass both purified and recombinant polypeptides.

The term "modulation" as used herein refers to both upregulation, i.e., stimulation, and downregulation, i.e. suppression, of a response.

The term "mutated gene" refers to an allelic form of a gene, which is capable of altering the phenotype of a subject having the mutated gene relative to a subject which does not have the mutated gene. If a subject must be homozygous for this mutation to have an altered phenotype, the mutation is said to be recessive. If one copy of the mutated gene is sufficient to alter the genotype of the subject, the mutation is said to be dominant. If a subject has one copy of the mutated gene and has a phenotype that is intermediate between that of a homozygous and that of a heterozygous (for that gene) subject, the mutation is said to be co-dominant.

The "non-human animals" of the invention include mammalians such as rodents, non-human primates, sheep, dog, cow, chickens, amphibians, reptiles, etc. Preferred non-human animals are selected from the rodent family including rat and mouse, most preferably mouse, though transgenic amphibians, such as members of the Xenopus genus, and transgenic chickens can also provide important tools for understanding and identifying agents which can affect, for example, embryogenesis and tissue formation. The term "chimeric animal" is used herein to refer to animals in which the recombinant gene is found, or in which the recombinant is expressed in some but not all cells of the animal. The term "tissue-specific chimeric animal" indicates that one of the recombinant Delta3 genes is present and/or expressed or disrupted in some tissues but not others.

As used herein, the term "nucleic acid" refers to polynucleotides such as deoxyribonucleic acid (DNA), and, where appropriate, ribonucleic acid (RNA). The term should also be understood to include, as equivalents, analogs of either RNA or DNA made from nucleotide analogs, and, as applicable to the embodiment being described, single (sense or antisense) and double-stranded polynucleotides.

The term "polymorphism" refers to the coexistence of more than one form of a gene or portion thereof. A portion of a gene of which there are at least two different forms, i.e., two different nucleotide sequences, is referred to as a "polymorphic region of a gene". A polymorphic region can be a single nucleotide, the identity of which differs in different alleles. A polymorphic region can also be several nucleotides long.

A "polymorphic gene" refers to a gene having at least one polymorphic region.

The terms "protein", "polypeptide" and "peptide" are used interchangably herein when referring to a gene product.

The term "recombinant protein" refers to a polypeptide of the present invention which is produced by recombinant DNA techniques, wherein generally, DNA encoding a Delta3 polypeptide is inserted into a suitable expression vector which is in turn used to transform a host cell to produce the heterologous protein. Moreover, the phrase "derived from", with respect to a recombinant Delta3 gene, is meant to include within the meaning of "recombinant protein" those proteins having an amino acid sequence of a native Delta3 protein, or an amino acid sequence similar thereto which is generated by mutations including substitutions and deletions (including truncation) of a naturally occurring form of the protein.

As used herein, the term "specifically hybridizes" or "specifically detects" refers to the ability of a nucleic acid molecule of the invention to hybridize to at least approximately 6, 12, 20, 30, 50, 100, 150, 200, 300, 350, 400 or 425 consecutive nucleotides of a vertebrate, preferably mammalian, Delta3 gene, such as a Delta3 sequence designated in one of SEQ ID Nos: 1 or 3, or a sequence complementary thereto, or naturally occurring mutants thereof, such that it shows more than 10 times more hybridization, preferably more than 100 times more hybridization, and even more preferably more than 100 times more hybridization than it does to a cellular nucleic acid (e.g., mRNA or genomic DNA) encoding a protein other than a vertebrate, preferably Delta3 protein as defined herein.

As used herein, the term "tissue-specific promoter" means a DNA sequence that serves as a promoter, i.e., regulates expression of a selected DNA sequence operably linked to the promoter, and which effects expression of the selected DNA sequence in specific cells of a tissue, such as cells of hepatic or pancreatic origin, neuronal cells, or immune cells. The term also covers so-called "leaky" promoters, which regulate expression of a selected DNA primarily in one tissue, but cause expression in other tissues as well.

"Transcriptional regulatory sequence" is a generic term used throughout the specification to refer to DNA sequences, such as initiation signals, enhancers, and promoters, which induce or control transcription of protein coding sequences with which they are operably linked. In preferred embodiments, transcription of one of the recombinant Delta3 genes is under the control of a promoter sequence (or other transcriptional regulatory sequence) which controls the expression of the recombinant gene in a cell-type in which expression is intended. It will also be understood that the recombinant gene can be under the control of transcriptional regulatory sequences which are the same or which are different from those sequences which control transcription of the naturally-occurring forms of Delta3 proteins.

As used herein, the term "transfection" means the introduction of a nucleic acid, e.g., an expression vector, into a recipient cell by nucleic acid-mediated gene transfer. "Transformation", as used herein, refers to a process in which a cell's genotype is changed as a result of the cellular uptake of exogenous DNA or RNA, and, for example, the transformed cell expresses a recombinant form of a Delta3 polypeptide or, in the case of anti-sense expression from the transferred gene, the expression of a naturally-occurring form of the Delta3 protein is disrupted.

As used herein, the term "transgene" means a nucleic acid sequence (encoding, e.g., one of the Delta3 polypeptides, or an antisense transcript thereto), which is partly or entirely heterologous, i.e., foreign, to the transgenic animal or cell into which it is introduced, or, is homologous to an endogenous gene of the transgenic animal or cell into which it is introduced, but which is designed to be inserted, or is inserted, into the animal's genome in such a way as to alter the genome of the cell into which it is inserted (e.g., it is inserted at a location which differs from that of the natural gene or its insertion results in a knockout). A transgene can include one or more transcriptional regulatory sequences and any other nucleic acid, such as introns, that may be necessary for optimal expression of a selected nucleic acid.

A "transgenic animal" refers to any animal, preferably a non-human mammal, bird or an amphibian, in which one or more of the cells of the animal contain heterologous nucleic acid introduced by way of human intervention, such as by transgenic techniques well known in the art. The nucleic acid is introduced into the cell, directly or indirectly by introduction into a precursor of the cell, by way of deliberate genetic manipulation, such as by microinjection or by infection with a recombinant virus. The term genetic manipulation does not include classical cross-breeding, or in vitro fertilization, but rather is directed to the introduction of a recombinant DNA molecule. This molecule may be integrated within a chromosome, or it may be extrachromosomally replicating DNA. In the typical transgenic animals described herein, the transgene causes cells to express a recombinant form of one of the Delta3 proteins, e.g. either agonistic or antagonistic forms. However, transgenic animals in which the recombinant Delta3 gene is silent are also contemplated, as for example, the FLP or CRE recombinase dependent constructs described below. Moreover, "transgenic animal" also includes those recombinant animals in which gene disruption of one or more Delta3 genes is caused by human intervention, including both recombination and antisense techniques.

As used herein, the term "vector" refers to a nucleic acid molecule capable of transporting another nucleic acid to which it has been linked. One type of preferred vector is an episome, i.e., a nucleic acid capable of extra-chromosomal replication. Preferred vectors are those capable of autonomous replication and/expression of nucleic acids to which they are linked. Vectors capable of directing the expression of genes to which they are operatively linked are referred to herein as "expression vectors". In general, expression vectors of utility in recombinant DNA techniques are often in the form of "plasmids" which refer generally to circular double stranded DNA loops which, in their vector form are not bound to the chromosome. In the present specification, "plasmid" and "vector" are used interchangeably as the plasmid is the most commonly used form of vector. However, the invention is intended to include such other forms of expression vectors which serve equivalent functions and which become known in the art subsequently hereto.

The term "treating" as used herein is intended to encompass curing as well as ameliorating at least one symptom of the condition or disease.

4.3 Nucleic Acids of the Present Invention

As described below, one aspect of the invention pertains to isolated nucleic acids comprising nucleotide sequences encoding Delta3 polypeptides, and/or equivalents of such polypeptides or nucleic acids. The term equivalent is understood to include nucleotide sequences encoding functionally equivalent Delta3 polypeptides or functionally equivalent peptides having an activity of a Delta3 protein such as described herein. Equivalent nucleotide sequences will include sequences that differ by one or more nucleotide substitutions, additions or deletions, such as allelic variants; and will, therefore, include sequences that differ from the nucleotide sequence of the Delta3 gene shown in any of SEQ ID Nos: 1 or 3 due to the degeneracy of the genetic code.

Preferred Delta3 nucleic acids encode polypeptides that are at least 55% identical or similar to an amino acid sequence of SEQ ID No. 2. Nucleic acids which encode polypeptides which are at least about 70%, and even more preferably at least about 80%, 85%, 90%, 95%, or 98% identical or similar with an amino acid sequence represented in SEQ ID No: 2 are also within the scope of the invention.

In a particularly preferred embodiment, the nucleic acid of the present invention encodes a polypeptide having an overall amino acid sequence homology or identity of at least about 70%, at least about 80%, at least about 85%, at least about 90%, at least about 95%, at least about 98%, or at least about 99% with the amino acid sequence shown in SEQ ID No: 2. In a preferred embodiment, the nucleic acid encodes a protein comprising the amino acid set forth in SEQ ID No. 2. Preferably, the nucleic acid includes all or a portion of the nucleotide sequence corresponding to the coding region of SEQ ID Nos: 1 or 3.

The nucleic acids of the invention can encode a Delta3 protein from any species, including insects. Preferred nucleic acids encode vertebrate Delta3 proteins. Even more preferred nucleic acids encode primate Delta3 proteins including mammalian Delta3 proteins, e.g., human Delta3 proteins. Other nucleic acids of the invention can encode avian, equine, canine, feline, bovine or porcine Delta3 proteins.

In a preferred embodiment of the invention, the nucleic acid encodes a polypeptide comprising an extracellular domain of Delta3, e.g., Delta3 having SEQ ID No. 2. Accordingly, preferred nucleic acids encode a polypeptide comprising about amino acid 1 to about amino acid 529 or SEQ ID No. 2. Other preferred nucleic acids encode a polypeptide corresponding to an extracellular domain of Delta3 essentially lacking the signal peptide, e.g., a polypeptide comprising about amino acid 18 to about amino acid 529 of SEQ ID No. 2. Yet other preferred nucleic acids encode a polypeptide comprising at least one of the conserved motifs in the extracellular domain of Delta3, e.g., a DSL motif or an EGF-like motif, such as those shown in FIG. 2 (SEQ ID No. 2). In one embodiment, the nucleic acid encodes a protein having at least one EGF-like motif. In other embodiments, the nucleic acid encodes proteins having at least 2, at least 3, at least 4, at least 5, at least 6, at least 7, or 8 EGF-like repeats, such as those shown in FIG. 2 (SEQ ID No.2). The polypeptide encoded by a nucleic acid encoding any of these numbers of EGF-like repeats can further comprise an amino acid sequence encoding a DSL motif.

Polypeptides encoded by any of the above-described nucleic acids can be soluble. Preferred soluble peptides comprise at least a portion of the extracellular domain of a Delta3 protein. Even more preferred soluble polypeptides comprise an amino acid sequence corresponding to about amino acid 1 to about amino acid 529 of SEQ ID No. 2 or homolog thereof. Yet other preferred soluble Delta3 polypeptides comprise at least one EGF-like repeat. Such polypeptides may in addition comprise a DSL domain and optionally a signal peptide.

Even more preferred nucleic acids encode a Delta3 polypeptide which is a fusion protein. A preferred fusion protein is a Delta3-Ig fusion protein. Such fusion proteins can comprise at least a portion of the extracellular domain of a Delta3 domain. A portion can be any portion of at least about 10 amino acids, such as the portions described above. Nucleic acids encoding such fusion proteins can be prepared as described in U.S. Pat. No. 5,434,131.

Alternatively, polypeptides encoded by the nucleic acid of the invention can be membrane bound. Membrane bound polypeptides of the invention preferably comprise a transmembrane domain. The transmembrane domain can be from a Delta3 protein, such as a transmembrane domain comprising about amino acid 530 to about amino acid 553 of SEQ ID No. 2, shown in FIG. 2. Alternatively, the transmembrane domain can be from another membrane protein, such as to produce a chimeric membraneous Delta3 protein. Yet other polypeptides of the invention can be intracellular proteins. Accordingly, also within the scope of the invention are proteins which do not comprise a transmembrane domain. Other proteins of the invention do not include an extracellular domain. Additional proteins of the invention do not include an extracellular domain nor a transmembrane domain.

Polypeptides encoded by the nucleic acid of the invention can comprise a cytoplasmic domain. In a preferred embodiment, a nucleic acid of the invention encodes a polypeptide comprising a Delta3 cytoplasmic domain. In an even more preferred embodiment, the cytoplasmic domain has an amino acid sequence corresponding to a sequence from about amino acid 554 to about amino acid 685 of SEQ ID No. 2 (FIG. 2), or a portion thereof.

In yet other preferred embodiments, the nucleic acid of the invention encodes a polypeptide comprising at least one domain of a Delta3 protein selected from the group consisting of: a signal peptide, a DSL motif, an EGF-like repeat, a transmembrane domain, and a cytoplamic domain. The polypeptide of the invention can comprise several of these domains from a Delta3 protein. Alternatively, a polypeptide of the invention can be a chimeric protein, i.e., comprising several of these conserved domains, at least some of which are derived from a protein other than a Delta3 protein. Accordingly, in one embodiment, a nucleic acid of the invention encodes a polypeptide having a DSL motif having an amino acid sequence from a Delta3 protein other than Delta3. Such an amino acid sequence can be any sequence shown in FIG. 2 as being a DSL motif. In yet another embodiment, the nucleic acid encodes a Delta3 protein having a signal peptide from a protein other than a Delta3 protein. Also within the scope of the invention are nucleic acids encoding a Delta3 polypeptide having a cytoplasmic domain from a protein other than a Delta3 protein and nucleic acids encoding a Delta3 cytoplasmic domain and a extracellular domain from a protein other than a Delta3 protein. Proteins other than Delta3 proteins can be, e.g., toporythmic proteins. "Toporythmic proteins" is intended to include Notch, Delta, Serrate, Enhancer of Split, Deltex, and other members of this family of proteins sharing structural similarities. (See e.g. International Patent Application Nos. WO 97/01571; WO 92/19734 and WO 92/19734 and WO 94/07474, supra).

Nucleic acids encoding polypeptides having an amino acid sequence that is homologous to any of the above described portions of SEQ ID No. 2 are also within the scope of the invention. Preferred nucleic acids of the invention encode polypeptides comprising an amino acid sequence which is at least about 70%, at least about 75%, at least about 80%, or at least about 85% homologous or identical to the amino acid sequence of any of the Delta3 domains shown in FIG. 2. Even more preferred nucleic acids of the invention encode polypeptides comprising an amino acid sequence which is at least about 90%, at least about 95%, at least about 98%, or at least about 99% homologous or identical to the amino acid sequence of any of the Delta3 domains shown in FIG. 2.

In one embodiment, the nucleic acid, e.g., cDNA, encodes a peptide having at least one bioactivity of the subject Delta3 polypeptide, such as the ability to bind to a Delta3 receptor, e.g., Notch. Proteins or peptides capable of interacting with a Delta3 protein or fragment thereof can be identified by various methods, e.g., methods based on binding assays. For example, various types of expression libraries can be screened with a Delta3 protein or portion thereof. A 2-hybrid system can be used to isolate cytoplasmic proteins interacting with the cytoplasmic domain of Delta3. Portions of Delta3 proteins which are capable of interacting with a ligand can be determined by preparing fragments of Delta3 proteins and screening these fragments for those that are capable of interacting with the ligand. Based at least in part on the observation that the N-terminal portion of Drosophila Delta protein, which contains a DSL domain and EGF-like domain, is necessary and sufficient for in vitro binding to Notch (Henrique et al., supra; Muskavitch et al., supra), it is likely that the domain of Delta3 proteins capable of interacting with a ligand includes the DSL domain and/or at least a portion of the EGF-like domain. However, other portions of the extracellular domain of Delta3 could be necessary for binding to at least some Delta3 ligands.

In other preferred embodiments, the subject Delta3 polypeptide can modulate proliferation and/or differentiation or cell death of specific target cells, e.g., neural cells or endothelial cells. Assays for determining that a Delta3 polypeptide has at least one bioactivity of a Delta3 protein are described infra.

Still other preferred nucleic acids of the present invention encode a Delta3 polypeptide which includes a polypeptide sequence corresponding to all or a portion of amino acid residues of SEQ ID No: 2, e.g., at least 2, 5, 10, 25, 50, 100, 150 or 200 amino acid residues of that region. Preferred nucleic acids encode a polypeptide comprising at least two consecutive amino acid residues from about amino acid 1 to about amino acid 570 of the amino acid sequence set forth in SEQ ID No. 2. Yet other preferred nucleic acids encode a polypeptide comprising at least about 3, at least about 5, at least about 10, at least about 15, at least about 20, or at least about 25 consecutive amino acids from about amino acid 1 to about amino acid 575 set forth in SEQ ID No. 2. The invention further provides for nucleic acids encoding a polypeptide having an amino acid sequence which is at least about 70%, preferably at least about 80%, and most preferably at least about 90% to at least about 10 consecutive amino acids set forth in SEQ ID No. 2, or at least about 10 consecutive amino acids from a portion of SEQ ID No. 2. In one embodiment, the portion corresponds to about amino acid 1 to about amino acid 575 of SEQ ID No. 2. Coding nucleic acid molecules of the invention preferably comprise at least about 200, 250, 300, 350, 400, 410, 420, 430, 435 or 440 base pairs.

The invention further pertains to nucleic acid molecules for use as probes/primer or antisense molecules (i.e. non-coding nucleic acid molecules), which can comprise at least about 6, 12, 20, 30, 50, 100, 125, 150 or 200 nucleotides or base pairs. Yet other preferred nucleic acids of the invention comprise at least about 300, at least about 350, at least about 400, at least about 450, at least about 500, or at least about 600 nucleotides of SEQ ID No.1 or 3. In some embodiments, the nucleic acids of the invention correspond to a 5' portion of nucleic acid sequence SEQ ID No. 1. For example, a nucleic acid of the invention can correspond to a portion of about nucleotide 1 to about nucleotide 2000 of nucleic acid sequence SEQ ID No. 1.

Preferred nucleic acids for use as a probe according to the methods of the invention include nucleic acids comprising a nucleotide sequence having at least about 6, preferably at least about 9, more preferably at least about 12 and even more preferably at least about 15 consecutive nucleotides from SEQ ID No. 1 or from a portion thereof. In a preferred embodiment, the portion corresponds to about nucleotide 1 to about nucleotide 2060 of SEQ ID No. 1. Alternatively a portion can be a nucleotide sequence encoding a conserved motif of hDelta3 protein. Alternatively, the portion can be a nucleotide sequence located between nucleic acid sequences encoding conserved motifs of hDelta3 protein.

The invention further provides for a combination of at least two nucleic acids corresponding to at least a portion of SEQ ID No. 1 or a homolog thereof. Accordingly, in one embodiment, the invention provides a combination of two nucleic acids of at least about 6, preferably at least about 9, more preferably at least about 12 and even more preferably at least about 15 consecutive nucleotides from SEQ ID No. 1 or from a portion thereof. In a preferred embodiment, at least one of the nucleic acids is labeled.

Another aspect of the invention provides a nucleic acid which hybridizes under stringent conditions to a nucleic acid represented by one of SEQ ID Nos:1 or 3. Appropriate stringency conditions which promote DNA hybridization, for example, 6.0× sodium chloride/sodium citrate (SSC) at about 45° C., followed by a wash of 2.0× SSC at 50° C., are known to those skilled in the art or can be found in Current Protocols in Molecular Biology, John Wiley & Sons, N.Y. (1989), 6.3.1–6.3.6. For example, the salt concentration in the wash step can be selected from a low stringency of about 2.0× SSC at 50° C. to a high stringency of about 0.2× SSC at 50° C. or at 65° C. In addition, the temperature in the wash step can be increased from low stringency conditions at room temperature, about 22° C., to high stringency conditions at about 65° C. Both temperature and salt may be varied, or temperature of salt concentration may be held constant while the other variable is changed. In a preferred embodiment, a Delta3 nucleic acid of the present invention will bind to one of SEQ ID Nos 1 or 3 under moderately stringent conditions, for example at about 2.0× SSC and about 40° C. In a particularly preferred embodiment, a Delta3 nucleic acid of the present invention will bind to one of SEQ ID Nos: 1 or 3 under high stringency conditions.

Preferred nucleic acids have a sequence at least about 75% homologous and more preferably at least about 80% and even more preferably at least about 85% homologous with a nucleic acid sequence of a Delta3 gene, such as human Delta3 gene, e.g., such as a sequence shown in one of SEQ ID Nos: 1 and 3. Nucleic acids at least about 90%, more preferably at least about 95%, and most preferably at least about 98–99% homologous with a nucleic sequence represented in one of SEQ ID Nos: 1 and 3 are of course also within the scope of the invention. In preferred embodiments, the nucleic acid is a human Delta3 gene and in particularly preferred embodiments, includes all or a portion of the nucleotide sequence corresponding to the coding region of one of SEQ ID Nos: 1 or 3.

Nucleic acids having a sequence that differs from the nucleotide sequences shown in one of SEQ ID Nos: 1 or 3 due to degeneracy in the genetic code are also within the scope of the invention. Such nucleic acids encode functionally equivalent peptides (i.e., a peptide having a biological activity of a Delta3 polypeptide) but differ in sequence from the sequence shown in the sequence listing due to degeneracy in the genetic code. For example, a number of amino acids are designated by more than one triplet. Codons that specify the same amino acid, or synonyms (for example, CAU and CAC each encode histidine) may result in "silent" mutations which do not affect the amino acid sequence of a Delta3 polypeptide. However, it is expected that DNA sequence polymorphisms that do lead to changes in the amino acid sequences of the subject Delta3 polypeptides will exist. One skilled in the art will appreciate that these variations in one or more nucleotides (e.g., up to about 3–5% of the nucleotides) of the nucleic acids encoding polypeptides having an activity of a Delta3 polypeptide may exist among individuals of a given species due to natural allelic variation.

As indicated by the examples set out below, Delta3 protein-encoding nucleic acids can be obtained from mRNA present in any of a number of eukaryotic cells. It should also be possible to obtain nucleic acids encoding Delta3 polypeptides of the present invention from genomic DNA from both adults and embryos. For example, a gene encoding a Delta3 protein can be cloned from either a cDNA or a genomic library in accordance with protocols described herein, as well as those generally known to persons skilled in the art. Examples of tissues and/or libraries suitable for isolation of the subject nucleic acids include endothelial cell libraries, among others. A cDNA encoding a Delta3 protein can be obtained by isolating total mRNA from a cell, e.g. a vertebrate cell, a mammalian cell, or a human cell, including embryonic cells. Double stranded cDNAs can then be prepared from the total mRNA, and subsequently inserted into a suitable plasmid or bacteriophage vector using any one of a number of known techniques. The gene encoding a Delta3 protein can also be cloned using established polymerase chain reaction techniques in accordance with the nucleotide sequence information provided by the invention. The nucleic acid of the invention can be DNA or RNA. A preferred nucleic acid is a cDNA represented by a sequence selected from the group consisting of SEQ ID Nos: 1 and 3.

4.3.1. Vectors.

This invention also provides expression vectors containing a nucleic acid encoding a Delta3 polypeptide, operably linked to at least one transcriptional regulatory sequence. "Operably linked" is intended to mean that the nucleotide sequence is linked to a regulatory sequence in a manner which allows expression of the nucleotide sequence. Regulatory sequences are art-recognized and are selected to direct expression of the subject Delta3 proteins. Accordingly, the term "transcriptional regulatory sequence" includes promoters, enhancers and other expression control elements. Such regulatory sequences are described in Goeddel; Gene Expression Technology: Methods in Enzymology 185, Academic Press, San Diego, Calif. (1990). In one embodiment, the expression vector includes a recombinant gene encoding a peptide having an agonistic activity of a subject Delta3 polypeptide, or alternatively, encoding a peptide which is an antagonistic form of the Delta3 protein. Such expression vectors can be used to transfect cells and thereby produce polypeptides, including fusion proteins, encoded by nucleic acids as described herein. Moreover, the gene constructs of the present invention can also be used as a part of a gene therapy protocol to deliver nucleic acids encoding either an agonistic or antagonistic form of one of the subject Delta3 proteins. Thus, another aspect of the invention features expression vectors for in vivo or in vitro transfection and expression of a Delta3 polypeptide in particular cell types so as to reconstitute the function of, or alternatively, abrogate the function of Delta-induced signaling in a tissue. This could be desirable, for example, when the naturally-occurring form of the protein is misexpressed; or to deliver a form of the protein which alters differentiation of tissue. Expression vectors may also be employed to inhibit neoplastic transformation.

In addition to viral transfer methods, such as those illustrated above, non-viral methods can also be employed to cause expression of a subject Delta3 polypeptide in the tissue of an animal. Most nonviral methods of gene transfer rely on normal mechanisms used by mammalian cells for the uptake and intracellular transport of macromolecules. In preferred embodiments, non-viral targeting means of the present invention rely on endocytic pathways for the uptake of the subject Delta3 polypeptide gene by the targeted cell. Exemplary targeting means of this type include liposomal derived systems, poly-lysine conjugates, and artificial viral envelopes.

4.3.2. Probes and Primers

Moreover, the nucleotide sequences determined from the cloning of hDelta3 genes will further allow for the generation of probes and primers designed for use in identifying and/or cloning Delta3 homologs in other cell types, e.g. from other tissues, as well as Delta3 homologs from other mammalian organisms. Probes and primers of the invention can also be used to determine the identity of a Delta3 allele and/or the presence or absence of one or more mutations in a Delta3 gene of a subject. In a preferred embodiment, a probe or primer of the invention can be used to determine whether a subject has or is at risk of developing a disease or condition associated with a specific Delta3 allele, such as an allele carrying a mutation.

In a preferred embodiment, the present invention also provides a probe/primer comprising a substantially purified oligonucleotide, which oligonucleotide comprises a region of nucleotide sequence that hybridizes under stringent conditions to at least about 12, preferably about 25, more preferably about 40, 50 or 75 consecutive nucleotides of sense or anti-sense sequence selected from the group consisting of SEQ ID No: 1 and 3, or naturally occurring mutants thereof. For instance, primers based on the nucleic acid represented in SEQ ID Nos: 1 and 3 can be used in PCR reactions to clone Delta3 homologs, e.g. specific Delta3 alleles. Such primers are preferably selected in a region which does not share significant homology to other genes, e.g., other Delta genes. Preferred primers of the invention are set forth as SEQ ID Nos. 4–8 set forth below:

```
5' end primers:

5' AGCGCCTCTGGCTGGGCGCT 3' (SEQ ID No. 12; corresponding to nucleotides
                                356 to 375 of SEQ ID No. 1);
5' CGGCCAGAGGCCTTGCCACC 3' (SEQ ID No. 13; corresponding to nucleotides
                                725 to 744 of SEQ ID No. 1);
3' end primers:

5' TTGCGCTCCCGGCTGGAGCC 3' (SEQ ID No. 14; corresponding to the
                                complement of nucleotides 1460 to 1479 of
                                SEQ ID No. 1); and
5' ATGCGGCTTGGACCTCGGTT 3' (SEQ ID No. 15; corresponding to the
                                complement of nucleotides 1592 to 2611 of
                                SEQ ID No. 1).
```

Likewise, probes based on the subject Delta3 sequences can be used to detect transcripts or genomic sequences encoding the same or homologous proteins. In preferred embodiments, the probe further comprises a label group attached thereto and able to be detected, e.g. the label group is selected from amongst radioisotopes, fluorescent compounds, enzymes, and enzyme co-factors.

As discussed in more detail below, such probes can also be used as a part of a diagnostic test kit for identifying cells or tissue which misexpress a Delta3 protein, such as by measuring a level of a Delta-encoding nucleic acid in a sample of cells from a patient; e.g. detecting Delta3 mRNA levels or determining whether a genomic Delta3 gene has been mutated or deleted. Briefly, nucleotide probes can be generated from the subject Delta3 genes which facilitate histological screening of intact tissue and tissue samples for the presence (or absence) of Delta-encoding transcripts. Similar to the diagnostic uses of anti-Delta3 antibodies, the use of probes directed to Delta3 messages, or to genomic Delta3 sequences, can be used for both predictive and therapeutic evaluation of allelic mutations which might be manifest in, for example, neoplastic or hyperplastic disorders (e.g. unwanted cell growth) or abnormal differentiation of tissue. Used in conjunction with immunoassays as described herein, the oligonucleotide probes can help facilitate the determination of the molecular basis for a developmental disorder which may involve some abnormality associated with expression (or lack thereof) of a Delta3 protein. For instance, variation in polypeptide synthesis can be differentiated from a mutation in a coding sequence.

Also within the scope of the invention are kits for determining whether a subject is at risk of developing a disease or condition caused by or contributed by an aberrant Delta3 bioactivity and/or which is associated with one or more specific Delta3 alleles. In a preferred embodiment, the kit can be used for determining whether a subject is at risk of developing a neurological disease or disorder, e.g., a peripheral neuropathy, e.g., ACCPN.

4.3.3. Antisense, Ribozyme and Triplex techniques

One aspect of the invention relates to the use of the isolated nucleic acid in "antisense" therapy. As used herein, "antisense" therapy refers to administration or in situ generation of oligonucleotide molecules or their derivatives which specifically hybridize (e.g. bind) under cellular conditions, with the cellular mRNA and/or genomic DNA encoding one or more of the subject Delta3 proteins so as to inhibit expression of that protein, e.g. by inhibiting transcription and/or translation. The binding may be by conventional base pair complementarity, or, for example, in the case of binding to DNA duplexes, through specific interactions in the major groove of the double helix. In general, "antisense" therapy refers to the range of techniques generally employed in the art, and includes any therapy which relies on specific binding to oligonucleotide sequences.

An antisense construct of the present invention can be delivered, for example, as an expression plasmid which, when transcribed in the cell, produces RNA which is complementary to at least a unique portion of the cellular mRNA which encodes a Delta3 protein. Alternatively, the antisense construct is an oligonucleotide probe which is generated ex vivo and which, when introduced into the cell causes inhibition of expression by hybridizing with the mRNA and/or genomic sequences of a Delta3 gene. Such oligonucleotide probes are preferably modified oligonucleotides which are resistant to endogenous nucleases, e.g. exonucleases and/or endonucleases, and are therefore stable in vivo. Exemplary nucleic acid molecules for use as antisense oligonucleotides are phosphoramidate, phosphothioate and methylphosphonate analogs of DNA (see also U.S. Pat. Nos. 5,176,996; 5,264,564; and 5,256,775). Additionally, general approaches to constructing oligomers useful in antisense therapy have been reviewed, for example, by Van der Krol et al. (1988) Biotechniques 6:958–976; and Stein et al. (1988) Cancer Res 48:2659–2668. With respect to antisense DNA, oligodeoxyribonucleotides derived from the translation initiation site, e.g., between the −10 and +10 regions of the Delta3 nucleotide sequence of interest, are preferred. Particularly preferred antisense molecules are shown below:

```
5' TGCCGCCATCCCTCGGGGCGT 3'       (SEQ ID NO.16)
  (complement to nucleotides 326–346 of SEQ ID NO.1)
5' GGACGCTGCCGCCATCCCCT 3'        (SEQ ID NO.17)
  (complement to nucleotides 333–352 of SEQ ID NO.1)
5' GGACGCTGCCGCCATCCCCTCGGGGCGT 3' (SEQ ID NO.18)
  (complement to nucleotides 326–352 of SEQ ID NO.1)
```

Antisense approaches involve the design of oligonucleotides (either DNA or RNA) that are complementary to Delta3 mRNA. The antisense oligonucleotides will bind to the Delta3 mRNA transcripts and prevent translation. Absolute complementarity, although preferred, is not required. A sequence "complementary" to a portion of an RNA, as referred to herein, means a sequence having sufficient complementarity to be able to hybridize with the RNA, forming a stable duplex; in the case of double-stranded antisense nucleic acids, a single strand of the duplex DNA may thus be tested, or triplex formation may be assayed. The ability to hybridize will depend on both the degree of complementarity and the length of the antisense nucleic acid. Generally, the longer the hybridizing nucleic acid, the more base mismatches with an RNA it may contain and still form a stable duplex (or triplex, as the case may be). One skilled in the art can ascertain a tolerable degree of mismatch by use of standard procedures to determine the melting point of the hybridized complex.

Oligonucleotides that are complementary to the 5' end of the message, e.g., the 5' untranslated sequence up to and including the AUG initiation codon, should work most efficiently at inhibiting translation. However, sequences complementary to the 3' untranslated sequences of mRNAs have recently been shown to be effective at inhibiting translation of mRNAs as well. (Wagner, R. 1994. Nature 372:333). Therefore, oligonucleotides complementary to either the 5' or 3' untranslated, non-coding regions of a Delta3 gene could be used in an antisense approach to inhibit translation of endogenous Delta3 mRNA. Oligonucleotides complementary to the 5' untranslated region of the mRNA should include the complement of the AUG start codon. Antisense oligonucleotides complementary to mRNA coding regions are less efficient inhibitors of translation but could be used in accordance with the invention. Whether designed to hybridize to the 5', 3' or coding region of Delta3 mRNA, antisense nucleic acids should be at least six nucleotides in length, and are preferably oligonucleotides ranging from 6 to about 50 nucleotides in length. In certain embodiments, the oligonucleotide is at least 10 nucleotides, at least 17 nucleotides, at least 25 nucleotides, or at least 50 nucleotides.

Regardless of the choice of target sequence, it is preferred that in vitro studies are first performed to quantitate the ability of the antisense oligonucleotide to quantitate the ability of the antisense oligonucleotide to inhibit gene expression. It is preferred that these studies utilize controls that distinguish between antisense gene inhibition and non-specific biological effects of oligonucleotides. It is also preferred that these studies compare levels of the target RNA or protein with that of an internal control RNA or protein. Additionally, it is envisioned that results obtained using the antisense oligonucleotide are compared with those obtained using a control oligonucleotide. It is preferred that the control oligonucleotide is of approximately the same length as the test oligonucleotide and that the nucleotide sequence of the oligonucleotide differs from the antisense sequence no more than is necessary to prevent specific hybridization to the target sequence.

The oligonucleotides can be DNA or RNA or chimeric mixtures or derivatives or modified versions thereof, single-stranded or double-stranded. The oligonucleotide can be modified at the base moiety, sugar moiety, or phosphate backbone, for example, to improve stability of the molecule, hybridization, etc. The oligonucleotide may include other appended groups such as peptides (e.g., for targeting host cell receptors in vivo), or agents facilitating transport across the cell membrane (see, e.g., Letsinger et al., 1989, Proc. Natl. Acad. Sci. U.S.A. 86:6553–6556; Lemaitre et al., 1987, Proc. Natl. Acad. Sci. 84:648–652; PCT Publication No. WO 88/09810, published Dec. 15, 1988) or the blood-brain barrier (see, e.g., PCT Publication No. WO 89/10134, published Apr. 25, 1988), hybridization-triggered cleavage agents. (See, e.g., Krol et al., 1988, BioTechniques 6:958–976) or intercalating agents. (See, e.g., Zon, 1988, Pharm. Res. 5:539–549). To this end, the oligonucleotide may be conjugated to another molecule, e.g., a peptide, hybridization triggered cross-linking agent, transport agent, hybridization-triggered cleavage agent, etc.

The antisense oligonucleotide may comprise at least one modified base moiety which is selected from the group including but not limited to 5-fluorouracil, 5-bromouracil, 5-chlorouracil, 5-iodouracil, hypoxanthine, xantine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5oxyacetic acid methylester, uracil-5-oxyacetic acid (v), -5-methyl-2-thiouracil, 3-(3-amino-3-N-2-carboxypropyl) uracil, (acp3) w, and 2,6-diaminopurine.

The antisense oligonucleotide may also comprise at least one modified sugar moiety selected from the group including but not limited to arabinose, 2-fluoroarabinose, xylulose, and hexose.

In yet another embodiment, the antisense oligonucleotide comprises at least one modified phosphate backbone selected from the group consisting of a phosphorothioate, a phosphorodithioate, a phosphoramidothioate, a phosphoramidate, a phosphordiamidate, a methylphosphonate, an alkyl phosphotriester, and a formacetal or analog thereof.

In yet another embodiment, the antisense oligonucleotide is an α-anomeric oligonucleotide. An α-anomeric oligonucleotide forms specific double-stranded hybrids with complementary RNA in which, contrary to the usual β-units, the strands run parallel to each other (Gautier et al., 1987, Nucl. Acids Res. 15:6625–6641). The oligonucleotide is a 2'-0-methylribonucleotide (Inoue et al., 1987, Nucl. Acids Res. 15:6131–6148), or a chimeric RNA-DNA analogue (Inoue et al., 1987, FEBS Lett. 215:327–330).

Oligonucleotides of the invention may be synthesized by standard methods known in the art, e.g. by use of an automated DNA synthesizer (such as are commercially available from Biosearch, Applied Biosystems, etc.). As examples, phosphorothioate oligonucleotides may be synthesized by the method of Stein et al. (1988, Nucl. Acids Res. 16:3209), methylphosphonate oligonucleotides can be prepared by use of controlled pore glass polymer supports (Sarin et al., 1988, Proc. Natl. Acad. Sci. U.S.A. 85:7448–7451), etc.

While antisense nucleic acids complementary to the coding region sequence could be used, those complementary to the transcribed untranslated region are preferred. Antisense nucleic acids overlapping the site of initiation of translation are even more preferred. For example, antisense oligonucleotides as set forth below can be utilized in accordance with the invention.

```
5' TCAATCTGGCTCTGTTCGCG 3'          (SEQ ID NO.19)
(complement to nucleotides 284-3030 of SEQ ID NO.1)
5' CGCTCTCTCCACCCGCGGGCCCTCAA 3'    (SEQ ID NO.20)
 (complement to nucleotides 300-325 of SEQ ID NO.1)
```

The antisense molecules should be delivered to cells which express the Delta3 in vivo. A number of methods have been developed for delivering antisense DNA or RNA to cells; e.g., antisense molecules can be injected directly into the tissue site, or modified antisense molecules, designed to target the desired cells e.g., antisense linked to peptides or antibodies that specifically bind receptors or antigens expressed on the target cell surface) can be administered systematically.

However, it is often difficult to achieve intracellular concentrations of the antisense sufficient to suppress translation on endogenous mRNAs. Therefore a preferred approach utilizes a recombinant DNA construct in which the antisense oligonucleotide is placed under the control of a strong pol III or pol II promoter. The use of such a construct to transfect target cells in the patient will result in the transcription of sufficient amounts of single stranded RNAs that will form complementary base pairs with the endogenous Delta3 transcripts and thereby prevent translation of the Delta3 mRNA. For example, a vector can be introduced in vivo such that it is taken up by a cell and directs the transcription of an antisense RNA. Such a vector can remain episomal or become chromosomally integrated, as long as it can be transcribed to produce the desired antisense RNA. Such vectors can be constructed by recombinant DNA technology methods standard in the art. Vectors can be plasmid, viral, or others known in the art, used for replication and expression in mammalian cells. Expression of the sequence encoding the antisense RNA can be by any promoter known in the art to act in mammalian, preferably human cells. Such promoters can be inducible or constitutive. Such promoters include but are not limited to: the SV40 early promoter region (Bernoist and Chambon, 1981, Nature 290:304–310), the promoter contained in the 3' long terminal repeat of Rous sarcoma virus (Yamamoto et al., 1980, Cell 22:787–797), the herpes thymidine kinase promoter (Wagner et al., 1981, Proc. Natl. Acad. Sci. U.S.A. 78:1441–1445), the regulatory sequences of the metallothionein gene (Brinster et al, 1982, Nature 296:39–42), etc. Any type of plasmid, cosmid, YAC or viral vector can be used to prepare the recombinant DNA construct which can be introduced directly into the tissue site; e.g., the choroid plexus or hypothalamus. Alternatively, viral vectors can be used which selectively infect the desired tissue; (e.g., for brain, herpesvirus vectors may be used), in which case administration may be accomplished by another route (e.g., systematically).

Likewise, the antisense constructs of the present invention, by antagonizing the normal biological activity of one of the Delta3 proteins, can be used in the modulation of cellular activity both in vivo and for ex vivo tissue cultures.

Furthermore, the anti-sense techniques (e.g. microinjection of antisense molecules, or transfection with plasmids whose transcripts are anti-sense with regard to a Delta3 mRNA or gene sequence) can be used to investigate the role of Delta3 in developmental events, as well as the normal cellular function of Delta3 in adult tissue. Such techniques can be utilized in cell culture, but can also be used in the creation of transgenic animals, as detailed below.

Ribozyme molecules designed to catalytically cleave Delta3 mRNA transcripts can also be used to prevent translation of mRNA and expression of Delta3. (See, e.g., PCT International Publication WO 94/11364, published Oct. 4, 1990; Sarver et al., 1990, Science 247:1222–1225). Ribozymes are enzymatic RNA molecules capable of catalyzing the specific cleavage of RNA. The mechanism of ribozyme action involves sequence specific hybridization of the ribozyme molecule to complementary target RNA, followed by an endonucleolytic cleavage. The composition of ribozyme molecules must include one or more sequences complementary to the target gene mRNA, and must include the well known catalytic sequence responsible for mRNA cleavage. For this sequence, see U.S. Pat. No. 5,093,246, which is incorporated by reference herein in its entirety. As such within the scope of the invention are engineered hammerhead motif ribozyme molecules that specifically and efficiently catalyze endonucleolytic cleavage of RNA sequences encoding Delta3 proteins.

Specific ribozyme cleavage sites within any potential RNA target are initially identified by scanning the molecule of interest for ribozyme cleavage sites which include the following sequences, GUA, GUU and GUC. Once identified, short RNA sequences of between 15 and 20 ribonucleotides corresponding to the region of the target gene containing the cleavage site may be evaluated for predicted structural features, such as secondary structure, that may render the oligonucleotide sequence unsuitable. The suitability of candidate sequences may also be evaluated by testing their accessibility to hybridization with complementary oligonucleotides, using ribonuclease protection assays.

While ribozymes that cleave mRNA at site specific recognition sequences can be used to destroy Delta3 mRNAs, the use of hammerhead ribozymes is preferred. Hammerhead ribozymes cleave mRNAs at locations dictated by flanking regions that form complementary base pairs with the target mRNA. The sole requirement is that the target mRNA have the following sequence of two bases: 5'-UG-3'. The construction and production of hammerhead ribozymes is well known in the art and is described more fully in Haseloff and Gerlach, 1988, Nature, 334:585–591. There are hundreds of potential hammerhead ribozyme cleavage sites within the nucleotide sequence of human Delta3 cDNA (FIG. 1). Preferably the ribozyme is engineered so that the cleavage recognition site is located near the 5' end of the Delta3 mRNA; i.e., to increase efficiency and minimize the intracellular accumulation of non-functional mRNA transcripts.

The ribozymes of the present invention also include RNA endoribonucleases (hereinafter "Cech-type ribozymes") such as the one which occurs naturally in Tetrahymena Thermophila (known as the IVS, or L-19 IVS RNA) and which has been extensively described by Thomas Cech and collaborators (Zaug, et al., 1984, Science, 224:574–578; Zaug and Cech, 1986, Science, 231:470–475; Zaug, et al., 1986, Nature, 324:429–433; published International patent application No. WO88/04300 by University Patents Inc.; Been and Cech, 1986, Cell, 47:207–216). The Cech-type ribozymes have an eight base pair active site which hybridizes to a target RNA sequence whereafter cleavage of the target RNA takes place. The invention encompasses those Cech-type ribozymes which target eight base-pair active site sequences that are present in Delta3.

As in the antisense approach, the ribozymes can be composed of modified oligonucleotides (e.g. for improved stability, targeting, etc.) and should be delivered to cells which express the Delta3 in vivo e.g., hypothalamus and/or the choroid plexus. A preferred method of delivery involves using a DNA construct "encoding" the ribozyme under the control of a strong constitutive pol III or pol II promoter, so that transfected cells will produce sufficient quantities of the ribozyme to destroy endogenous Delta3 messages and inhibit translation. Because ribozymes unlike antisense molecules, are catalytic, a lower intracellular concentration is required for efficiency.

Endogenous Delta3 gene expression can also be reduced by inactivating or "knocking out" the Delta3 gene or its promoter using targeted homologous recombination. (E.g., see Smithies et al., 1985, Nature 317:230–234; Thomas & Capecchi, 1987, Cell 51:503–512; Thompson et al., 1989 Cell 5:313–321; each of which is incorporated by reference herein in its entirety). For example, a mutant, non-functional Delta3 (or a completely unrelated DNA sequence) flanked by DNA homologous to the endogenous Delta3 gene (either the coding regions or regulatory regions of the Delta3 gene) can be used, with or without a selectable marker and/or a negative selectable marker, to transfect cells that express Delta3 in vivo. Insertion of the DNA construct, via targeted homologous recombination, results in inactivation of the Delta3 gene. Such approaches are particularly suited in the agricultural field where modifications to ES (embryonic stem) cells can be used to generate animal offspring with an inactive Delta3 (e.g., see Thomas & Capecchi 1987 and Thompson 1989, supra). However this approach can be adapted for use in humans provided the recombinant DNA constructs are directly administered or targeted to the required site in vivo using appropriate viral vectors, e.g., herpes virus vectors.

Alternatively, endogenous Delta3 gene expression can be reduced by targeting deoxyribonucleotide sequences complementary to the regulatory region of the Delta3 gene (i.e., the Delta3 promoter and/or enhancers) to form triple helical structures that prevent transcription of the Delta3 gene in target cells in the body. (See generally, Helene, C. 1991, Anticancer Drug Des., 6(6):569–84; Helene, C., et al., 1992, Ann, N.Y. Acad. Sci., 660:27–36; and Maher, L. J., 1992, Bioassays 14(12):807–15).

Nucleic acid molecules to be used in triple helix formation for the inhibition of transcription are preferably single stranded and composed of deoxyribonucleotides. The base composition of these oligonucleotides should promote triple helix formation via Hoogsteen base pairing rules, which generally require sizable stretches of either purines or pyrimidines to be present on one strand of a duplex. Nucleotide sequences may be pyrimidine-based, which will result in TAT and CGC triplets across the three associated strands of the resulting triple helix. The pyrimidine-rich molecules provide base complementarity to a purine-rich region of a single strand of the duplex in a parallel orientation to that strand. In addition, nucleic acid molecules may be chosen that are purine-rich, for example, containing a stretch of G residues. These molecules will form a triple helix with a DNA duplex that is rich in GC pairs, in which the majority of the purine residues are located on a single strand of the targeted duplex, resulting in CGC triplets across the three strands in the triplex.

Alternatively, the potential sequences that can be targeted for triple helix formation may be increased by creating a so called "switchback" nucleic acid molecule. Switchback molecules are synthesized in an alternating 5'-3', 3'-5' manner, such that they base pair with first one strand of a duplex and then the other, eliminating the necessity for a sizable stretch of either purines or pyrimidines to be present on one strand of a duplex.

Antisense RNA and DNA, ribozyme, and triple helix molecules of the invention may be prepared by any method known in the art for the synthesis of DNA and RNA molecules. These include techniques for chemically synthesizing oligodeoxyribonucleotides and oligoribonucleotides well known in the art such as for example solid phase phosphoramidite chemical synthesis. Alternatively, RNA molecules may be generated by in vitro and in vivo transcription of DNA sequences encoding the antisense RNA molecule. Such DNA sequences may be incorporated into a wide variety of vectors which incorporate suitable RNA polymerase promoters such as the T7 or SP6 polymerase promoters. Alternatively, antisense cDNA constructs that synthesize antisense RNA constitutively or inducibly, depending on the promoter used, can be introduced stably into cell lines.

Moreover, various well-known modifications to nucleic acid molecules may be introduced as a means of increasing intracellular stability and half-life. Possible modifications include but are not limited to the addition of flanking sequences of ribonucleotides or deoxyribonucleotides to the 5' and/or 3' ends of the molecule or the use of phosphorothioate or 2' O-methyl rather than phosphodiesterase linkages within the oligodeoxyribonucleotide backbone.

4.4 Polypeptides of the Present Invention

The present invention also makes available Delta3 polypeptides which are isolated from, or otherwise substantially free of other cellular proteins, especially other signal transduction factors and/or transcription factors which may normally be associated with the Delta3 polypeptide. The term "substantially free of other cellular proteins" (also referred to herein as "contaminating proteins") or "substantially pure or purified preparations" are defined as encompassing preparations of Delta3 polypeptides having less than about 20% (by dry weight) contaminating protein, and preferably having less than about 5% contaminating protein. Functional forms of the subject polypeptides can be prepared, for the first time, as purified preparations by using a cloned gene as described herein. By "purified", it is meant, when referring to a peptide or DNA or RNA sequence, that the indicated molecule is present in the substantial absence of other biological macromolecules, such as other proteins. The term "purified" as used herein preferably means at least 80% by dry weight, more preferably in the range of 95–99% by weight, and most preferably at least 99.8% by weight, of biological macromolecules of the same type present (but water, buffers, and other small molecules, especially molecules having a molecular weight of less than about 5000, can be present). The term "pure" as used herein preferably has the same numerical limits as "purified" immediately above. "Isolated" and "purified" do not encompass either natural materials in their native state or natural materials that have been separated into components (e.g., in an acrylamide gel) but not obtained either as pure (e.g. lacking contaminating proteins, or chromatography reagents such as denaturing agents and polymers, e.g. acrylamide or agarose) substances or solutions. In preferred embodiments, purified Delta3 preparations will lack any contaminating proteins from the same animal from which Delta3 is normally produced, as can be accomplished by recombinant expression of, for example, a human Delta3 protein in a non-human cell.

Full length proteins or fragments corresponding to one or more particular motifs and/or domains or to arbitrary sizes, for example, at least about 5, 10, 25, 50, 75, 100, 125, 150 amaino acids in length are within the scope of the present invention. The invention encompasses all proteins encoded by the nucleic acids described in the above section describing the nucleic acids of the invention.

For example, isolated Delta3 polypeptides can include all or a portion of an amino acid sequences corresponding to a Delta3 polypeptide represented in SEQ ID No: 2. Isolated peptidyl portions of Delta3 proteins can be obtained by screening peptides recombinantly produced from the corresponding fragment of the nucleic acid encoding such peptides. In addition, fragments can be chemically synthesized using techniques known in the art such as conventional Merrifield solid phase f-Moc or t-Boc chemistry. For example, a Delta3 polypeptide of the present invention may be arbitrarily divided into fragments of desired length with no overlap of the fragments, or preferably divided into overlapping fragments of a desired length. The fragments can be produced (recombinantly or by chemical synthesis) and tested to identify those peptidyl fragments which can function as either agonists or antagonists of a wild-type (e.g., "authentic") Delta3 protein.

Another aspect of the present invention concerns recombinant forms of the Delta3 proteins. Recombinant polypeptides preferred by the present invention, in addition to native Delta3 proteins, are at least about 90% homologous and more preferably at least about 92% or 94% homologous and most preferably at least about 95%, 96%, 97%, 98% or 99% homologous with an amino acid sequence represented by SEQ ID No: 2. In one embodiment, the delta polypeptide of the invention has an overall amino acid sequence homology or identity of at least about 70%, at least about 75%, at least about 80%, at least about 85%, at least about 90%, at least about 95%, at least about 98%, or at least about 99% with the amino acid sequence SEQ ID No. 2. In a particularly preferred embodiment a Delta3 protein has the amino acid sequence SEQ ID No: 2. In other particularly preferred embodiments, the Delta3 protein has a Delta3 bioactivity.

The present invention further pertains to recombinant forms of one of the subject Delta3 polypeptides which are encoded by genes derived from a mammalian organism, and which have amino acid sequences evolutionarily related to the Delta3 protein represented in SEQ ID No: 2. Such recombinant Delta3 polypeptides preferably are capable of functioning in one of either role of an agonist or antagonist of at least one biological activity of a wild-type ("authentic") Delta3 protein of the appended sequence listing. The term "evolutionarily related to", with respect to amino acid sequences of human Delta3 proteins, refers to both polypeptides having amino acid sequences which have arisen naturally, and also to mutational variants of the Delta3 polypeptides which are derived, for example, by combinatorial mutagenesis. Such evolutionarily derived Delta3 polypeptides preferred by the present invention have a Delta3 bioactivity and are at least 80% homologous and more preferably 85% homologous and most preferably 90% homologous with the amino acid sequence of SEQ ID No: 2. In a particularly preferred embodiment, a Delta3 protein comprises the amino acid coding sequence of SEQ ID No: 2.

In general, polypeptides referred to herein as having an activity (e.g., "bioactivity") of a Delta3 protein are defined as polypeptides which include an amino acid sequence corresponding (e.g., identical or substantially identical) to all or a portion of the amino acid sequences of a Delta3 protein shown in SEQ ID No: 2 and which mimic or antagonize all or a portion of the biologicalbiochemical activities of a naturally occurring Delta3 protein. In preferred embodiments a Delta3 protein of the present invention specifically interacts with a Notch polypeptide.

The invention provides various forms of Delta3 proteins, specifically including all of the Delta3 proteins described in the section "4.3" relating to nucleic acids of the invention.

The present invention further pertains to methods of producing the subject Delta3 polypeptides. For example, a host cell transfected with a nucleic acid vector directing expression of a nucleotide sequence encoding the subject polypeptides can be cultured under appropriate conditions to allow expression of the peptide to occur. The cells may be harvested, lysed and the protein isolated. A cell culture includes host cells, media and other byproducts. Suitable media for cell culture are well known in the art. The recombinant Delta3 polypeptide can be isolated from cell culture medium, host cells, or both using techniques known in the art for purifying proteins including ion-exchange chromatography, gel filtration chromatography, ultrafiltration, electrophoresis, and immunoaffinity purification with antibodies specific for such peptide. In a preferred embodiment, the recombinant Delta3 polypeptide is a fusion protein containing a domain which facilitates its purification, such as GST fusion protein or poly(His) fusion protein.

Moreover, it will be generally appreciated that, under certain circumstances, it may be advantageous to provide variants of one of the subject Delta3 polypeptides which function in a limited capacity as one of either a Delta3 agonist (mimetic) or a Delta3 antagonist, in order to promote or inhibit only a subset of the biological activities of the naturally-occurring form of the protein. Thus, specific biological effects can be elicited by treatment with a variant having a limited function, and with fewer side effects relative to treatment with agonists or antagonists which are directed to all of the biological activities of naturally occurring forms of Delta3 proteins.

Variants and/or mutants of each of the subject Delta3 proteins can be generated by mutagenesis, such as by discrete point mutation(s), or by truncation. For instance, mutation can give rise to homologs which retain substantially the same, or merely a subset, of the biological activity of the Delta3 polypeptide from which it was derived. Alternatively, antagonistic forms of the protein can be generated which are able to inhibit the function of the naturally occurring form of the protein, such as by competitively binding to a downstream or upstream member of the Delta3 cascade which includes the Delta3 protein. In addition, agonistic forms of the protein may be generated which are constitutively active.

The recombinant Delta3 polypeptides of the present invention also include homologs of the authentic Delta3 proteins, such as versions of those protein which are resistant to proteolytic cleavage, as for example, due to mutations which alter ubiquitination or other enzymatic targeting associated with the protein.

Delta3 polypeptides may also be chemically modified to create Delta3 derivatives by forming covalent or aggregate conjugates with other chemical moieties, such as glycosyl groups, lipids, phosphate, acetyl groups and the like. Covalent derivatives of Delta3 proteins can be prepared by linking the chemical moieties to functional groups on amino acid sidechains of the protein or at the N-terminus or at the C-terminus of the polypeptide.

Modification of the structure of the subject Delta3 polypeptides can be for such purposes as enhancing therapeutic or prophylactic efficacy, stability (e.g., ex vivo shelf life and resistance to proteolytic degradation in vivo), or post-translational modifications (e.g., to alter phosphorylation pattern of protein). Such modified peptides, when designed to retain at least one activity of the naturally-occurring form of the protein, or to produce specific antagonists thereof, are considered functional equivalents of the Delta3 polypeptides described in more detail herein. Such modified peptides can be produced, for instance, by amino acid substitution, deletion, or addition.

For example, it is reasonable to expect that an isolated replacement of a leucine with an isoleucine or valine, an aspartate with a glutamate, a threonine with a serine, or a similar replacement of an amino acid with a structurally related amino acid (i.e. isosteric and/or isoelectric mutations) will not have a major effect on the biological activity of the resulting molecule. Conservative replacements are those that take place within a family of amino acids that are related in their side chains. Genetically encoded amino acids are can be divided into four families: (1) acidic=aspartate, glutamate; (2) basic=lysine, arginine, histidine; (3) nonpolar=alanine, valine, leucine, isoleucine, proline, phenylalanine, methionine, tryptophan; and (4) uncharged polar=glycine, asparagine, glutamine, cysteine, serine, threonine, tyrosine. In similar fashion, the amino acid repertoire can be grouped as (1) acidic=aspartate, glutamate; (2) basic=lysine, arginine histidine, (3) aliphatic=glycine, alanine, valine, leucine, isoleucine, serine, threonine, with serine and threonine optionally be grouped separately as aliphatic-hydroxyl; (4) aromatic=phenylalanine, tyrosine, tryptophan; (5) amide=asparagine, glutamine; and (6) sulfur-containing=cysteine and methionine. (see, for example, Biochemistry, 2nd ed., Ed. by L. Stryer, WH Freeman and Co.: 1981). Whether a change in the amino acid sequence of a peptide results in a functional Delta3 homolog (e.g. functional in the sense that the resulting polypeptide mimics or antagonizes the wild-type form) can be readily determined by assessing the ability of the variant peptide to produce a response in cells in a fashion similar to the wild-type protein, or competitively inhibit such a response. Polypeptides in which more than one replacement has taken place can readily be tested in the same manner.

This invention further contemplates a method for generating sets of combinatorial mutants of the subject Delta3 proteins as well as truncation mutants, and is especially useful for identifying potential functional variant sequences (e.g. homologs). The purpose of screening such combinatorial libraries is to generate, for example, novel Delta3 homologs which can act as either agonists or antagonist, or alternatively, possess novel activities all together.

In one embodiment, the variegated library of Delta3 variants is generated by combinatorial mutagenesis at the nucleic acid level, and is encoded by a variegated gene library. For instance, a mixture of synthetic oligonucleotides can be enzymatically ligated into gene sequences such that the degenerate set of potential Delta3 sequences are expressible as individual polypeptides, or alternatively, as a set of larger fusion proteins (e.g. for phage display) containing the set of Delta3 sequences therein.

There are many ways by which such libraries of potential Delta3 homologs or variants can be generated from a degenerate oligonucleotide sequence. Chemical synthesis of a degenerate gene sequence can be carried out in an automatic DNA synthesizer, and the synthetic genes then ligated into an appropriate expression vector. The purpose of a degenerate set of genes is to provide, in one mixture, all of the sequences encoding the desired set of potential Delta3 sequences. The synthesis of degenerate oligonucleotides is well known in the art (see for example, Narang, S A (1983) Tetrahedron 39:3; Itakura et al. (1981) Recombinant DNA, Proc 3rd Cleveland Sympos. Macromolecules, ed. A G Walton, Amsterdam: Elsevier ppg. 273–289; Itakura et al. (1984) Annu. Rev. Biochem. 53:323; Itakura et al. (1984) Science 198:1056; Ike et al. (1983) Nucleic Acid Res. 11:477. Such techniques have been employed in the directed evolution of other proteins (see, for example, Scott et al. (1990) Science 249:386–390; Roberts et al. (1992) PNAS 89:2429–2433; Devlin et al. (1990) Science 249: 404–406; Cwirla et al. (1990) PNAS 87: 6378–6382; as well as U.S. Pat. Nos. 5,223,409, 5,198,346, and 5,096,815).

Likewise, a library of coding sequence fragments can be provided for a Delta3 clone in order to generate a variegated population of Delta3 fragments for screening and subsequent selection of bioactive fragments. A variety of techniques are known in the art for generating such libraries, including chemical synthesis. In one embodiment, a library of coding sequence fragments can be generated by (i) treating a double stranded PCR fragment of a Delta3 coding sequence with a nuclease under conditions wherein nicking occurs only about once per molecule; (ii) denaturing the double stranded DNA; (iii) renaturing the DNA to form double stranded DNA which can include sense/antisense pairs from different nicked products; (iv) removing single stranded portions from reformed duplexes by treatment with S1 nuclease; and (v) ligating the resulting fragment library into an expression vector. By this exemplary method, an expression library can be derived which codes for N-terminal, C-terminal and internal fragments of various sizes.

A wide range of techniques are known in the art for screening gene products of combinatorial libraries made by point mutations or truncation, and for screening cDNA libraries for gene products having a certain property. Such techniques will be generally adaptable for rapid screening of the gene libraries generated by the combinatorial mutagenesis of Delta3 homologs. The most widely used techniques for screening large gene libraries typically comprises cloning the gene library into replicable expression vectors, transforming appropriate cells with the resulting library of vectors, and expressing the combinatorial genes under conditions in which detection of a desired activity facilitates relatively easy isolation of the vector encoding the gene whose product was detected. Each of the illustrative assays described below are amenable to high through-put analysis as necessary to screen large numbers of degenerate Delta3 sequences created by combinatorial mutagenesis techniques.

Combinatorial mutagenesis has a potential to generate very large libraries of mutant proteins, e.g., in the order of $10^{26}$ molecules. Combinatorial libraries of this size may be technically challenging to screen even with high throughput screening assays. To overcome this problem, a new technique has been developed recently, recrusive ensemble mutagenesis (REM), which allows one to avoid the very high proportion of non-functional proteins in a random library and simply enhances the frequency of functional proteins, thus decreasing the complexity required to achieve a useful sampling of sequence space. REM is an algorithm which enhances the frequency of functional mutants in a library when an appropriate selection or screening method is employed (Arkin and Yourvan, 1992, PNAS USA 89:7811–7815; Yourvan et al., 1992, Parallel Problem Solving from Nature, 2., In Maenner and Manderick, eds., Elsevir Publishing Co., Amsterdam, pp. 401–410; Delgrave et al., 1993, Protein Engineering 6(3):327–331).

The invention also provides for reduction of the Delta3 proteins to generate mimetics, e.g. peptide or non-peptide agents, which are able to bind to a Delta3 protein and/or to disrupt binding of a Delta3 polypeptide of the present invention with either upstream or downstream components of a Delta/Notch signaling cascade, such as binding proteins or interactors. Thus, such mutagenic techniques as described above are also useful to map the determinants of the Delta3 proteins which participate in protein-protein interactions involved in, for example, binding of the subject Delta3 polypeptide to proteins which may function upstream (including both activators and repressors of its activity) or to proteins or nucleic acids which may function downstream of the Delta3 polypeptide, whether they are positively or negatively regulated by it, for example, Notch. To illustrate, the critical residues of a subject Delta3 polypeptide which are involved in molecular recognition of, for example, the Notch gene product or other component upstream or downstream of a Delta3 gene can be determined and used to generate Delta-derived peptidomimetics which competitively inhibit binding of the authentic Delta3 protein with that moiety. By employing, for example, scanning mutagenesis to map the amino acid residues of each of the subject Delta3 proteins which are involved in binding other extracellular proteins, peptidomimetic compounds can be generated which mimic those residues of the Delta3 protein which facilitate the interaction. Such mimetics may then be used to interfere with the normal function of a Delta3 protein. For instance, non-hydrolyzable peptide analogs of such residues can be generated using benzodiazepine (e.g., see Freidinger et al. in Peptides: Chemistry and Biology, G. R. Marshall ed., ESCOM Publisher: Leiden, Netherlands, 1988), azepine (e.g., see Huffman et al. in Peptides: Chemistry and Biology, G. R. Marshall ed., ESCOM Publisher: Leiden, Netherlands, 1988), substituted gamma lactam rings (Garvey et al. in Peptides: Chemistry and Biology, G. R. Marshall ed., ESCOM Publisher: Leiden, Netherlands, 1988), keto-methylene pseudopeptides (Ewenson et al. (1986) J Med Chem 29:295; and Ewenson et al. in Peptides: Structure and Function (Proceedings of the 9th American Peptide Symposium) Pierce Chemical Co. Rockland, Ill., 1985), b-turn dipeptide cores (Nagai et al. (1985) Tetrahedron Lett 26:647; and Sato et al. (1986) J Chem Soc Perkin Trans 1:1231), and b-aminoalcohols (Gordon et al. (1985) Biochem Biophys Res Commun126:419; and Dann et al. (1986) Biochem Biophys Res Commun 134:71).

4.4.1. Cells expressing recombinant Delta3 polypeptides.

This invention also pertains to a host cell transfected to express a recombinant form of the subject Delta3 polypeptides. The host cell may be any prokaryotic or eukaryotic cell. Thus, a nucleotide sequence derived from the cloning of Delta3 proteins, encoding all or a selected portion of the full-length protein, can be used to produce a recombinant form of a Delta3 polypeptide via microbial or eukaryotic cellular processes. Ligating the polynucleotide sequence into a gene construct, such as an expression vector, and transforming or transfecting into hosts, either eukaryotic (yeast, avian, insect or mammalian) or prokaryotic (bacterial) cells, are standard procedures used in producing other well-known proteins, e.g. MAP kinase, pg. 53, WT1, PTP phosphotases, SRC, and the like. Similar procedures, or modifications thereof, can be employed to prepare recombinant Delta3 polypeptides by microbial means or tissue-culture technology in accord with the subject invention.

The recombinant Delta3 genes can be produced by ligating a nucleic acid encoding a Delta3 protein, or a portion thereof, into a vector suitable for expression in either prokaryotic cells, eukaryotic cells, or both. Expression vectors for production of recombinant forms of the subject Delta3 polypeptides include plasmids and other vectors. For instance, suitable vectors for the expression of a Delta3 polypeptide include plasmids of the types: pBR322-derived plasmids, pEMBL-derived plasmids, pEX-derived plasmids, pBTac-derived plasmids and pUC-derived plasmids for expression in prokaryotic cells, such as E. coli.

A number of vectors exist for the expression of recombinant proteins in yeast. For instance, YEP24, YIP5, YEP51, YEP52, pYES2, and YRP17 are cloning and expression vehicles useful in the introduction of genetic constructs into S. cerevisiae (see, for example, Broach et al. (1983) in Experimental Manipulation of Gene Expression, ed. M. Inouye Academic Press, p. 83, incorporated by reference herein). These vectors can replicate in E. coli due the presence of the pBR322 ori, and in S. cerevisiae due to the replication determinant of the yeast 2 micron plasmid. In addition, drug resistance markers such as ampicillin can be used. In an illustrative embodiment, a Delta3 polypeptide is produced recombinantly utilizing an expression vector generated by sub-cloning the Delta3 gene represented in SEQ ID No: 1.

The preferred mammalian expression vectors contain both prokaryotic sequences, to facilitate the propagation of the vector in bacteria, and one or more eukaryotic transcription units that are expressed in eukaryotic cells. The pcDNAI/amp, pcDNAI/neo, pRc/CMV, pSV2gpt, pSV2neo, pSV2-dhfr, pTk2, pRSVneo, pMSG, pSVT7, pko-neo and pHyg derived vectors are examples of mammalian expression vectors suitable for transfection of eukaryotic cells. Some of these vectors are modified with sequences from bacterial plasmids, such as pBR322, to facilitate replication and drug resistance selection in both prokaryotic and eukaryotic cells. Alternatively, derivatives of viruses such as the bovine papillomavirus (BPV-1), or Epstein-Barr virus (pHEBo, pREP-derived and p205) can be used for transient expression of proteins in eukaryotic cells. The various methods employed in the preparation of the plasmids and transformation of host organisms are well known in the art. For other suitable expression systems for both prokaryotic and eukaryotic cells, as well as general recombinant procedures, see Molecular Cloning A Laboratory Manual, 2nd Ed., ed. by Sambrook, Fritsch and Maniatis (Cold Spring Harbor Laboratory Press: 1989) Chapters 16 and 17.

In some instances, it may be desirable to express the recombinant Delta3 polypeptide by the use of a baculovirus expression system. Examples of such baculovirus expression systems include pVL-derived vectors (such as pVL1392, pVL1393 and pVL941), pAcUW-derived vectors (such as pAcUWI), and pBlueBac-derived vectors (such as the β-gal containing pBlueBac III).

When it is desirable to express only a portion of a Delta3 protein, such as a form lacking a portion of the N-terminus, i.e. a truncation mutant which lacks the signal peptide, it may be necessary to add a start codon (ATG) to the oligonucleotide fragment containing the desired sequence to be expressed. It is well known in the art that a methionine at the N-terminal position can be enzymatically cleaved by the use of the enzyme methionine aminopeptidase (MAP). MAP has been cloned from E. coli (Ben-Bassat et al. (1987) J. Bacteriol. 169:751–757) and Salmonella typhimurium and its in vitro activity has been demonstrated on recombinant proteins (Miller et al. (1987) PNAS 84:2718–1722). Therefore, removal of an N-terminal methionine, if desired, can be achieved either in vivo by expressing Delta-derived polypeptides in a host which produces MAP (e.g., E. coli or CM89 or S. cerevisiae), or in vitro by use of purified MAP (e.g., procedure of Miller et al., supra).

In other embodiments transgenic animals, described in more detail below could be used to produce recombinant proteins.

4.4.2 Fusion proteins and Immunogens.

In another embodiment, the coding sequences for the polypeptide can be incorporated as a part of a fusion gene including a nucleotide sequence encoding a different polypeptide.

In a preferred embodiment, the Delta3 polypeptide is a Delta3-Ig polypeptide. The Delta3-Ig polypeptide can comprise the entire extracellular domain of Delta3, e.g., human Delta3, or a variant thereof. For example, a Delta3-Ig polypeptide can comprise an amino acid sequences from about amino acid 1 to about amino acid 529 of SEQ ID No. 2. Other preferred Delta3-Ig proteins do not comprise a signal peptide and thus, preferably do not comprise about amino acid 1 to about amino acid 17 of SEQ ID No. 2. Alternatively, a Delta3-Ig fusion protein can comprise a portion of the extracellular domain of a Delta3 protein or a variant of a portion of the extracellular domain of a Delta3 protein. Preferred portions of the extracellular domain include portions having at least one motif shown in FIG. 2. For example a Delta3-Ig fusion protein can comprise at least one EGF-like repeat. A Delta3-Ig fusion protein can further comprise a DSL domain. A Delta3-Ig fustion protein can also further comprise a signal peptide. Delta3-Ig fusion proteins can be prepared as described e.g., in U.S. Pat. No. 5,434,131.

This type of expression system can be useful under conditions where it is desirable to produce an immunogenic fragment of a Delta3 protein. For example, the VP6 capsid protein of rotavirus can be used as an immunologic carrier protein for portions of the Delta3 polypeptide, either in the monomeric form or in the form of a viral particle. The nucleic acid sequences corresponding to the portion of a subject Delta3 protein to which antibodies are to be raised can be incorporated into a fusion gene construct which includes coding sequences for a late vaccinia virus structural protein to produce a set of recombinant viruses expressing fusion proteins comprising Delta3 epitopes as part of the virion, It has been demonstrated with the use of immunogenic fusion proteins utilizing the Hepatitis B surface antigen fusion proteins that recombinant Hepatitis B virions can be utilized in this role as well. Similarly, chimeric constructs coding for fusion proteins containing a portion of a Delta3 protein and the poliovirus capsid protein can be created to enhance immunogenicity of the set of polypeptide antigens (see, for example, EP Publication No: 0259149; and Evans et al. (1989) Nature 339:385; Huang et al. (1988) J. Virol. 62:3855; and Schlienger et al. (1992) J. Virol. 66:2).

The Multiple Antigen Peptide system for peptide-based immunization can also be utilized to generate an immunogen, wherein a desired portion of a Delta3 polypeptide is obtained directly from organo-chemical synthesis of the peptide onto an oligomeric branching lysine core (see, for example, Posnett et al. (1988) JBC 263:1719 and Nardelli et al. (1992) J. Immunol. 148:914). Antigenic determinants of Delta3 proteins can also be expressed and presented by bacterial cells.

In addition to utilizing fusion proteins to enhance immunogenicity, it is widely appreciated that fusion proteins can also facilitate the expression of proteins, and accordingly, can be used in the expression of the Delta3 polypeptides of the present invention. For example, Delta3 polypeptides can be generated as glutathione-S-transferase (GST-fusion) proteins. Such GST-fusion proteins can enable easy purification of the Delta3 polypeptide, as for example by the use of glutathione-derivatized matrices (see, for example, Current Protocols in Molecular Biology, eds. Ausubel et al. (N.Y.: John Wiley & Sons, 1991)).

In another embodiment, a fusion gene coding for a purification leader sequence, such as a poly-(is)/enterokinase cleavage site sequence at the N-terminus of the desired portion of the recombinant protein, can allow purification of the expressed fusion protein by affinity chromatography using a Ni2+metal resin. The purification leader sequence can then be subsequently removed by treatment with enterokinase to provide the purified protein (e.g., see Hochuli et al. (1987) J. Chromatography 411:177; and Janknecht et al. PNAS 88:8972).

Techniques for making fusion genes are known to those skilled in the art. Essentially, the joining of various DNA fragments coding for different polypeptide sequences is performed in accordance with conventional techniques, employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed to generate a chimeric gene sequence (see, for example, Current Protocols in Molecular Biology, eds. Ausubel et al. John Wiley & Sons: 1992).

4.4.3. Antibodies

Another aspect of the invention pertains to an antibody specifically reactive with a Delta3 protein. For example, by using immunogens derived from a Delta3 protein, e.g. based on the cDNA sequences, anti-protein/anti-peptide antisera or monoclonal antibodies can be made by standard protocols (See, for example, Antibodies: A Laboratory Manual ed. by Harlow and Lane (Cold Spring Harbor Press: 1988)). A mammal, such as a mouse, a hamster or rabbit can be immunized with an immunogenic form of the peptide (e.g., a Delta3 polypeptide or an antigenic fragment which is capable of eliciting an antibody response, or a fusion protein as described above). Techniques for conferring immunogenicity on a protein or peptide include conjugation to carriers or other techniques well known in the art. An immunogenic portion of a Delta3 protein can be administered in the presence of adjuvant. The progress of immunization can be monitored by detection of antibody titers in plasma or serum. Standard ELISA or other immunoassays can be used with the immunogen as antigen to assess the levels of antibodies. In a preferred embodiment, the subject antibodies are immunospecific for antigenic determinants of a Delta3 protein of a mammal, e.g. antigenic determinants of a protein represented by SEQ ID No: 2 or closely related homologs (e.g. at least 92% homologous, and more preferably at least 94% homologous).

Following immunization of an animal with an antigenic preparation of a Delta3 polypeptide, anti-Delta3 antisera can be obtained and, if desired, polyclonal anti-Delta3 antibodies isolated from the serum. To produce monoclonal antibodies, antibody-producing cells (lymphocytes) can be harvested from an immunized animal and fused by standard somatic cell fusion procedures with immortalizing cells such as myeloma cells to yield hybridoma cells. Such techniques are well known in the art, and include, for example, the hybridoma technique (originally developed by Kohler and Milstein, (1975) Nature, 256: 495–497), the human B cell hybridoma technique (Kozbar et al., (1983) Immunology Today, 4: 72), and the EBV-hybridoma technique to produce human monoclonal antibodies (Cole et al., (1985) Monoclonal Antibodies and Cancer Therapy, Alan R. Liss, Inc. pp. 77–96). Hybridoma cells can be screened immunochemically for production of antibodies specifically reactive with a Delta3 polypeptide of the present invention and monoclonal antibodies isolated from a culture comprising such hybridoma cells. In one embodiment anti-human Delta3 antibodies specifically react with the proteins encoded by the DNA of ATCC Deposit Accession Number 98348.

The term antibody as used herein is intended to include fragments thereof which are also specifically reactive with one of the subject Delta3 polypeptides. Antibodies can be fragmented using conventional techniques and the fragments screened for utility in the same manner as described above for whole antibodies. For example, $F(ab)_2$ fragments can be generated by treating antibody with pepsin. The resulting $F(ab)_2$ fragment can be treated to reduce disulfide bridges to produce Fab fragments. The antibody of the present invention is further intended to include bispecific and chimeric molecules having affinity for a Delta3 protein conferred by at least one CDR region of the antibody.

Antibodies which specifically bind Delta3 epitopes can also be used in immunohistochemical staining of tissue samples in order to evaluate the abundance and pattern of expression of each of the subject Delta3 polypeptides. Anti-Delta3 antibodies can be used diagnostically in immuno-precipitation and immuno-blotting to detect and evaluate Delta3 protein levels in tissue as part of a clinical testing procedure. For instance, such measurements can be useful in predictive valuations of the onset or progression of neurodegenerative, neoplastic or hyperplastic disorders. Likewise, the ability to monitor Delta3 protein levels in an individual can allow determination of the efficacy of a given treatment regimen for an individual afflicted with such a disorder. The level of Delta3 polypeptides may be measured from cells in bodily fluid, such as in samples of cerebral spinal fluid or amniotic fluid, or can be measured in tissue, such as produced by biopsy. Diagnostic assays using anti-Delta3 antibodies can include, for example, immunoassays designed to aid in early diagnosis of a neurodegenerative disorder, particularly ones which are manifest at birth. Diagnostic assays using anti-Delta3 polypeptide antibodies can also include immunoassays designed to aid in early diagnosis and phenotyping neurodegenerative, neoplastic or hyperplastic disorders.

Another application of anti-Delta3 antibodies of the present invention is in the immunological screening of cDNA libraries constructed in expression vectors such as λgt11, λgt18–23, λZAP, and ORF8. Messenger libraries of this type, having coding sequences inserted in the correct reading frame and orientation, can produce fusion proteins. For instance, λgt11 will produce fusion proteins whose amino termini consist of β-galactosidase amino acid sequences and whose carboxy termini consist of a foreign polypeptide. Antigenic epitopes of a Delta3 protein, e.g. other orthologs of a particular Delta3 protein or other paralogs from the same species, can then be detected with antibodies, as, for example, reacting nitrocellulose filters lifted from infected plates with anti-Delta3 antibodies. Positive phage detected by this assay can then be isolated from the infected plate. Thus, the presence of Delta3 homologs can be detected and cloned from other animals, as can alternate isoforms (including splicing variants) from humans.

4.5 Methods of Treating Disease

Based at least in part on the fact that the Notch signaling pathway has been implicated in development of the nervous system, in particular in regulating neuronal differentiation and vasculature, e.g., CNS vasculature, a wide variety of pathological diseases or conditions can benefit from treatment with Delta3 therapeutics. In particular, based at least in part on the observation that PS1 and PS2, genes encoding amyloid precursor proteins, which are mutated in about 10% of cases of Alzheimer's disease, are functionally linked to the Notch signaling pathway, mutations in genes of the Notch signaling pathway, e.g., Delta genes, could also result in Alzheimer's disease or other neurodegenerative or neurodevelopmental diseases. The Notch signaling pathway plays a role in the development of vasculature. For example, loss of Dll1 function mutants become severally hemorrhagic after embryonic day 10. Furthermore, mutations in Notch3 result in CADASIL, a disease characterized by stroke. In addition, mice with a functionally ablated PS1 gene exhibit haemorages in the brain and/or spinal cord after embryonic day 11.5 (Wong et al., supra). Furthermore, since the Notch signaling pathway is involved in cell fate determination at least in the nervous system and endothelial system, it is likely that the Notch signaling pathway, and in particular Delta3 is involved in cell fate determination in additional biological systems. Accordingly, the invention also provides methods for treating diseases or disorders arising from an abnormal cell proliferation and/or differentiation of cells other than cells from the nervous system and vasculature.

Preferred disorders that can be treated or prevented according to the methods of the invention include pathological neurogenic, neoplastic or hyperplastic conditions. Neurologic diseases, e.g., neurodegenerative, neurodifferentiative and neurodevelopmental diseases, that might benefit from this methodology include, but are not limited to neuropathies, e.g., peripheral neuropathy such as ACCPN, stroke, dementia, e.g. cerebral autosomal dominant arteriopathy with subcortical infarcts and leukoencephalopathy (CADASIL), degenerative lesions (Parkinson's disease, Alzheimer's disease, Huntington's chorea, amyotrophic lateral sclerosis, spinocerebellar degenerations), demyelating diseases (multiple sclerosis, human immunodeficiency associated myelophathy, transverse myelopathy, progressive multifocal leukoencephalopathy, pontine myelinolysis), motor neuron injuries, progressive spinal muscular atrophy, progressive bulbar palsy, primary lateral sclerosis, infantile and juvenile muscular atrophy, progressive bulbar paralysis of childhood (Fazio-Londe syndrome), poliomyelitis, and hereditary motorsensory neuropathy (Charcot-Marie-Tooth disease), spinal cord injuries, brain injuries, lesions associated with surgery, ischemic lesions, malignant lesions, infectious lesions.

Even more preferred neurological diseases that can be treated according to the method of the invention include neuropathies, e.g, peripheral neuropathies, e.g., Agenesis of the Corpus Callosum with Peripheral Neuropathy (ACCPN). In fact, as set forth in Example, 5.5., hDelta3 has been mapped to human chromosome 15 close to framework markers D15S1244 and D15S144, a chromosomal region which has been shown to be genetically linked (ACCPN) (Casaubon et al., supra). The disease is characterized by a progressive peripheral neuropathy caused by axonal degeneration and a central nervous system (CNS) malformation characterized by the absence of hypoplasia of the corpus callosum. The disorder appears early in life, is progressive and results in death in the third decade of life of the subject.

Neuropathies refer to disorders of peripheral nerves and includes both motor and sensory functions, since most motor and sensory axons run in the same nerves. Neurophathies may be either chronic or acute. One example of a acute neuropathy is the Guillain-Barre syndrome, which often follow respiratory infection. Chronic neuropathies include, e.g., acute intermittent porphyria, Charcot-Marie-Tooth disease, metabolic diseases such as diabetes and B12 deficiency, intoxication, nutritional disorders.

Disorders of the vasculature, also termed "vascular disorders", in addition to CADASIL and stroke, that can be treated or prevented according to the methods of the invention include atheroma, tumor angiogenesis, wound healing, diabetic retinopathy, hamangioma, psoriasis, and restenosis, e.g., restenosis resulting from balloon angioplasty.

In one embodiment, diseases or disorders caused or contributed to by aberrant Delta3 activity, such as aberrant Delta3 protein levels or an aberrant biological activity or which are associated with one or more specific Delta3 alleles, e.g., a mutant Delta3 allele, can be treated with Delta3 therapeutics. Aberrant protein levels can be caused, e.g., by aberrant gene expression. Such aberrant activity can result, for example, in aberrant cell proliferation and/or differentiation or cell death. For example, aberrant Delta3 activity in a subject can result in increased proliferation of certain cells in the subject. Subjects having a disorder characterized by abnormal cell proliferation can be treated by administration of a Delta3 therapeutic inhibiting or decreasing such proliferation. The specific Delta3 therapeutic used may vary depending on the type of the cell that is proliferating aberrantly. The appropriate Delta3 therapeutic to use can be determined, e.g., by in vitro culture of a sample of such cells which can be obtained from the subject, in the presence and in the absence of Delta3 therapeutics.

Diseases or conditions associated with aberrant cell proliferation which can be treated or prevented with Delta3 therapeutics include cancers, malignant conditions, premalignant conditions, benign conditions. The condition to be treated or prevented can be a solid tumor, such as a tumor arising in an epithelial tissue. For example, the cancer can be colon or cervix cancer. Cancer of the colon and cervix have in fact been found to have increased levels of expression of Notch as compared to normal tissue (PCT Application WO/07474). Accordingly, treatment of such a cancer could comprise administration to the subject of a Delta3 therapeutic decreasing the interaction of Notch with Delta3. Other cancers that can be treated or prevented with a Delta3 protein include sarcomas and carcinomas, e.g., lung cancer, cancer of the esophagus, lung cancer, melanoma, seminoma, and squamous adenocarcinoma. Additional solid tumors within the scope of the invention include those that can be found in a medical textbook. The condition to be treated or prevented can also be a soluble tumor, such as leukemia, either chronic or acute, including chronic or acute myelogenous leukemia, chronic or acute lymphocytic leukemia, promyelocytic leukemia, monocytic leukemia, myelomonocytic leukemia, and erythroleukemia. Yet other proliferative disorders that can be treated with a Delta3 therapeutic of the invention include heavy chain disease, multiple myeloma, lymphoma, e.g., Hodgkin's lymphoma and non-Hodgkin's lymphoma, Waldenstroem's macroglobulemia, and fibroproliferative disorders, particularly of cerebravascular tissue.

Diseases or conditions characterized by a solid or soluble tumor can be treated by administrating a Delta3 therapeutic either locally or systemically, such that proliferation of the cells having an aberrant proliferation is inhibited or decreased. Methods for administering the compounds of the invention are further described below.

The invention also provides methods for preventing the formation and/or development of tumors. For example, the development of a tumor can be preceded by the presence of a specific lesion, such as a pre-neoplastic lesion, e.g., hyperplasia, metaplasia, and dysplasia. Such lesions can be found, e.g., in epithelial tissue. Thus, the invention provides a method for inhibiting progression of such a lesion into a neoplastic lesion, comprising administering to the subject having a preneoplastic lesion a amount of a Delta3 therapeutic sufficient to inhibit progression of the preneoplastic lesion into a neoplastic lesion.

In a preferred embodiment, the invention provides a method for inhibiting endothelial cell proliferation and/or differentiation, comprising contacting a Delta3 therapeutic with a tissue in which endothelial cells are proliferating, such as a developing tumor or a hyperproliferative disease, i.e., a disease associated with abnormal cellular proliferation. Blocking the proliferation of endothelial cells will result in inhibition of development of endothelium and blood vessels, thus limiting access to the tumor of compounds necessary for tumor development.

The invention also provides for methods for treating or preventing diseases or conditions associated with insufficient cell proliferation. For example, Delta3 therapeutics can be used to stimulate tissue repair, regeneration, and/or wound healing, e.g. of neural tissue, such as after surgery or to stimulate tissue healing from burns. Other disease in which proliferation of cells is desired are hypoproliferative diseases, i.e., diseases characterized by an abnormally low proliferation of certain cells.

In yet another embodiment, the invention provides a method for treating or preventing diseases or conditions characterized by aberrant cell differentiation. Accordingly, the invention provides methods for stimulating cellular differentiation in conditions characterized by an inhibition of normal cell differentiation which may or may not be accompanied by excessive proliferation. Alternatively, Delta3 therapeutics can be used to inhibit differentiation of specific cells.

In a preferred method, the aberrantly proliferating and/or differentiating cell is a cell present in the nervous system. Accordingly, the invention provides methods for treating diseases or conditions associated with a central or peripheral nervous system. For example, the invention provides methods for treating lesions of the nervous system involving an aberrant Delta3 activity in neurons, in Schwann cells, glial cells, or other types of neural cells. Disorders of the nervous system are set forth above.

In another embodiment, the invention provides a method for enhancing the survival and/or stimulating proliferation and/or differentiation of cells and tissues in vitro. For example, tissues from a subject can be obtained and grown in vitro in the presence of a Delta3 therapeutic, such that the tissue cells are stimulated to proliferate and/or differentiate. The tissue can then be readministered to the subject.

Since, in some cases, genes may be upregulated in a disease state and in other cases may be downregulated, it will be desirable to activate and/or potentiate or suppress and/or downmodulate Delta3 bioactivity depending on the condition to be treated using the techniques compounds and methods described herein. Some genes may be underexpressed in certain disease states. The activity of Delta3 gene products may be in some way impaired, leading to the development of neurodegenerative disease symptoms. Such down-regulation of Delta3 gene expression or decrease in the activity of a Delta3 protein may have a causative or exacerbating effect on the disease state.

Among the approaches which may be used to ameliorate disease symptoms involving the misexpression of a Delta3 gene are, for example, antisense, ribozyme, and triple helix molecules described above. Compounds that compete with a Delta3 protein for binding to upstream or downstream elements in a Delta/Notch signaling cascade will antagonize a Delta3 protein, thereby inducing a therapeutic effect. Examples of suitable compounds include the antagonists or homologues described in detail above. In other instances, the increased expression or bioactivity of a Delta3 protein may be desirable and may be accomplished by, for example the use of the Delta3 agonists or mimetics or by gene replacement therapy, as described herein.

Yet other Delta3 therapeutics consist of a first peptide comprising a Delta3 peptide capable of binding to a receptor, e.g., a Notch receptor, and a second peptide which is cytotoxic. Such therapeutics can be used to specifically target and lyse cells expressing or overexpressing a receptor for Delta3. For example, a fusion protein containing a Delta3 peptide fused to a cytotoxic peptide can be used to eliminate or reduce a tumor overexpressing Notch, e.g., colon and cervix neoplastic tumors. Alternatively, cells expressing or overexpressing Delta3 can be targeted for lysis, by, for example, targeting to the cell an antibody binding specifically to a Delta3 protein linked to a cytotoxic peptide.

Based at least in part on the similarity of protein structure, it is likely that Delta3 therapeutics can also be used to treat diseases or conditions caused by or contributed by an aberrant Delta activity, e.g., an aberrant Delta1 or Delta2 activity or diseases or disorders which are associated with one or more specific Delta alleles, e.g., Delta1 or Delta2 allelles. Such diseases or conditions could include neurological diseases and cancer. Similarly, Delta therapeutics, e.g., Delta1 or Delta2 therapeutics, could be used to prevent or treat diseases or disorders caused by or contributed to by an aberrant Delta3 activity, or diseases or disorders which are associated with a specific Delta3 allele. Delta therapeutics can be prepared using, e.g, the nucleotide and protein sequence information disclosed in the PCT Patent Application WO 97/01571 and tested using the assays described herein for testing Delta3 therapeutics.

Compounds identified as increasing or decreasing Delta3 gene expression or protein activity can be administered to a subject at therapeutically effective dose to treat or ameliorate cardiovascular disease. A therapeutically effective dose refers to that amount of the compound sufficient to result in amelioration of symptoms associated with the particular disease.

4.5.1. Effective Dose

Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds which exhibit large therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the EDSO with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the $IC_{50}$ (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

5.2. Formulation and Use

Pharmaceutical compositions for use in accordance with the present invention may be formulated in conventional manner using one or more physiologically acceptable carriers or excipients. Thus, the compounds and their physiologically acceptable salts and solvates may be formulated for administration by, for example, injection, inhalation or insufflation (either through the mouth or the nose) or oral, buccal, parenteral or rectal administration.

For such therapy, the oligomers of the invention can be formulated for a variety of loads of administration, including systemic and topical or localized administration. Techniques and formulations generally may be found in Remmington's Pharmaceutical Sciences, Meade Publishing Co., Easton, Pa. For systemic administration, injection is preferred, including intramuscular, intravenous, intraperitoneal, and subcutaneous. For injection, the oligomers of the invention can be formulated in liquid solutions, preferably in physiologically compatible buffers such as Hank's solution or Ringer's solution. In addition, the oligomers may be formulated in solid form and redissolved or suspended immediately prior to use. Lyophilized forms are also included.

For oral administration, the pharmaceutical compositions may take the form of, for example, tablets or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations may also contain buffer salts, flavoring, coloring and sweetening agents as appropriate.

Preparations for oral administration may be suitably formulated to give controlled release of the active compound.

For buccal administration the compositions may take the form of tablets or lozenges formulated in conventional manner.

For administration by inhalation, the compounds for use according to the present invention are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g. gelatin for use in an inhaler or insufflator may be formulated containing a powder mix of the compound and a suitable powder base such as lactose or starch.

The compounds may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g., sterile pyrogen-free water, before use.

The compounds may also be formulated in rectal compositions such as suppositories or retention enemas, e.g., containing conventional suppository bases such as cocoa butter or other glycerides.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration bile salts and fusidic acid derivatives. In addition, detergents may be used to facilitate permeation. Transmucosal administration may be through nasal sprays or using suppositories. For topical administration, the oligomers of the invention are formulated into ointments, salves, gels, or creams as generally known in the art.

In clinical settings, the gene delivery systems for the therapeutic Delta3 gene can be introduced into a patient by any of a number of methods, each of which is familiar in the art. For instance, a pharmaceutical preparation of the gene delivery system can be introduced systemically, e.g. by intravenous injection, and specific transduction of the protein in the target cells occurs predominantly from specificity of transfection provided by the gene delivery vehicle, cell-type or tissue-type expression due to the transcriptional regulatory sequences controlling expression of the receptor gene, or a combination thereof. In other embodiments, initial delivery of the recombinant gene is more limited with introduction into the animal being quite localized. For example, the gene delivery vehicle can be introduced by catheter (see U.S. Pat. No. 5,328,470) or by stereotactic injection (e.g. Chen et al. (1994) PNAS 91: 3054–3057). A Delta3 gene, such as any one of the sequences represented in the group consisting of SEQ ID NO: 1 or 3, or a sequence homologous thereto can be delivered in a gene therapy construct by electroporation using techniques described, for example, by Dev et al. ((1994) Cancer Treat Rev 20:105–115).

The pharmaceutical preparation of the gene therapy construct can consist essentially of the gene delivery system in an acceptable diluent, or can comprise a slow release matrix in which the gene delivery vehicle is imbedded. Alternatively, where the complete gene delivery system can be produced intact from recombinant cells, e.g. retroviral vectors, the pharmaceutical preparation can comprise one or more cells which produce the gene delivery system.

The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration.

4.6 Diagnostic and Prognostic Assays

The present methods provides means for determining if a subject is at risk of developing a disorder characterized by an aberrant Delta3 activity, such as aberrant cell proliferation, degeneration, and/or differentiation resulting for example in a neurodegenerative disease or cancer. The invention also provides methods for determining whether a subject is at risk of developing a disease or disorder associated with one or more specific alleles of a Delta3 gene. In fact, specific Delta3 alleles may be associated with specific diseases or disorders. For example, at least one allele of hDelta3 is likely to be associated with the neurological disease ACCPN. Accordingly, the invention provides methods for determining whether a subject has or is at risk of developing a neurological disease, e.g., ACCPN. In another embodiment, the invention provides methods for determining whether a subject has or is at risk of developing a vascular disorder or a disorder associated with cell fate determination. In one embodiment, the invention comprises determining the identity of the Delta3 allele in a subject and comparing the molecular structure of the Delta3 gene of the subject with the molecular structure of a Delta3 gene from a subject which does not have the neurological disease. Determining the molecular structure can be, e.g., determining the identity of at least one nucleotide, determining the nucleotide composition or determining the methylation pattern of the gene.

In one embodiment, the invention provides a method for determining whether a subject has genetic lesion in a Delta3 gene or a specific allelic variant of a polymorphic region in a Delta3 gene. The specific allele can be a mutant allele. In another embodiment, the invention provides methods for determining whether a subject has an aberrant Delta3 protein, resulting from aberrant post-translational modifications of the protein, such as aberrant phosphorogulation or glycosylation. Also, within the scope of the invention are methods for determining whether a subject has an aberrant expression level of a Delta3 protein, which could be due to a genetic lesion in the Delta3 gene or due to an aberrant level or activity of a protein regulating the expression of a Delta3 gene.

In preferred embodiments, the methods can be characterized as comprising detecting, in a sample of cells from the subject, the presence or absence of a genetic lesion characterized by at least one of (i) an alteration affecting the integrity of a gene encoding a Delta-protein, or (ii) the mis-expression of a Delta3 gene. To illustrate, such genetic lesions can be detected by ascertaining the existence of at least one of (i) a deletion of one or more nucleotides from a Delta3 gene, (ii) an addition of one or more nucleotides to a Delta3 gene, (iii) a substitution of one or more nucleotides of a Delta3 gene, (iv) a gross chromosomal rearrangement of a Delta3 gene, (v) a gross alteration in the level of a messenger RNA transcript of a Delta3 gene, (vii) aberrant modification of a Delta3 gene, such as of the methylation pattern of the genomic DNA, (vii) the presence of a non-wild type splicing pattern of a messenger RNA transcript of a Delta3 gene, (viii) a non-wild type level of a Delta-protein, (ix) allelic loss of a Delta3 gene, and (x) inappropriate post-translational modification of a Delta-protein. As set out below, the present invention provides a large number of assay techniques for detecting lesions in a Delta3 gene, and importantly, provides the ability to discern between different molecular causes underlying Delta-dependent aberrant cell proliferation and/or differentiation.

For determining whether a subject has or is at risk of developing a disease or condition associated with a specific allele of a Delta3 gene, preliminary experiments can be performed to determine the identity of the allele associated with a disease. For example, for determining the identity of the hDelta3 allele associated with ACCPN, one can perform mutation detection studies of the Delta3 gene in populations having a high risk of developing ACCPN. For example, one can perform mutation detection analysis of the genomic DNA from subjects in the French Canadian population in the Charlevoix and Saguenay-Lac St Jean regions of the province of Quebec (Casaubon et al., supra). Such an analysis will reveal the identity of the Delta3 allele or alleles associated with ACCPN. Comparison of the Delta3 allele of a subject with this allele or alleles associated with ACCPN will indicate whether a subject has a Delta3 allele associated with ACCPN and thus whether the subject has or is likely to develop ACCPN. Similarly, mutation detection analysis can also be carried out to determine the identity of Delta3 alles associated with other diseases or conditions.

In an exemplary embodiment, there is provided a nucleic acid composition comprising a (purified) oligonucleotide probe including a region of nucleotide sequence which is capable of hybridizing to a sense or antisense sequence of a Delta3 gene, such as represented by any of SEQ ID Nos: 1 and 3, alleles thereof, naturally occurring mutants thereof, or 5' or 3' flanking sequences or intronic sequences naturally associated with the subject Delta3 genes or naturally occurring mutants thereof. The nucleic acid of a cell is rendered accessible for hybridization, the probe is exposed to nucleic acid of the sample, and the hybridization of the probe to the sample nucleic acid is detected. Such techniques can be used to detect lesions at either the genomic or mRNA level, including deletions, substitutions, etc., as well as to determine mRNA transcript levels.

As set out above, one aspect of the present invention relates to diagnostic assays for determining, in the context of cells isolated from a patient, if mutations have arisen in one or more Delta3 genes of the sample cells. The present method provides a method for determining if a subject is at risk for a disorder characterized by aberrant Delta3 activity, e.g., cell proliferation and/or differentiation. In preferred embodiments, the method can be generally characterized as comprising detecting, in a sample of cells from the subject, the presence or absence of a genetic lesion characterized by an alteration affecting the integrity of a gene encoding a Delta protein. To illustrate, such genetic lesions can be detected by ascertaining the existence of at least one of (i) a deletion of one or more nucleotides from a Delta-gene, (ii) an addition of one or more nucleotides to a Delta-gene, (iii) a substitution of one or more nucleotides of a Delta-gene, and (iv) the presence of a non-wild type splicing pattern of a messenger RNA transcript of a Delta-gene. As set out below, the present invention provides a large number of assay techniques for detecting lesions in Delta3 genes, and importantly, provides the ability to discern between different molecular causes underlying Delta-dependent aberrant cell proliferation and/or differentiation.

In certain embodiments, detection of the lesion in a Delta gene or the identity of an allelic variant of a polymorphic region of a Delta gene comprises utilizing the probe/primer in a polymerase chain reaction (PCR) (see, e.g. U.S. Pat. Nos. 4,683,195 and 4,683,202), such as anchor PCR or RACE PCR, or, alternatively, in a ligation chain reaction (LCR) (see, e.g., Landegran et al. (1988) Science 241:1077–1080; and Nakazawa et al. (1994) PNAS 91:360–364), the latter of which can be particularly useful for detecting point mutations in the Delta-gene (see Abravaya et al. (1995) Nuc Acid Res 23:675–682). In a merely illustrative embodiment, the method includes the steps of (i) collecting a sample of cells from a patient, (ii) isolating nucleic acid (e.g., genomic, mRNA or both) from the cells of the sample, (iii) contacting the nucleic acid sample with one or more primers which specifically hybridize to a Delta gene under conditions such that hybridization and amplification of the Delta-gene (if present) occurs, and (iv) detecting the presence or absence of an amplification product, or detecting the size of the amplification product and comparing the length to a control sample. It is anticipated that PCR and/or LCR may be desirable to use as a preliminary amplification step in conjunction with any of the techniques used for detecting mutations described herein.

Alternative amplification methods include: self sustained sequence replication (Guatelli, J. C. et al., 1990, Proc. Natl. Acad. Sci. USA 87:1874–1878), transcriptional amplification system (Kwoh, D. Y. et al., 1989, Proc. Natl. Acad. Sci. USA 86:1173–1177), Q-Beta Replicase (Lizardi, P.M. et al., 1988, Bio/Technology 6:1197), or any other nucleic acid amplification method, followed by the detection of the amplified molecules using techniques well known to those of skill in the art. These detection schemes are especially useful for the detection of nucleic acid molecules if such molecules are present in very low numbers.

In a preferred embodiment of the subject assay, mutations in a Delta3 gene or specific alleles of a Delta3 gene from a sample cell are identified by alterations in restriction enzyme cleavage patterns. For example, sample and control DNA is isolated, amplified (optionally), digested with one or more restriction endonucleases, and fragment length sizes are determined by gel electrophoresis. Moreover, the use of sequence specific ribozymes (see, for example, U.S. Pat. No. 5,498,531) can be used to score for the presence of specific mutations by development or loss of a ribozyme cleavage site.

In yet another embodiment, any of a variety of sequencing reactions known in the art can be used to directly sequence the Delta3 gene and detect mutations or allelic variants of polymorphic regions by comparing the sequence of the sample Delta3 with the corresponding wild-type (control) sequence. Exemplary sequencing reactions include those based on techniques developed by Maxim and Gilbert (Proc. Natl Acad Sci USA (1977) 74:560) or Sanger (Sanger et al (1977) Proc. Nat. Acad. Sci 74:5463). It is also contemplated that any of a variety of automated sequencing procedures may be utilized when performing the subject assays (Biotechniques (1995) 19:448), including by sequencing by mass spectrometry (see, for example PCT publication WO 94/16101; Cohen et al. (1996) Adv Chromatogr 36:127–162; and Griffin et al. (1993) Appl Biochem Biotechnol 38:147–159). It will be evident to one skilled in the art that, for certain embodiments, the occurrence of only one, two or three of the nucleic acid bases need be determined in the sequencing reaction. For instance, A-tract or the like, e.g., where only one nucleic acid is detected, can be carried out.

In a further embodiment, protection from cleavage agents (such as a nuclease, hydroxylamine or osmium tetroxide and with piperidine) can be used to detect mismatched bases in RNA/RNA or RNA/DNA heteroduplexes (Myers, et al. (1985) Science 230:1242). In general, the art technique of "mismatch cleavage" starts by providing heteroduplexes of formed by hybridizing (labelled) RNA or DNA containing the wild-type Delta3 sequence with potentially mutant RNA or DNA obtained from a tissue sample. The double-stranded duplexes are treated with an agent which cleaves single-stranded regions of the duplex such as which will exist due to basepair mismatches between the control and sample strands. For instance, RNA/DNA duplexes can be treated with RNase and DNA/DNA hybrids treated with S1 nuclease to enzymatically digesting the mismatched regions. In other embodiments, either DNA/DNA or RNA/DNA duplexes can be treated with hydroxylamine or osmium tetroxide and with piperidine in order to digest mismatched regions. After digestion of the mismatched regions, the resulting material is then separated by size on denaturing polyacrylamide gels to determine the site of mutation. See, for example, Cotton et al (1988) Proc. Natl Acad Sci USA 85:4397; Saleeba et al (1992) Methods Enzymod. 217:286–295. In a preferred embodiment, the control DNA or RNA can be labeled for detection.

In still another embodiment, the mismatch cleavage reaction employs one or more proteins that recognize mismatched base pairs in double-stranded DNA (so called "DNA mismatch repair" enzymes) in defined systems for detecting and mapping point mutations in Delta3 cDNAs obtained from samples of cells. For example, the mutY enzyme of *E. coli* cleaves A at G/A mismatches and the thymidine DNA glycosylase from HeLa cells cleaves T at G/T mismatches (Hsu et al. (1994) Carcinogenesis 15:1657–1662). According to an exemplary embodiment, a probe based on a Delta3 sequence, e.g., a wild-type Delta3 sequence, is hybridized to a cDNA or other DNA product from a test cell(s). The duplex is treated with a DNA mismatch repair enzyme, and the cleavage products, if any, can be detected from electrophoresis protocols or the like. See, for example, U.S. Pat. No. 5,459,039.

In other embodiments, alterations in electrophoretic mobility will be used to identify mutations in Delta3 genes or for determining the identity of the Delta3 allele. For example, single strand conformation polymorphism (SSCP) may be used to detect differences in electrophoretic mobility between mutant and wild type nucleic acids (Orita et al. (1989) Proc Natl. Acad. Sci USA 86:2766, see also Cotton (1993) Mutat Res 285:125–144; and Hayashi (1992) Genet Anal Tech Appl 9:73–79). Single-stranded DNA fragments of sample and control Delta3 nucleic acids will be denatured and allowed to renature. The secondary structure of single-stranded nucleic acids varies according to sequence, the resulting alteration in electrophoretic mobility enables the detection of even a single base change. The DNA fragments may be labelled or detected with labelled probes. The sensitivity of the assay may be enhanced by using RNA (rather than DNA), in which the secondary structure is more sensitive to a change in sequence. In a preferred embodiment, the subject method utilizes heteroduplex analysis to separate double stranded heteroduplex molecules on the basis of changes in electrophoretic mobility (Keen et al. (1991) Trends Genet 7:5).

In yet another embodiment the movement of mutant or wild-type fragments in polyacrylamide gels containing a gradient of denaturant is assayed using denaturing gradient gel electrophoresis (DGGE) (Myers et al (1985) Nature 313:495). When DGGE is used as the method of analysis, DNA will be modified to insure that it does not completely denature, for example by adding a GC clamp of approximately 40 bp of high-melting GC-rich DNA by PCR. In a further embodiment, a temperature gradient is used in place of a denaturing agent gradient to identify differences in the mobility of control and sample DNA (Rosenbaum and Reissner (1987) Biophys Chem 265:12753).

Examples of other techniques for detecting point mutations include, but are not limited to, selective oligonucleotide hybridization, selective amplification, or selective primer extension. For example, oligonucleotide primers may be prepared in which the known mutation is placed centrally and then hybridized to target DNA under conditions which permit hybridization only if a perfect match is found (Saiki et al. (1986) Nature 324:163); Saiki et al (1989) Proc. Natl Acad. Sci USA 86:6230). Such allele specific oligonucleotide hybridization techniques may be used to test one mutation per reaction when oligonucleotides are hybridized to PCR amplified target DNA or a number of different mutations when the oligonucleotides are attached to the hybridizing membrane and hybridized with labelled target DNA.

Alternatively, allele specific amplification technology which depends on selective PCR amplification may be used in conjunction with the instant invention. Oligonucleotides used as primers for specific amplification may carry the mutation of interest in the center of the molecule (so that amplification depends on differential hybridization) (Gibbs et al (1989) Nucleic Acids Res. 17:2437–2448) or at the extreme 3' end of one primer where, under appropriate conditions, mismatch can prevent, or reduce polymerase extension (Prossner (1993) Tibtech 11:238. In addition it may be desirable to introduce a novel restriction site in the region of the mutation to create cleavage-based detection (Gasparini et al (1992) Mol. Cell Probes 6:1). It is anticipated that in certain embodiments amplification may also be performed using Taq ligase for amplification (Barany (1991) Proc. Natl. Acad. Sci USA 88:189). In such cases, ligation will occur only if there is a perfect match at the 3' end of the 5' sequence making it possible to detect the presence of a known mutation at a specific site by looking for the presence or absence of amplification.

Another embodiment of the invention provides for a nucleic acid composition comprising a (purified) oligonucleotide probe including a region of nucleotide sequence which is capable of hybridizing to a sense or antisense sequence of a Delta-gene, or naturally occurring mutants thereof, or 5' or 3' flanking sequences or intronic sequences naturally associated with the subject Delta-genes or naturally occurring mutants thereof. The nucleic acid of a cell is rendered accessible for hybridization, the probe is exposed to nucleic acid of the sample, and the hybridization of the probe to the sample nucleic acid is detected. Such techniques can be used to detect lesions at either the genomic or mRNA level, including deletions, substitutions, etc., as well as to determine mRNA transcript levels. Such oligonucleotide probes can be used for both predictive and therapeutic evaluation of allelic mutations which might be manifest in, for example, a neurodegenerative, neoplastic or hyperplastic disorders (e.g. aberrant cell growth).

The methods described herein may be performed, for example, by utilizing pre-packaged diagnostic kits comprising at least one probe nucleic acid or antibody reagent described herein, which may be conveniently used, e.g., in clinical settings to diagnose patients exhibiting symptoms or family history of a disease or illness involving a Delta3 gene.

Any cell type or tissue, preferably neural or endothelial cells, in which the Delta3 is expressed may be utilized in the diagnostics described below. For example, a subject's bodily fluid (e.g. blood) can be obtained by known techniques (e.g. venipuncture). Alternatively, nucleic acid tests can be performed on dry samples (e.g. hair or skin). Fetal nucleic acid samples can be obtained from maternal blood as described in International Patent Application No. WO91/07660 to Bianchi. Alternatively, amniocytes or chorionic villi may be obtained for performing prenatal testing, e.g., of ACCPN, which is a disease which is usually fatal in the third decade of life.

Diagnostic procedures may also be performed in situ directly upon tissue sections (fixed and/or frozen) of patient tissue obtained from biopsies or resections, such that no nucleic acid purification is necessary. Nucleic acid reagents may be used as probes and/or primers for such in situ procedures (see, for example, Nuovo, G. J., 1992, PCR in situ hybridization: protocols and applications, Raven Press, NY).

In addition to methods which focus primarily on the detection of one nucleic acid sequence, profiles may also be assessed in such detection schemes. Fingerprint profiles may be generated, for example, by utilizing a differential display procedure, Northern analysis and/or RT-PCR.

Antibodies directed against wild type or mutant Delta3 proteins, which are discussed, above, may also be used in disease diagnostics and prognostics. Such diagnostic methods, may be used to detect abnormalities in the level of Delta3 protein expression, or abnormalities in the structure and/or tissue, cellular, or subcellular location of Delta3 proteins. Structural differences may include, for example, differences in the size, electronegativity, or antigenicity of the mutant Delta3 protein relative to the normal Delta3 protein. Protein from the tissue or cell type to be analyzed may easily be detected or isolated using techniques which are well known to one of skill in the art, including but not limited to western blot analysis. For a detailed explanation of methods for carrying out western blot analysis, see Sambrook et al, 1989, supra, at Chapter 18. The protein detection and isolation methods employed herein may also be such as those described in Harlow and Lane, for example, (Harlow, E. and Lane, D., 1988, "Antibodies: A Laboratory Manual", Cold Spring Harbor Laboratory Press, Cold Spring Harbor, New York), which is incorporated herein by reference in its entirety.

This can be accomplished, for example, by immunofluorescence techniques employing a fluorescently labeled antibody (see below) coupled with light microscopic, flow cytometric, or fluorimetric detection. The antibodies (or fragments thereof) useful in the present invention may, additionally, be employed histologically, as in immunofluorescence or immunoelectron microscopy, for in situ detection of Delta3 proteins. In situ detection may be accomplished by removing a histological specimen from a patient, and applying thereto a labeled antibody of the present invention. The antibody (or fragment) is preferably applied by overlaying the labeled antibody (or fragment) onto a biological sample. Through the use of such a procedure, it is possible to determine not only the presence of the Delta3 protein, but also its distribution in the examined tissue. Using the present invention, one of ordinary skill will readily perceive that any of a wide variety of histological methods (such as staining procedures) can be modified in order to achieve such in situ detection.

Often a solid phase support or carrier is used as a support capable of binding an antigen or an antibody. Well-known supports or carriers include glass, polystyrene, polypropylene, polyethylene, dextran, nylon, amylases, natural and modified celluloses, polyacrylamides, gabbros, and magnetite. The nature of the carrier can be either soluble to some extent or insoluble for the purposes of the present invention. The support material may have virtually any possible structural configuration so long as the coupled molecule is capable of binding to an antigen or antibody. Thus, the support configuration may be spherical, as in a bead, or cylindrical, as in the inside surface of a test tube, or the external surface of a rod. Alternatively, the surface may be flat such as a sheet, test strip, etc. Preferred supports include polystyrene beads. Those skilled in the art will know many other suitable carriers for binding antibody or antigen, or will be able to ascertain the same by use of routine experimentation.

One means for labeling an anti-Delta3 protein specific antibody is via linkage to an enzyme and use in an enzyme immunoassay (EIA) (Voller, "The Enzyme Linked Immunosorbent Assay (ELISA)", Diagnostic Horizons 2:1–7, 1978, Microbiological Associates Quarterly Publication, Walkersville, Md.; Voller, et al., J. Clin. Pathol. 31:507–520 (1978); Butler, Meth. Enzymol. 73:482–523 (1981); Maggio, (ed.) Enzyme Immunoassay, CRC Press, Boca Raton, Fla., 1980; Ishikawa, et al., (eds.) Enzyme Immunoassay, Kgaku Shoin, Tokyo, 1981). The enzyme which is bound to the antibody will react with an appropriate substrate, preferably a chromogenic substrate, in such a manner as to produce a chemical moiety which can be detected, for example, by spectrophotometric, fluorimetric or by visual means. Enzymes which can be used to detectably label the antibody include, but are not limited to, malate dehydrogenase, staphylococcal nuclease, delta-5-steroid isomerase, yeast alcohol dehydrogenase, alpha-glycerophosphate, dehydrogenase, triose phosphate isomerase, horseradish peroxidase, alkaline phosphatase, asparaginase, glucose oxidase, beta-galactosidase, ribonuclease, urease, catalase, glucose-6-phosphate dehydrogenase, glucoamylase and acetylcholinesterase. The detection can be accomplished by colorimetric methods which employ a chromogenic substrate for the enzyme. Detection may also be accomplished by visual comparison of the extent of enzymatic reaction of a substrate in comparison with similarly prepared standards.

Detection may also be accomplished using any of a variety of other immunoassays. For example, by radioactively labeling the antibodies or antibody fragments, it is possible to detect fingerprint gene wild type or mutant peptides through the use of a radioimmunoassay (RIA) (see, for example, Weintraub, B., Principles of Radioimmunoassays, Seventh Training Course on Radioligand Assay Techniques, The Endocrine Society, March, 1986, which is incorporated by reference herein). The radioactive isotope can be detected by such means as the use of a gamma counter or a scintillation counter or by autoradiography.

It is also possible to label the antibody with a fluorescent compound. When the fluorescently labeled antibody is exposed to light of the proper wave length, its presence can then be detected due to fluorescence. Among the most commonly used fluorescent labeling compounds are fluorescein isothiocyanate, rhodamine, phycoerythrin, phycocyanin, allophycocyanin, o-phthaldehyde and fluorescamine.

The antibody can also be detectably labeled using fluorescence emitting metals such as $^{152}Eu$, or others of the lanthanide series. These metals can be attached to the antibody using such metal chelating groups as diethylenetriaminepentacetic acid (DTPA) or ethylenediaminetetraacetic acid (EDTA).

The antibody also can be detectably labeled by coupling it to a chemiluminescent compound. The presence of the chemiluminescent-tagged antibody is then determined by detecting the presence of luminescence that arises during the course of a chemical reaction. Examples of particularly useful chemiluminescent labeling compounds are luminol, isoluminol, theromatic acridinium ester, imidazole, acridinium salt and oxalate ester.

Likewise, a bioluminescent compound may be used to label the antibody of the present invention. Bioluminescence is a type of chemiluminescence found in biological systems in, which a catalytic protein increases the efficiency of the chemiluminescent reaction. The presence of a bioluminescent protein is determined by detecting the presence of luminescence. Important bioluminescent compounds for purposes of labeling are luciferin, luciferase and aequorin.

Moreover, it will be understood that any of the above methods for detecting alterations in a Delta3 gene or gene product can be used to monitor the course of treatment or therapy.

4.7. Drug Screening Assays

The invention provides for compounds, e.g., therapeutic compounds, for treating diseases or conditions caused by, or contributed to by an abnormal Delta3 activity. The compounds that can be used for this purpose can be any type of compound, including a protein, a peptide, peptidomimetic, small molecule, and nucleic acid. A nucleic acid can be, e.g., a gene, an antisense nucleic acid, a ribozyme, or a triplex molecule. A compound of the invention can be an agonist or an antagonist. A compound can act on a Delta3 gene, e.g., to modulate its expression. A compound can also act on a Delta3 protein, e.g, to modulate signal transduction from the receptor. Accordingly, a compound of the invention can be a compound which binds to Delta3 and induces signal transduction from the receptor, such that, e.g, a Delta3 activity is induced. Alternatively, a compound of the invention can be a compound which inhibits interaction of a Delta3 protein with a toporythmic protein, e.g., Notch. In one embodiment, a compound of the invention which interacts with a Delta protein, which is either an agonist or an antagonist, is a toporythmic protein or other protein interacting with Delta3. In an even more preferred embodiment, the compound is a soluble toporythmic protein or other protein interacting with Delta3. For example, a soluble antagonistic toporythmic protein can be a protein which competes with the wild type toporythmic proteins for binding to Delta3. A soluble agonistic toporythrnic protein can be a protein which binds to a Delta3 protein in essentially the same manner as a wild-type toporythmic protein, such as to induce at least one Delta3 activity, e.g, signal transduction from the Delta3 protein. Accordingly, a soluble toporythmic protein can be stimulatory form of a toporythmic protein or an inhibitory form of a toporythrnic, depending on whether the particular toporythmic protein stimulates or inhibits a Delta3 activity.

Similarly, a soluble Delta3 protein, e.g., Delta3-Ig, can be used to modulate an activity of a toporythmic protein, e.g., Notch. For example, a soluble Delta3 protein can be a stimulatory form of a Delta3 protein, i.e., a Delta3 protein which is capable of stimulating an activity of a toporythmic protein. In one embodiment, such a protein acts in essentially the same manner as wild-type Delta3. In another embodiment, a soluble Delta3 protein is an inhibitory form of a Delta3 protein, i.e., a Delta3 protein which is capable of inhibiting an activity of a toporythmic protein. For example, such a Delta3 protein could inhibit the interaction of wild-type Delta3 with the toporythmic protein. In a preferred embodiment, an inhibitory form of a Delta3 protein inhibits the interaction of several proteins which normally interact with a toporythmic protein, by, e.g, binding to a site of the toporythmic protein that is also a binding site to various other proteins, e.g, other Delta proteins. Accordingly, a Delta3 therapeutic can generally affect the interaction of various toporythmic proteins with each other. Similarly, based at least in part on the sequence and structural similarities between Delta proteins, a Delta therapeutic, other than a Delta3 therapeutic, can also be used for modulating the interaction between a Delta3 protein and a Delta3 interacting binding molecule.

The compounds of the invention can be identified using various assays depending on the type of compound and activity of the compound that is desired. Set forth below are at least some assays that can be used for identifying Delta3 therapeutics. It is within the skill of the art to design additional assays for identifying Delta therapeutics, e.g., Delta3 therapeutics.

By making available purified and recombinant Delta3 polypeptides, the present invention facilitates the development of assays which can be used to screen for drugs, including Delta3 variants, which are either agonists or antagonists of the normal cellular function of the subject Delta3 polypeptides, or of their role in the pathogenesis of cellular differentiation and/or proliferation and disorders related thereto. In one embodiment, the assay evaluates the ability of a compound to modulate binding between a Delta3 polypeptide and a molecule, be it protein or DNA, that interacts either upstream or downstream of the Delta/Notch signaling pathway. A variety of assay formats will suffice and, in light of the present inventions, will be comprehended by a skilled artisan.

4.7.1 Cell-free assays

Cell free assays can be used to identify compounds which interact with a Delta3 protein. Such assays are available for testing compounds which are proteins, e.g., toporythrnic proteins or variants thereof, as well as for testing compounds which are peptidomimetics, small molecules or nucleic acids. The specific assay used for testing these compounds may vary with the type of compound.

In one embodiment, a compound that interacts with a Delta3 protein is identified by screening, e.g., a library of compounds, for binding to a recombinant or purified Delta3 protein or at least a portion thereof. Such assays can involve labeling one or the two components and measuring the extent of their interaction, by, e.g., determining the level of the one or two labels. In these assays, it may be preferable to attach the Delta3 protein to a solid phase surface. Methods for achieving this are further described infra. In one embodiment, the library of compounds is a library of small molecules. In another embodiment, the library of compounds is a library of Delta3 variants, which can be produced according to methods described infra.

Identification of a compound which inhibits an interaction between a Delta3 protein and a toporythmic protein can also be performed by screening compounds using aggregation assays, as described, e.g., in Fehon et al. (1990) Cell 61:523–534.

In another embodiment, the invention provides methods for identifying compounds which inhibit the interaction of a Delta3 protein with a molecule, e.g., a toporythmic protein or a protein interacting with the cytoplasmic domain of a Delta3 protein. Such methods, which are preferably used in high throughput assays can be peformed as follows.

In many drug screening programs which test libraries of compounds and natural extracts, high throughput assays are desirable in order to maximize the number of compounds surveyed in a given period of time. Assays which are performed in cell-free systems, such as may be derived with purified or semi-purified proteins, are often preferred as "primary" screens in that they can be generated to permit rapid development and relatively easy detection of an alteration in a molecular target which is mediated by a test compound. Moreover, the effects of cellular toxicity and/or bioavailability of the test compound can be generally ignored in the in vitro system, the assay instead being focused primarily on the effect of the drug on the molecular target as may be manifest in an alteration of binding affinity with upstream or downstream elements. Accordingly, in an exemplary screening assay of the present invention, the compound of interest is contacted with proteins which may function upstream (including both activators and repressors of its activity) or to proteins or nucleic acids which may function downstream of the Delta3 polypeptide, whether they are positively or negatively regulated by it. For example, a protein functioning upstream of a Delta3 polypeptide can be a compound interacting with the extracellular portion of the Delta3 molecule. A protein functioning downstream of a Delta3 polypeptide can be a protein interacting with the cytoplasmic domain of Delta3 and, e.g, transducing a signal to the nucleus. To the mixture of the compound and the upstream or downstream element is then added a composition containing a Delta3 polypeptide. Detection and quantification of complexes of Delta3 with it's upstream or downstream elements provide a means for determining a compound's efficacy at inhibiting (or potentiating) complex formation between Delta3 and the Delta-binding elements. The efficacy of the compound can be assessed by generating dose response curves from data obtained using various concentrations of the test compound. Moreover, a control assay can also be performed to provide a baseline for comparison. In the control assay, isolated and purified Delta3 polypeptide is added to a composition containing the Delta-binding element, and the formation of a complex is quantitated in the absence of the test compound.

Complex formation between the Delta3 polypeptide and a Delta3 binding element may be detected by a variety of techniques. Modulation of the formation of complexes can be quantitated using, for example, detectably labeled proteins such as radiolabeled, fluorescently labeled, or enzymatically labeled Delta3 polypeptides, by immunoassay, or by chromatographic detection.

Typically, it will be desirable to immobilize either Delta3 or its binding protein to facilitate separation of complexes from uncomplexed forms of one or both of the proteins, as well as to accommodate automation of the assay. Binding of Delta3 to an upstream or downstream element, in the presence and absence of a candidate agent, can be accomplished in any vessel suitable for containing the reactants. Examples include microtitre plates, test tubes, and micro-centrifuge tubes. In one embodiment, a fusion protein can be provided which adds a domain that allows the protein to be bound to a matrix. For example, glutathione-S-transferase/Delta3 (GST/Delta) fusion proteins can be adsorbed onto glutathione sepharose beads (Sigma Chemical, St. Louis, Mo.) or glutathione derivatized microtitre plates, which are then combined with the cell lysates, e.g. an $^{35}$S-labeled, and the test compound, and the mixture incubated under conditions conducive to complex formation, e.g. at physiological conditions for salt and pH, though slightly more stringent conditions may be desired. Following incubation, the beads are washed to remove any unbound label, and the matrix immobilized and radiolabel determined directly (e.g. beads placed in scintilant), or in the supernatant after the complexes are subsequently dissociated. Alternatively, the complexes can be dissociated from the matrix, separated by SDS-PAGE, and the level of Delta-binding protein found in the bead fraction quantitated from the gel using standard electrophoretic techniques such as described in the appended examples.

Other techniques for immobilizing proteins on matrices are also available for use in the subject assay. For instance, either Delta3 or its cognate binding protein can be immobilized utilizing conjugation of biotin and streptavidin. For instance, biotinylated Delta3 molecules can be prepared from biotin-NHS (N-hydroxy-succinimide) using techniques well known in the art (e.g., biotinylation kit, Pierce Chemicals, Rockford, Ill.), and immobilized in the wells of streptavidin-coated 96 well plates (Pierce Chemical). Alternatively, antibodies reactive with Delta3 but which do not interfere with binding of upstream or downstream elements can be derivatized to the wells of the plate, and Delta3 trapped in the wells by antibody conjugation. As above, preparations of a Delta-binding protein and a test compound are incubated in the Delta-presenting wells of the plate, and the amount of complex trapped in the well can be quantitated. Exemplary methods for detecting such complexes, in addition to those described above for the GST-immobilized complexes, include immunodetection of complexes using antibodies reactive with the Delta3 binding element, or which are reactive with Delta3 protein and compete with the binding element; as well as enzyme-linked assays which rely on detecting an enzymatic activity associated with the binding element, either intrinsic or extrinsic activity. In the instance of the latter, the enzyme can be chemically conjugated or provided as a fusion protein with the Delta-BP. To illustrate, the Delta-BP can be chemically cross-linked or genetically fused with horseradish peroxidase, and the amount of polypeptide trapped in the complex can be assessed with a chromogenic substrate of the enzyme, e.g. 3,3'-diamino-benzadine terahydrochloride or 4-chloro-1-napthol. Likewise, a fusion protein comprising the polypeptide and glutathione-S-transferase can be provided, and complex formation quantitated by detecting the GST activity using 1-chloro-2,4-dinitrobenzene (Habig et al (1974) J Biol Chem 249:7130).

For processes which rely on immunodetection for quantitating one of the proteins trapped in the complex, antibodies against the protein, such as anti-Delta3 antibodies, can be used. Alternatively, the protein to be detected in the complex can be "epitope tagged" in the form of a fusion protein which includes, in addition to the Delta3 sequence, a second polypeptide for which antibodies are readily available (e.g. from commercial sources). For instance, the GST fusion proteins described above can also be used for quantification of binding using antibodies against the GST moiety. Other useful epitope tags include myc-epitopes (e.g., see Ellison et al. (1991) J Biol Chem 266:21150–21157) which includes a 10-residue sequence from c-myc, as well as the pFLAG system (International Biotechnologies, Inc.) or the pEZZ-protein A system (Pharamacia, N.J.).

4.7.2. Cell based assays

In addition to cell-free assays, such as described above, the readily available source of Delta3 proteins provided by the present invention also facilitates the generation of cell-based assays for identifying small molecule agonists/antagonists and the like. For example, cells which are sensitive to bFGF/VEGF or matrigel can be caused to overexpress a recombinant Delta3 protein in the presence and absence of a test agent of interest, with the assay scoring for modulation in Delta3 responses by the target cell mediated by the test agent. As with the cell-free assays, agents which produce a statistically significant change in Delta-dependent responses (either inhibition or potentiation) can be identified. In an illustrative embodiment, the expression or activity of a Delta3 is modulated in embryos or cells and the effects of compounds of interest on the readout of interest (such as tissue differentiation, proliferation, tumorigenesis) are measured. For example, the expression of genes which are up- or down-regulated in response to a Delta-dependent signal cascade can be assayed. In preferred embodiments, the regulatory regions of such genes, e.g., the 5' flanking promoter and enhancer regions, are operably linked to a detectable marker (such as luciferase) which encodes a gene product that can be readily detected.

Exemplary cell lines may include endothelial cells such as MVEC's and bovine aortic endothelial cells (BAEC's); as well as generic mammalian cell lines such as HeLa cells and COS cells, e.g., COS-7 (ATCC# CRL-1651). Further, the transgenic animals discussed herein may be used to generate cell lines, containing one or more cell types involved in cardiovascular disease, that can be used as cell culture models for this disorder. While primary cultures derived from the transgenic animals of the invention may be utilized, the generation of continuous cell lines is preferred. For examples of techniques which may be used to derive a continuous cell line from the transgenic animals, see Small et al., 1985, Mol. Cell Biol. 5:642–648.

In one embodiment, a test compound that modifies a Delta3 activity can be identified by incubating a cell having a Delta3 protein with the test compound and measuring signal transduction from the Delta3 protein. Comparison of the signal transduction in the cells incubated with or without the test compound will reveal whether the test compound is a Delta3 therapeutic. Similarly, a test compound that modifies a Delta3 activity can be identified by incubating a cell having a Delta3 ligand with the test compound, e.g., a Delta3 derived compound, and measuring signal transduction from the Delta3 ligand. Comparison of the signal transduction in the cells incubated with or without the test compound will reveal whether the test compound is a Delta3 therapeutic.

In the event that the Delta3 proteins themselves, or in complexes with other proteins, are capable of binding DNA and/or modifying transcription of a gene, a transcriptional based assay could be used, for example, in which a Delta3 responsive regulatory sequence is operably linked to a detectable marker gene, e.g., a luciferase gene. Similarly, Delta3 therapeutics could also be identified by using an assay in which expression of genes that are modulated upon binding of a Delta3 protein to a Delta3 ligand on a cell is monitored. Genes that are responsive to interaction with a Delta3 protein or Delta3 ligand can be identified according to methods known in the art, e.g., differential hybridization or differential display.

In another embodiment, a silicon-based device, called a microphysiometer, can be used to detect and measure the response of cells having a Delta3 protein to test compounds to identify Delta3 therapeutics. This instrument measures the rate at which cells acidify their environment, which is indicative of cellular growth and/or differentiation (McConnel et al. (1992) Science 257:1906).

Monitoring the influence of compounds on cells may be applied not only in basic drug screening, but also in clinical trials. In such clinical trials, the expression of a panel of genes may be used as a "read out" of a particular drug's therapeutic effect.

In yet another aspect of the invention, the subject Delta3 polypeptides can be used to generate a "two hybrid" assay (see, for example, U.S. Pat. No. 5,283,317; Zervos et al. (1993) Cell 72:223–232; Madura et al. (1993) J Biol Chem 268:12046–12054; Bartel et al. (1993) Biotechniques 14:920–924; Iwabuchi et al. (1993) Oncogene 8:1693–1696; and Brent WO94/10300), for isolating coding sequences for other cellular proteins which bind to or interact with Delta3 ("Delta-binding proteins" or "Delta-bp"), such as Notch, and the like.

Briefly, the two hybrid assay relies on reconstituting in vivo a functional transcriptional activator protein from two separate fusion proteins. In particular, the method makes use of chimeric genes which express hybrid proteins. To illustrate, a first hybrid gene comprises the coding sequence for a DNA-binding domain of a transcriptional activator fused in frame to the coding sequence for a Delta3 polypeptide. The second hybrid protein encodes a transcriptional activation domain fused in frame to a sample gene from a cDNA library. If the bait and sample hybrid proteins are able to interact, e.g., form a Delta-dependent complex, they bring into close proximity the two domains of the transcriptional activator. This proximity is sufficient to cause transcription of a reporter gene which is operably linked to a transcriptional regulatory site responsive to the transcriptional activator, and expression of the reporter gene can be detected and used to score for the interaction of the Delta3 and sample proteins. This system can be used to identify compounds which modify, e.g., inhibit the interaction between a Delta3 protein and another protein, by adding 1 test compound to a cell containing the above-described plasmids. The effect of the test compound on the reporter gene expression and then measured to determine the effect of the test compound on the interaction.

In another embodiment, the invention provides arrays for identifying compounds that can induce apoptosis of cells through a Delta3 protein. Apoptotic arrays are known in the act and are described, e.g., in Grimm et al. (1996) Proc. Natl. Acad. Sci. USA 93:10923.

4.8 Transgenic animals

These systems may be used in a variety of applications. For example, the cell- and animal-based model systems may be used to further characterize Delta3 genes and proteins. In addition, such assays may be utilized as part of screening strategies designed to identify compounds which are capable of ameliorating disease symptoms. Thus, the animal- and cell-based models may be used to identify drugs, pharmaceuticals, therapies and interventions which may be effective in treating disease.

4.8.1. Animal-based systems

One aspect of the present invention concerns transgenic animals which are comprised of cells (of that animal) which contain a transgene of the present invention and which preferably (though optionally) express an exogenous Delta3 protein in one or more cells in the animal. A Delta3 transgene can encode the wild-type form of the protein, or can encode homologs thereof, including both alleles of Delta3 genes, agonists and antagonists, as well as antisense constructs. In preferred embodiments, the expression of the transgene is restricted to specific subsets of cells, tissues or developmental stages utilizing, for example, cis-acting sequences that control expression in the desired pattern. In the present invention, such mosaic expression of a Delta3 protein can be essential for many forms of lineage analysis and can additionally provide a means to assess the effects of, for example, lack of Delta3 expression which might grossly alter development in small patches of tissue within an otherwise normal embryo. In a preferred embodiment, the invention provides transgenic mice having an allele of hDelta3 gene which is associated with ACCPN and the mouse can be used, e.g., to determine the effect of this specific hDelta3 allele. Toward this and, tissue-specific regulatory sequences and conditional regulatory sequences can be used to control expression of the transgene in certain spatial patterns. Moreover, temporal patterns of expression can be provided by, for example, conditional recombination systems or prokaryotic transcriptional regulatory sequences.

Genetic techniques which allow for the expression of transgenes can be regulated via site-specific genetic manipulation in vivo are known to those skilled in the art. For instance, genetic systems are available which allow for the regulated expression of a recombinase that catalyzes the genetic recombination a target sequence. As used herein, the phrase "target sequence" refers to a nucleotide sequence that is genetically recombined by a recombinase. The target sequence is flanked by recombinase recognition sequences and is generally either excised or inverted in cells expressing recombinase activity. Recombinase catalyzed recombination events can be designed such that recombination of the target sequence results in either the activation or repression of expression of one of the subject Delta3 proteins. For example, excision of a target sequence which interferes with the expression of a recombinant Delta3 gene, such as one which encodes an antagonistic homolog or an antisense transcript, can be designed to activate expression of that gene. This interference with expression of the protein can result from a variety of mechanisms, such as spatial separation of the Delta3 gene from the promoter element or an internal stop codon. Moreover, the transgene can be made wherein the coding sequence of the gene is flanked by recombinase recognition sequences and is initially transfected into cells in a 3' to 5' orientation with respect to the promoter element. In such an instance, inversion of the target sequence will reorient the subject gene by placing the 5' end of the coding sequence in an orientation with respect to the promoter element which allow for promoter driven transcriptional activation.

The transgenic animals of the present invention all include within a plurality of their cells a transgene of the present invention, which transgene alters the phenotype of the "host cell" with respect to regulation of cell growth, death and/or differentiation. Since it is possible to produce transgenic organisms of the invention utilizing one or more of the transgene constructs described herein, a general description will be given of the production of transgenic organisms by referring generally to exogenous genetic material. This general description can be adapted by those skilled in the art in order to incorporate specific transgene sequences into organisms utilizing the methods and materials described below.

In an illustrative embodiment, either the cre/loxP recombinase system of bacteriophage P1 (Lakso et al. (1992) PNAS 89:6232–6236; Orban et al. (1992) PNAS 89:6861–6865) or the FLP recombinase system of *Saccharomyces cerevisiae* (O'Gorman et al. (1991) Science 251:1351–1355; PCT publication WO 92/15694) can be used to generate in vivo site-specific genetic recombination systems. Cre recombinase catalyzes the site-specific recombination of an intervening target sequence located between loxP sequences. loxp sequences are 34 base pair nucleotide repeat sequences to which the Cre recombinase binds and are required for Cre recombinase mediated genetic recombination. The orientation of loxp sequences determines whether the intervening target sequence is excised or inverted when Cre recombinase is present (Abremski et al. (1984) J. Biol. Chem. 259:1509–1514); catalyzing the excision of the target sequence when the loxp sequences are oriented as direct repeats and catalyzes inversion of the target sequence when loxP sequences are oriented as inverted repeats.

Accordingly, genetic recombination of the target sequence is dependent on expression of the Cre recombinase. Expression of the recombinase can be regulated by promoter elements which are subject to regulatory control, e.g., tissue-specific, developmental stage-specific, inducible or repressible by externally added agents. This regulated control will result in genetic recombination of the target sequence only in cells where recombinase expression is mediated by the promoter element. Thus, the activation expression of a recombinant Delta3 protein can be regulated via control of recombinase expression.

Use of the cre/loxP recombinase system to regulate expression of a recombinant Delta3 protein requires the construction of a transgenic animal containing transgenes encoding both the Cre recombinase and the subject protein. Animals containing both the Cre recombinase and a recombinant Delta3 gene can be provided through the construction of "double" transgenic animals. A convenient method for providing such animals is to mate two transgenic animals each containing a transgene, e.g., a Delta3 gene and recombinase gene.

One advantage derived from initially constructing transgenic animals containing a Delta3 transgene in a recombinase-mediated expressible format derives from the likelihood that the subject protein, whether agonistic or antagonistic, can be deleterious upon expression in the transgenic animal. In such an instance, a founder population, in which the subject transgene is silent in all tissues, can be propagated and maintained. Individuals of this founder population can be crossed with animals expressing the recombinase in, for example, one or more tissues and/or a desired temporal pattern. Thus, the creation of a founder population in which, for example, an antagonistic Delta3 transgene is silent will allow the study of progeny from that founder in which disruption of Delta3 mediated induction in a particular tissue or at certain developmental stages would result in, for example, a lethal phenotype.

Similar conditional transgenes can be provided using prokaryotic promoter sequences which require prokaryotic proteins to be simultaneous expressed in order to facilitate expression of the Delta3 transgene. Exemplary promoters and the corresponding trans-activating prokaryotic proteins are given in U.S. Pat. No. 4,833,080.

Moreover, expression of the conditional transgenes can be induced by gene therapy-like methods wherein a gene encoding the trans-activating protein, e.g. a recombinase or a prokaryotic protein, is delivered to the tissue and caused to be expressed, such as in a cell-type specific manner. By this method, a Delta3 transgene could remain silent into adulthood until "turned on" by the introduction of the trans-activator.

In an exemplary embodiment, the "transgenic non-human animals" of the invention are produced by introducing transgenes into the germline of the non-human animal. Embryonal target cells at various developmental stages can be used to introduce transgenes. Different methods are used depending on the stage of development of the embryonal target cell. The specific line(s) of any animal used to practice this invention are selected for general good health, good embryo yields, good pronuclear visibility in the embryo, and good reproductive fitness. In addition, the haplotype is a significant factor. For example, when transgenic mice are to be produced, strains such as C57BL/6 or FVB lines are often used (Jackson Laboratory, Bar Harbor, Me.). Preferred strains are those with $H-2^b$, $H-2^d$ or $H-2^q$ haplotypes such as C57BL/6 or DBA/1. The line(s) used to practice this invention may themselves be transgenics, and/or may be knockouts (i.e., obtained from animals which have one or more genes partially or completely suppressed).

In one embodiment, the transgene construct is introduced into a single stage embryo. The zygote is the best target for micro-injection. In the mouse, the male pronucleus reaches the size of approximately 20 micrometers in diameter which allows reproducible injection of 1–2 pl of DNA solution. The use of zygotes as a target for gene transfer has a major advantage in that in most cases the injected DNA will be incorporated into the host gene before the first cleavage (Brinster et al. (1985) PNAS 82:4438–4442). As a consequence, all cells of the transgenic animal will carry the incorporated transgene. This will in general also be reflected in the efficient transmission of the transgene to offspring of the founder since 50% of the germ cells will harbor the transgene.

Normally, fertilized embryos are incubated in suitable media until the pronuclei appear. At about this time, the nucleotide sequence comprising the transgene is introduced into the female or male pronucleus as described below. In some species such as mice, the male pronucleus is preferred. It is most preferred that the exogenous genetic material be added to the male DNA complement of the zygote prior to its being processed by the ovum nucleus or the zygote female pronucleus. It is thought that the ovum nucleus or female pronucleus release molecules which affect the male DNA complement, perhaps by replacing the protamines of the male DNA with histones, thereby facilitating the combination of the female and male DNA complements to form the diploid zygote.

Thus, it is preferred that the exogenous genetic material be added to the male complement of DNA or any other complement of DNA prior to its being affected by the female pronucleus. For example, the exogenous genetic material is added to the early male pronucleus, as soon as possible after the formation of the male pronucleus, which is when the male and female pronuclei are well separated and both are located close to the cell membrane. Alternatively, the exogenous genetic material could be added to the nucleus of the sperm after it has been induced to undergo decondensation. Sperm containing the exogenous genetic material can then be added to the ovum or the decondensed sperm could be added to the ovum with the transgene constructs being added as soon as possible thereafter.

Introduction of the transgene nucleotide sequence into the embryo may be accomplished by any means known in the art such as, for example, microinjection, electroporation, or lipofection. Following introduction of the transgene nucleotide sequence into the embryo, the embryo may be incubated in vitro for varying amounts of time, or reimplanted into the surrogate host, or both. In vitro incubation to maturity is within the scope of this invention. One common method in to incubate the embryos in vitro for about 1–7 days, depending on the species, and then reimplant them into the surrogate host.

For the purposes of this invention a zygote is essentially the formation of a diploid cell which is capable of developing into a complete organism. Generally, the zygote will be comprised of an egg containing a nucleus formed, either naturally or artificially, by the fusion of two haploid nuclei from a gamete or gametes. Thus, the gamete nuclei must be ones which are naturally compatible, i.e., ones which result in a viable zygote capable of undergoing differentiation and developing into a functioning organism. Generally, a euploid zygote is preferred. If an aneuploid zygote is obtained, then the number of chromosomes should not vary by more than one with respect to the euploid number of the organism from which either gamete originated.

In addition to similar biological considerations, physical ones also govern the amount (e.g., volume) of exogenous genetic material which can be added to the nucleus of the zygote or to the genetic material which forms a part of the zygote nucleus. If no genetic material is removed, then the amount of exogenous genetic material which can be added is limited by the amount which will be absorbed without being physically disruptive. Generally, the volume of exogenous genetic material inserted will not exceed about 10 picoliters. The physical effects of addition must not be so great as to physically destroy the viability of the zygote. The biological limit of the number and variety of DNA sequences will vary depending upon the particular zygote and functions of the exogenous genetic material and will be readily apparent to one skilled in the art, because the genetic material, including the exogenous genetic material, of the resulting zygote must be biologically capable of initiating and maintaining the differentiation and development of the zygote into a functional organism.

The number of copies of the transgene constructs which are added to the zygote is dependent upon the total amount of exogenous genetic material added and will be the amount which enables the genetic transformation to occur. Theoretically only one copy is required; however, generally, numerous copies are utilized, for example, 1,000–20,000 copies of the transgene construct, in order to insure that one copy is functional. As regards the present invention, there will often be an advantage to having more than one functioning copy of each of the inserted exogenous DNA sequences to enhance the phenotypic expression of the exogenous DNA sequences.

Any technique which allows for the addition of the exogenous genetic material into nucleic genetic material can be utilized so long as it is not destructive to the cell, nuclear membrane or other existing cellular or genetic structures. The exogenous genetic material is preferentially inserted into the nucleic genetic material by microinjection. Microinjection of cells and cellular structures is known and is used in the art.

Reimplantation is accomplished using standard methods. Usually, the surrogate host is anesthetized, and the embryos are inserted into the oviduct. The number of embryos implanted into a particular host will vary by species, but will usually be comparable to the number of off spring the species naturally produces.

Transgenic offspring of the surrogate host may be screened for the presence and/or expression of the transgene by any suitable method. Screening is often accomplished by Southern blot or Northern blot analysis, using a probe that is complementary to at least a portion of the transgene. Western blot analysis using an antibody against the protein encoded by the transgene may be employed as an alternative or additional method for screening for the presence of the transgene product. Typically, DNA is prepared from tail tissue and analyzed by Southern analysis or PCR for the transgene. Alternatively, the tissues or cells believed to express the transgene at the highest levels are tested for the presence and expression of the transgene using Southern analysis or PCR, although any tissues or cell types may be used for this analysis.

Alternative or additional methods for evaluating the presence of the transgene include, without limitation, suitable biochemical assays such as enzyme and/or immunological assays, histological stains for particular marker or enzyme activities, flow cytometric analysis, and the like. Analysis of the blood may also be useful to detect the presence of the transgene product in the blood, as well as to evaluate the effect of the transgene on the levels of various types of blood cells and other blood constituents.

Progeny of the transgenic animals may be obtained by mating the transgenic animal with a suitable partner, or by in vitro fertilization of eggs and/or sperm obtained from the transgenic animal. Where mating with a partner is to be performed, the partner may or may not be transgenic and/or a knockout; where it is transgenic, it may contain the same or a different transgene, or both. Alternatively, the partner may be a parental line. Where in vitro fertilization is used, the fertilized embryo may be implanted into a surrogate host or incubated in vitro, or both. Using either method, the progeny may be evaluated for the presence of the transgene using methods described above, or other appropriate methods.

The transgenic animals produced in accordance with the present invention will include exogenous genetic material. As set out above, the exogenous genetic material will, in certain embodiments, be a DNA sequence which results in the production of a Delta3 protein (either agonistic or antagonistic), and antisense transcript, or a Delta3 mutant. Further, in such embodiments the sequence will be attached to a transcriptional control element, e.g., a promoter, which preferably allows the expression of the transgene product in a specific type of cell.

Retroviral infection can also be used to introduce transgene into a non-human animal. The developing non-human embryo can be cultured in vitro to the blastocyst stage. During this time, the blastomeres can be targets for retroviral infection (Jaenich, R. (1976) PNAS 73:1260–1264). Efficient infection of the blastomeres is obtained by enzymatic treatment to remove the zona pellucida (Manipulating the Mouse Embryo, Hogan eds. (Cold Spring Harbor Laboratory Press, Cold Spring Harbor, 1986). The viral vector system used to introduce the transgene is typically a replication-defective retrovirus carrying the transgene (Jahner et al. (1985) PNAS 82:6927–6931; Van der Putten et al. (1985) PNAS 82:6148–6152). Transfection is easily and efficiently obtained by culturing the blastomeres on a monolayer of virus-producing cells (Van der Putten, supra; Stewart et al. (1987) EMBO J. 6:383–388). Alternatively, infection can be performed at a later stage. Virus or virus-producing cells can be injected into the blastocoele (Jahner et al. (1982) Nature 298:623–628). Most of the founders will be mosaic for the transgene since incorporation occurs only in a subset of the cells which formed the transgenic non-human animal. Further, the founder may contain various retroviral insertions of the transgene at different positions in the genome which generally will segregate in the offspring. In addition, it is also possible to introduce transgenes into the germ line by intrauterine retroviral infection of the midgestation embryo (Jahner et al. (1982) supra).

A third type of target cell for transgene introduction is the embryonal stem cell (ES). ES cells are obtained from pre-implantation embryos cultured in vitro and fused with embryos (Evans et al. (1981) Nature 292:154–156; Bradley et al. (1984) Nature 309:255–258; Gossler et al. (1986) PNAS 83: 9065–9069; and Robertson et al. (1986) Nature 322:445–448). Transgenes can be efficiently introduced into the ES cells by DNA transfection or by retrovirus-mediated transduction. Such transformed ES cells can thereafter be combined with blastocysts from a non-human animal. The ES cells thereafter colonize the embryo and contribute to the germ line of the resulting chimeric animal. For review see Jaenisch, R. (1988) Science 240:1468–1474.

In one embodiment, gene targeting, which is a method of using homologous recombination to modify an animal's genome, can be used to introduce changes into cultured embryonic stem cells. By targeting a Delta3 gene of interest in ES cells, these changes can be introduced into the germlines of animals to generate chimeras. The gene targeting procedure is accomplished by introducing into tissue culture cells a DNA targeting construct that includes a segment homologous to a target Delta3 locus, and which also includes an intended sequence modification to the Delta3 genomic sequence (e.g., insertion, deletion, point mutation). The treated cells are then screened for accurate targeting to identify and isolate those which have been properly targeted.

Gene targeting in embryonic stem cells is in fact a scheme contemplated by the present invention as a means for disrupting a Delta3 gene function through the use of a targeting transgene construct designed to undergo homologous recombination with one or more Delta3 genomic sequences. The targeting construct can be arranged so that, upon recombination with an element of a Delta3 gene, a positive selection marker is inserted into (or replaces) coding sequences of the targeted Delta3 gene. The inserted sequence functionally disrupts the Delta3 gene, while also providing a positive selection trait. Exemplary Delta3 targeting constructs are described in more detail below.

Generally, the embryonic stem cells (ES cells) used to produce the knockout animals will be of the same species as the knockout animal to be generated. Thus for example, mouse embryonic stem cells will usually be used for generation of knockout mice.

Embryonic stem cells are generated and maintained using methods well known to the skilled artisan such as those described by Doetschman et al. (1985) J. Embryol. Exp. Morphol. 87:27–45). Any line of ES cells can be used, however, the line chosen is typically selected for the ability of the cells to integrate into and become part of the germ line of a developing embryo so as to create germ line transmission of the knockout construct. Thus, any ES cell line that is believed to have this capability is suitable for use herein. One mouse strain that is typically used for production of ES cells, is the 129J strain. Another ES cell line is murine cell line D3 (American Type Culture Collection, catalog no. CKL 1934) Still another preferred ES cell line is the WW6 cell line (Ioffe et al. (1995) PNAS 92:7357–7361). The cells are cultured and prepared for knockout construct insertion using methods well known to the skilled artisan, such as those set forth by Robertson in: Teratocarcinomas and Embryonic Stem Cells: A Practical Approach, E. J. Robertson, ed. IRL Press, Washington, D.C. [1987]); by Bradley et al. (1986) Current Topics in Devel. Biol. 20:357–371); and by Hogan et al. (Manipulating the Mouse Embryo: A Laboratory Manual, Cold Spring Harbor Laboratory Press, Cold Spring Harbor, N.Y. [1986]).

Insertion of the knockout construct into the ES cells can be accomplished using a variety of methods well known in the art including for example, electroporation, microinjection, and calcium phosphate treatment. A preferred method of insertion is electroporation.

Each knockout construct to be inserted into the cell must first be in the linear form. Therefore, if the knockout construct has been inserted into a vector (described infra), linearization is accomplished by digesting the DNA with a suitable restriction endonuclease selected to cut only within the vector sequence and not within the knockout construct sequence.

For insertion, the knockout construct is added to the ES cells under appropriate conditions for the insertion method chosen, as is known to the skilled artisan. Where more than one construct is to be introduced into the ES cell, each knockout construct can be introduced simultaneously or one at a time.

If the ES cells are to be electroporated, the ES cells and knockout construct DNA are exposed to an electric pulse using an electroporation machine and following the manufacturer's guidelines for use. After electroporation, the ES cells are typically allowed to recover under suitable incubation conditions. The cells are then screened for the presence of the knockout construct.

Screening can be accomplished using a variety of methods. Where the marker gene is an antibiotic resistance gene, for example, the ES cells may be cultured in the presence of an otherwise lethal concentration of antibiotic. Those ES cells that survive have presumably integrated the knockout construct. If the marker gene is other than an antibiotic resistance gene, a Southern blot of the ES cell genomic DNA can be probed with a sequence of DNA designed to hybridize only to the marker sequence Alternatively, PCR can be used. Finally, if the marker gene is a gene that encodes an enzyme whose activity can be detected (e.g., b-galactosidase), the enzyme substrate can be added to the cells under suitable conditions, and the enzymatic activity can be analyzed. One skilled in the art will be familiar with other useful markers and the means for detecting their presence in a given cell. All such markers are contemplated as being included within the scope of the teaching of this invention.

The knockout construct may integrate into several locations in the ES cell genome, and may integrate into a different location in each ES cell's genome due to the occurrence of random insertion events. The desired location of insertion is in a complementary position to the DNA sequence to be knocked out, e.g., the Delta3 coding sequence, transcriptional regulatory sequence, etc. Typically, less than about 1–5% of the ES cells that take up the knockout construct will actually integrate the knockout construct in the desired location. To identify those ES cells with proper integration of the knockout construct, total DNA can be extracted from the ES cells using standard methods. The DNA can then be probed on a Southern blot with a probe or probes designed to hybridize in a specific pattern to genomic DNA digested with particular restriction enzyme (s). Alternatively, or additionally, the genomic DNA can be amplified by PCR with probes specifically designed to amplify DNA fragments of a particular size and sequence (i.e., only those cells containing the knockout construct in the proper position will generate DNA fragments of the proper size).

After suitable ES cells containing the knockout construct in the proper location have been identified, the cells can be inserted into an embryo. Insertion may be accomplished in a variety of ways known to the skilled artisan, however a preferred method is by microinjection. For microinjection, about 10–30 cells are collected into a micropipet and injected into embryos that are at the proper stage of development to permit integration of the foreign ES cell containing the knockout construct into the developing embryo. For instance, as the appended Examples describe, the transformed ES cells can be microinjected into blastocytes.

The suitable stage of development for the embryo used for insertion of ES cells is very species dependent, however for mice it is about 3.5 days. The embryos are obtained by perfusing the uterus of pregnant females. Suitable methods for accomplishing this are known to the skilled artisan, and are set forth by, e.g., Bradley et al. (supra).

While any embryo of the right stage of development is suitable for use, preferred embryos are male. In mice, the preferred embryos also have genes coding for a coat color that is different from the coat color encoded by the ES cell genes. In this way, the offspring can be screened easily for the presence of the knockout construct by looking for mosaic coat color (indicating that the ES cell was incorporated into the developing embryo). Thus, for example, if the ES cell line carries the genes for white fur, the embryo selected will carry genes for black or brown fur.

After the ES cell has been introduced into the embryo, the embryo may be implanted into the uterus of a pseudopregnant foster mother for gestation. While any foster mother may be used, the foster mother is typically selected for her ability to breed and reproduce well, and for her ability to care for the young. Such foster mothers are typically prepared by mating with vasectomized males of the same species. The stage of the pseudopregnant foster mother is important for successful implantation, and it is species dependent. For mice, this stage is about 2–3 days pseudopregnant.

Offspring that are born to the foster mother may be screened initially for mosaic coat color where the coat color selection strategy (as described above, and in the appended examples) has been employed. In addition, or as an alternative, DNA from tail tissue of the offspring may be screened for the presence of the knockout construct using Southern blots and/or PCR as described above. Offspring that appear to be mosaics may then be crossed to each other, if they are believed to carry the knockout construct in their germ line, in order to generate homozygous knockout animals. Homozygotes may be identified by Southern blotting of equivalent amounts of genomic DNA from mice that are the product of this cross, as well as mice that are known heterozygotes and wild type mice.

Other means of identifying and characterizing the knock-out offspring are available. For example, Northern blots can be used to probe the mRNA for the presence or absence of transcripts encoding either the gene knocked out, the marker gene, or both. In addition, Western blots can be used to assess the level of expression of the Delta3 gene knocked out in various tissues of the offspring by probing the Western blot with an antibody against the particular Delta3 protein, or an antibody against the marker gene product, where this gene is expressed. Finally, in situ analysis (such as fixing the cells and labeling with antibody) and/or FACS (fluorescence activated cell sorting) analysis of various cells from the offspring can be conducted using suitable antibodies to look for the presence or absence of the knockout construct gene product.

Yet other methods of making knock-out or disruption transgenic animals are also generally known. See, for example, Manipulating the Mouse Embryo, (Cold Spring Harbor Laboratory Press, Cold Spring Harbor, N.Y., 1986). Recombinase dependent knockouts can also be generated, e.g. by homologous recombination to insert target sequences, such that tissue specific and/or temporal control of inactivation of a Delta-gene can be controlled by recombinase sequences (described infra).

Animals containing more than one knockout construct and/or more than one transgene expression construct are prepared in any of several ways. The preferred manner of preparation is to generate a series of mammals, each containing one of the desired transgenic phenotypes. Such animals are bred together through a series of crosses, backcrosses and selections, to ultimately generate a single animal containing all desired knockout constructs and/or expression constructs, where the animal is otherwise congenic (genetically identical) to the wild type except for the presence of the knockout construct(s) and/or transgene(s).

The present invention is further illustrated by the following examples which should not be construed as limiting in any way. The contents of all cited references (including literature references, issued patents, published patent applications as cited throughout this application are hereby expressly incorporated by reference. The practice of the present invention will employ, unless otherwise indicated, conventional techniques of cell biology, cell culture, molecular biology, transgenic biology, microbiology, recombinant DNA, and immunology, which are within the skill of the art. Such techniques are explained fully in the literature. See, for example, Molecular Cloning A Laboratory Manual, 2nd Ed., ed. by Sambrook, Fritsch and Maniatis (Cold Spring Harbor Laboratory Press: 1989); DNA Cloning, Volumes I and II (D. N. Glover ed., 1985); Oligonucleotide Synthesis (M. J. Gait ed., 1984); Mullis et al. U.S. Pat. No. 4,683,195; Nucleic Acid Hybridization (B. D. Hames & S. J. Higgins eds. 1984); Transcription And Translation (B. D. Hames & S. J. Higgins eds. 1984); Culture Of Animal Cells (R. I. Freshney, Alan R. Liss, Inc., 1987); Immobilized Cells And Enzymes (IRL Press, 1986); B. Perbal, A Practical Guide To Molecular Cloning (1984); the treatise, Methods In Enzymology (Academic Press, Inc., N.Y.); Gene Transfer Vectors For Mammalian Cells (J. H. Miller and M. P. Calos eds., 1987, Cold Spring Harbor Laboratory); Methods In Enzymology, Vols. 154 and 155 (Wu et al. eds.), Immunochemical Methods In Cell And Molecular Biology (Mayer and Walker, eds., Academic Press, London, 1987); Handbook Of Experimental Immunology, Volumes I–IV (D. M. Weir and C. C. Blackwell, eds., 1986); Manipulating the Mouse Embryo, (Cold Spring Harbor Laboratory Press, Cold Spring Harbor, N.Y., 1986).

5. EXAMPLES 5.1 Isolation of a full length cDNA encoding hDelta3

Human microvascular endothelial ells C catalog #CC2543; Clonetics, San Diego, Calif.) were separated into four samples of cells which were treated as follows. The first sample was untreated. The second sample was treated with human TGF-β1 (hTGF-β1) (10 ng/ml) (Upstate Biotechnology, Lake Placid, N.Y., Catalog No. 01-134). The third sample was treated with bFGF (10 ng/ml)/VEGF (25 ng/ml) (Upstate Biotechnology, Lake Placid, N.Y., Catalog No. 01-134, Catalog Nos. 01-106 and 01-185, respectively). The fourth sample was differentiated on Matrigel (Collaborative Biomedical Products, Becton Dickinson Labware, Bedford, Mass.). Cells were treated as indicated for 24 hours, the 4 samples were pooled, and RNA was extracted from the pooled cells using a QIAGEN RNeasy kit. The resulting cDNA library was subjected to high throughput random sequencing. This allowed identification of a cDNA fragment comprising the following 171 nucleotide long sequence:

```
GCCCAGGCNGACCCTGGTGTGGACTGTGAGCTGGAGCTCAGCGAGTGTGACAGCAACCCCTGT   (SEQ ID NO.21)
CGCANTGGAGGCAGCTGTAAGGACCANGAGGATGGCTACCACTGCCTGTGTCCTCCGGGCTAC
TACGGCNTGCATCGTGAACACNGCACCTCTTAGCTGNGCCGACTC.
```

Comparison of the nucleotide sequence of this partial cDNA with the sequences in GenBank using the BLAST program (Altschul et al. (1990) J. Mol. Biol. 215:403) revealed that the nucleotide sequence encoded a protein fragment having a significant homology to Delta proteins. In fact, the amino acid sequence had significant homology with a chicken Delta1 protein (GenBank Accession No. U26590), a Xenopus Delta1 protein (GenBank Accession No. L42229), a rat Delta1 protein (GenBank Accession No. U78889), a Xenopus Delta2 protein (GenBank Accession No. U70843) as well as Notch proteins.

A full length cDNA of about 3.2 kb was then isolated by screening a human microvascular endothelial cell (HMVEC) cDNA library using the partial cDNA (SEQ ID NO. 21). This nucleic acid was deposited at the American Type Culture Collection (ATCC) on Mar. 5, 1997, and has been assigned ATCC Accession No. 98348. The nucleotide sequence of the cDNA isolated is shown in FIG. 1 and has SEQ ID No. 1.

A nucleic acid sequence comparison of SEQ ID No. 1 against EST sequence databases using the BLAST program (Altschul et al. (1990) J. Mol. Biol. 215:403) indicated that 5 ESTs have a homology to portions of SEQ ID No. 1. These are all located 3' of the nucleotide sequence encoding the transmembrane domain, i.e., downstream of nucleotide 1996 of SEQ ID No. 1. Three of these ESTs (having accession Nos. T33770, T33811, and T07963) have a nucleotide sequence starting at about nucleotide 2044 of SEQ ID No. 1. However, the nucleotide sequence of the three EST is significantly different from the nucleotide sequence of hDelta3 in about the first 50 nucleotides 3' of nucleotide 2044 of SEQ ID No. 1. Two ESTs (having Accession Nos. R32717 and T07962) are located further downstream of the three ESTs.

The nucleic acid having SEQ ID No. 1 encodes a protein of 685 amino acids having SEQ ID No. 2. A comparison of the amino acid sequence of SEQ ID No. 2 with sequences in GenBank using BLASTP (Altschul et al. (1990) J. Mol. Biol. 215:403) reveals that this protein has a certain homology to previously described Delta proteins. FIG. 2 shows an alignment of the human Delta3 protein having SEQ ID No. 2 with the amino acid sequence of mouse Delta1 protein (Accession No. X80903), rat Delta1 protein (Accession No. U78889), chicken Delta1 protein (Accession No. U26590), two Xenopus Delta1 proteins (Accession Nos. L42229 and U70843) and Drosophila Delta1 protein (Accession No. AA142228). The sequence comparison indicates that human Delta3 protein has the general structure of a Delta3 protein.

In particular, human Delta3 protein has a signal peptide corresponding to about amino acid 1 to about amino acid 17 of SEQ ID No. 2, a DSL motif corresponding to the sequence from about amino acid 173 to about amino acid 217, a first EGF-like repeat corresponding to the sequence from about amino acid 222 to about amino acid 250, a second EGF-like repeat corresponding to the sequence from about amino acid 253 to about amino acid 281, a third EGF-like repeat corresponding to the sequence from about amino acid 288 to about amino acid 321, a fourth EGF-like repeat corresponding to the sequence from about amino acid 328 to about amino acid 359, a fifth EGF-like repeat corresponding to the sequence from about amino acid 366 to about amino acid 399, a sixth EGF-like repeat corresponding to the sequence from about amino acid 411 to about amino acid 437, a seventh EGF-like repeat corresponding to the sequence from about amino acid 444 to about amino acid 475, an eight EGF-like repeat corresponding to the sequence from about amino acid 484 to about amino acid 517, a transmembrane domain corresponding to the sequence from about amino acid 530 to about amino acid 553, and a cytoplasmic domain corresponding to the sequence from about amino acid 554 to about amino acid 685 of SEQ ID No. 2.

An amino acid and nucleotide sequence comparison between the members of the Delta1 and Delta3 protein family and human Delta3 on one hand and between the members of the Delta1 family reveals that the homology between the Delta3 family members is stronger than the homology between human Delta3 and any of the Delta1 family members. For example, although hDelta3 is only approximately 58% similar to the Drosophila Delta1 protein; approximately 70% similar to the mouse Delta1 protein; approximately 70% similar to the rat Delta1 protein; approximately 68% similar to the chick Delta1 protein; and approximately 68% similar to the Xenopus Delta1 proteins; the drosophila, mouse, rat, chick and Xenopus Delta1 proteins are very similar to each other (e.g. the mouse and rat are about 96% similar). Published PCT application WO97/01571 discloses a partial nucleotide and amino acid sequence of a protein having significant homology to Delta1 family members, indicating that it is likely to be a human Delta1 protein. The homology between the partial amino acid sequence of human Delta1 and the amino acid sequence of human Delta3 is indicated in Table I and shows that the proteins are encoded by different genes. All these amino acid and nucleotide sequence comparisons indicate that human Delta3 is an additional species of Delta proteins, sharing some sequence and structure homology with the Delta1 proteins.

5.2 Tissue Expression of the hDelta3 gene

This Example describes the tissue distribution of Delta3 protein, as determined by Northern blot hybridization with a 1.6 kb fragment of human Delta3 cDNA corresponding to the extreme 3' end of SEQ ID No. 1.

Northern blot hybridizations with the various RNA samples were performed under standard conditions and washed under stringent conditions, i.e., in 0.2× SSC at 65° C. In each sample, the probe hybridized to a single RNA of about 3.5 kb. The results of hybridization of the probe to various mRNA samples are described below.

Hybridization of a Clontech Fetal Multiple Tissue Northern (MTN) blot (Clontech, LaJolla, Calif.) containing RNA from fetal brain, lung, liver, and kidney indicated the presence of Delta3 RNA in each of these fetal tissues. Expression was significantly higher in fetal lung and kidney than in fetal brain and liver. Hybridization of a Clontech human Multiple Tissue Northern I (MTNI) and Multiple Tissue Northern II (MTNII) blots (Clontech, LaJolla, Calif.) containing RNA from adult heart, brain, placenta, lung, liver, skeletal muscle, kidney, pancreas, spleen, thymus, prostate, testis, ovary, small intestine, mucosal lining of the colon, and peripheral blood leukocytes with the human 1.6 kb Delta3 probe indicated expression in heart, placenta, lung, skeletal muscle, kidney, pancreas, spleen, thymus, prostate, testis, ovary, small intestine and colon. Expression was particularly strong in adult heart, placenta, lung, and skeletal muscle. Expression was also found in adult brain, liver and testis. However, no significant amount of hDelta3 mRNA was detected in adult peripheral blood leukocytes.

Further, Northern blot hybridization of total mRNA from HMVEC cells treated with TGF-β1 at 10 ng/ml for 24 hours, bFGF at 10 ng/mV VEGF at 25 ng/ml for 24 hours, or untreated for 24 hours indicated that Delta3 expression was induced upon induction with bFGF/VEGF. Accordingly, expression of Delta3 is up-regulated in HMV endothelial cells in response to certain growth factors.

Hybridization of a "cancer" Northern blot containing RNA from HL-60, HeLa, K562, MoLT4, Raji, SW480, A549, and G361 cells, revealed that Delta3 is expressed at high levels in the colorectal carcinoma cell line SW480. Thus, Delta3 expression is high in at least certain tumor cells.

Thus, this Example shows that the Delta3 gene is expressed in numerous tissues, but that it is non detectable in certain tissues, e.g., peripheral blood leukocytes and adult heart tissue (at least when using Northern blot hybridization), that it is expressed at relatively high levels in at least some tumor cells, e.g, colon carcinoma cells, and that its expression can be up-regulated in response to some growth factors, e.g, bFGF and VEGF.

5.3 Chromosomal localization of the hDelta3 gene

A Southern blot containing DNA from a panel of a human/hamster monochromosomal somatic cell hybrids was probed with an hDelta1 cDNA probe. The results obtained clearly indicates that the human Delta3 gene resides on chromosome 15.

5.4 Increased expression of hDelta3 in differentiating endothelial cells

This Example shows that the expression of the hDelta3 gene increases in differentiating endothelial cells relative to non differentiating endothelial cells.

HMVEC cells were separated into 5 cultures and treated as follows: (1) cells were induced to quiescence by growth in basal endothelial growth medium (EGM) (Clontech) which contains 10% fetal calf serum (FCS); (2) cells were grown in complete endothelial growth medium (EGM-MV) (Clontech, Catalog No. CC-3 125) which contains 10% FCS and growth factors; (3) cells were stimulated to proliferate by culture in EGM-MV in the presence of bFGF at 10 ng/ml and VEGF at 25 ng/ml; (4) cells were stimulated to proliferate by culture in EGM-MV in the presence of TGF-β1 at 10 ng/ml; and (5) cells were stimulated to differentiate by culture in EGM-MV on Matrigel. After 24 hours of culture, the cells were harvested, the RNA was extracted and submitted to Northern blot analysis. Hybridization was performed with the 1.6 kb hDelta3 probe described above. The results indicate that among the culture conditions tested, quiescent cells express the lowest amount of hDelta3 (at a barely detectable level). Cells which are proliferating express a higher level of hDelta3. Interestingly, the mRNA level of hDelta3 was strongly increased in cells induced to differentiate by plating on Matrigel.

Thus, this Example clearly demonstrates that hDelta3 expression is strongly increased in cells induced to differentiate and also in cells induced to proliferate.

5.5 hDelta3 is located in a chromosomal region associated with ACCPN

The location of hDelta3 on human chromosome 15 was determined using radiation hybrid (RH) mapping.

A sequence tagged site (STS) was generated from the 3' untranslated region of the gene using a forward primer having the nucleotide sequence GTTTACATTGCATCCTG-GAT (SEQ ID NO. 21) and a reverse primer having the nucleotide sequence CTCTTCTGTTCCTCTGGTTG (SEQ ID NO. 22). The STS was used to screen the Genebridge 4 (Gyapay et al. (1996) Human Molecular Genetics 5:339) and the Standford G3 (Stewart et al. (1997) Genome Res. 7:422) radiation hybrid panels. These panels were derived by fusion of irradiated human donor cells with rodent recipient cells (reference) and can be used for positioning STS markers within existing framework maps, ordering markers in the region of interest as well as establishing the distance between markers.

RH mapping was performed by PCR under the following conditions: 25 ng DNA/20 $\mu$l reaction, 0.5 $\mu$M of each primer, 0.2 mM of each nucleotide, 1.5 mM $MgCl_2$, 1× buffer as provided by the manufacturer of the enzyme, 35 cycles at 94° C., 55° C., 72° C. for 30 seconds each.

The results of the RH mapping indicated that hDelta3 maps to 15q12-15 close to framework marker D1 5S 1244 on the Stanford G3 panel and close to framework marker D15S144 on the Genebridge 4 panel with a LOD score>3. Searching of the OMIM database (Online Mendelian Inheritence in Man; http://www.ncbi.nlm.nih.gob/Omim/searchomim.html) indicated that this region has previously been genetically linked to a neurological disorder called Agenesis of the Corpus Callosum with Peripheral Neuropathy (ACCPN) (Casaubon et al. (1996) Am. J. Hum. Genet. 58:28).

5.6 Identification of Delta therapeutics

This Example describes a simple assay for isolating Delta therapeutics, (e.g., agonist or antagonist of a Delta bioactivity), e.g, Delta3 therapeutics. Based at least in part on the results described in the previous Examples, Delta therapeutics can be used for treating various diseases, including neurological diseases, and/or hyper- or hypoproliferative diseases, and diseases or conditions associated with defects in vasculature. In addition, based at least in part on the similarity of amino acid sequence and structure between the various Delta proteins, Delta3 therapeutics can be used to treat diseases or conditions associated with an aberrant Delta3 activity or an aberrant Delta activity other than a Delta3 activity. Similarly, Delta3 therapeutics as well as Delta therapeutics other than Delta3 therapeutics can be used to treat diseases or conditions associated with an aberrant Delta3 activity. The assay set forth below is applicable to Delta proteins other than Delta3 proteins.

A Delta3 therapeutic can be identified by using an in vitro assay, in which the interaction between a Delta3 protein and a Delta3 binding protein, e.g, a Notch protein, is determined in the presence and in the absence of a test compound. A soluble binding fragment of a Delta3 protein can be prepared by expression of the extracellular portion of human Delta3, e.g., about amino acids 1–529 of SEQ ID No. 2, in *E. coli* according to methods known in the art. Alternatively, the Delta3 protein fragment can be about amino acid 173 to about amino acid 517 of SEQ ID NO. 2. Similarly, a Delta3 binding fragment of a Delta3 binding protein (i.e., Delta3 binding partner) can be produced recombinantly. A Delta3 binding protein can be a Notch protein and can be identified, e.g., by determining whether the protein is capable of binding to a Delta3 protein. A nucleic acid encoding a Notch protein can be obtained, e.g, by PCR amplifying a portion of a Notch gene encoding at least an EGF-like domain, using primers having a nucleotide sequence derived from the nucleotide sequence of a Notch gene present in GenBank or disclosed in PCT Application No. PCT/US92/0365 1 or PCT/US93/09338.

Test compounds can then be tested to determine whether they inhibit the interaction between the Delta3 and the Delta3 binding protein by using an ELISA type assay. Accordingly, one of the recombinantly produced Delta3 protein and the Delta3 binding protein, e.g., Notch protein, is attached to a solid phase surface and the other protein is labeled, e.g., such as by tagging the protein with an epitope, for which an antibody is available (e.g., FLAG epitope, available from International Biotechnologies, Inc.). For example, the Delta3 protein can be linked to the wells of a microtiter (96 well) plate by overnight incubation of the protein at a concentration of 10 µg/ml in PBS. After blocking unoccupied sites on the plate with a BSA solution, various amounts of test compounds and the recombinantly produced Delta3 binding protein are added to the wells in a buffer suitable for a specific interaction between the proteins. After an incubation time of several hours, the wells are rinsed with buffer, and the amount of Delta3 binding protein attached to the wells is determined. The amount of bound protein can be determined by incubating the wells with an anti-tag, e.g, anti-myc, antibody, which can then be detected by enzyme immunoassay. The amount of bound protein is then determined by determining the optical density using an ELISA reader. A lower amount of Delta3 binding protein in a well that contained a test compound relative to a well that did not contain a test compound is indicative that the test compound inhibits the interaction between Delta3 and a Delta3 binding protein.

A Delta3 therapeutic can also be identified by using a reporter assay in which the level of expression of a reporter construct under the control of a Delta3 promoter is measured in the presence or absence of a test compound. A Delta3 promoter can be isolated by screening a genomic library with a Delta3 cDNA which preferably contains the 5' end of the cDNA. A portion of the Delta3 promoter, typically from about 50 to about 500 base pairs long is then cloned upstream of a reporter gene, e.g., a luciferase gene, in a plasmid. This reporter construct is then transfected into cells, e.g., neural cells or endothelial cells. Transfected cells are then be distributed into wells of a multiwell plate and various concentrations of test compounds are added to the wells. After several hours incubation, the level of expression of the reporter construct is determined according to methods known in the art. A difference in the level of expression of the reporter construct in transfected cells incubated with the test compound relative to transfected cells incubated without the test compound will indicate that the test compound is capable of modulating the expression of the Delta3 gene and is thus a Delta3 therapeutic.

Deposit of Microorganisms

A nucleic acid encoding a full length human Delta protein is contained in a plasmid which was deposited with the American Type Culture Collection (ATCC) on Mar. 5, 1997 and has been assigned ATCC accession number 98348.

Equivalents

Those skilled in the art will recognize, or be able to ascertain using no more than routine experimentation, many equivalents of the specific embodiments of the invention described herein. Such equivalents are intended to be encompassed by the following claims.

We claim:

1. An isolated nucleic acid molecule comprising a nucleotide sequence which encodes a polypeptide having a biological activity of the polypeptide consisting of the amino acid sequence of SEQ ID NO: 2, wherein the nucleotide sequence hybridizes to the full complement of a nucleic acid molecule consisting of the nucleotide sequence of SEQ ID NO: 1 under conditions of incubation at 45° C. in 6.0× SSC followed by washing in 2.0× SSC at 50° C.

2. An isolated nucleic acid molecule comprising a nucleotide sequence which encodes a polypeptide having a biological activity of the polypeptide consisting of the amino acid sequence of SEQ ID NO: 2, wherein the nucleotide sequence hybridizes to the full complement of a nucleic acid molecule consisting of the nucleotide sequence of SEQ ID NO: 3 under conditions of incubation at 45° C. in 6.0× SSC followed by washing in 2.0× SSC at 50° C.

3. An isolated nucleic acid molecule comprising a nucleotide sequence which encodes a polypeptide comprising the amino acid sequence of SEQ ID NO: 2.

4. An isolated nucleic acid molecule comprising a nucleotide sequence which encodes a polypeptide comprising the amino acid sequence from about amino acid 18 to amino acid 685 of SEQ ID NO: 2.

5. An isolated nucleic acid molecule comprising a nucleotide sequence which encodes a polypeptide comprising the amino acid sequence encoded by the DNA insert of the plasmid deposited with ATCC as Accession Number 98348.

6. An isolated nucleic acid molecule comprising a nucleotide sequence which encodes the mature polypeptide encoded by the DNA insert of the plasmid deposited with ATCC as Accession Number 98348.

7. An isolated nucleic acid molecule comprising the nucleotide sequence of SEQ ID NO: 1 or a full complement thereof.

8. An isolated nucleic acid molecule comprising the nucleotide sequence of SEQ ID NO: 3 or a full complement thereof.

9. An isolated nucleic acid molecule comprising the nucleotide sequence of the DNA insert of the plasmid deposited with ATCC as Accession Number 98348, or a full complement thereof.

10. An isolated nucleic acid molecule comprising a nucleotide sequence encoding a polypeptide consisting of the amino acid sequence of SEQ ID NO: 2, or a full complement thereof.

11. An isolated nucleic acid molecule comprising a nucleotide sequence encoding a polypeptide consisting of the amino acid sequence from about amino acid 18 to amino acid 685 of SEQ ID NO: 2, or the full complement thereof.

12. An isolated nucleic acid molecule comprising a nucleotide sequence encoding a polypeptide consisting of the amino acid sequence encoded by the DNA insert of the plasmid deposited with ATCC as Accession Number 98348, or the full complement thereof.

13. An isolated nucleic acid molecule comprising a nucleotide sequence encoding a polypeptide consisting of an amino acid sequence of the mature polypeptide encoded by the DNA insert of the plasmid deposited with ATCC as Accession Number 98348, or the full complement thereof.

14. An isolated nucleic acid molecule consisting of the nucleotide sequence of SEQ ID NO: 1 or the full complement thereof.

15. An isolated nucleic acid molecule consisting of the nucleotide sequence of SEQ ID NO: 3 or the full complement thereof.

16. An isolated nucleic acid molecule consisting of the nucleotide sequence of the DNA insert of the plasmid deposited with ATCC as Accession Number 98348 or the full complement thereof.

17. The nucleic acid molecule of any of claims 1–6 or 7–16, which further comprises vector nucleic acid sequences.

18. A host cell which contains the isolated nucleic acid molecule of claim 17.

19. A host cell which contains the isolated nucleic acid molecule as in any of claims 1–16.

20. The host cell of claim 18 which is a mammalian host cell.

21. The host cell of claim 19 which is a mammalian host cell.

* * * * *

SEQUENCE LISTING (1) GENERAL INFORMATION:

(iii) NUMBER OF SEQUENCES: 23

(2) INFORMATION FOR SEQ ID NO:1:

(i) SEQUENCE CHARACTERISTICS:
      (A) LENGTH: 2800 base pairs
      (B) TYPE: nucleic acid
      (C) STRANDEDNESS: single
      (D) TOPOLOGY: linear (ii) MOLECULE TYPE: cDNA (ix) FEATURE:
      (A) NAME/KEY: CDS
      (B) LOCATION: 338..2392

(xi) SEQUENCE DESCRIPTION: SEQ ID NO:1:

```
GTCGACCCAC GCGTCCGGCT GCGCGCAGGC CGGGAACACG AGGCCAAGAG CCGCAGCCCC      60

AGCCGCCTTG GTGCAGCGTA CACCGGCACT AGCCCGCTTG CAGCCCCAGG ATTAGACAGA    120

AGACGCGTCC TCGGCGCGGT CGCCGCCCAG CCGTAGTCAC CTGGATTACC TACAGCGGCA    180

GCTGCAGCGG AGCCAGCGAG AAGGCCAAAG GGGAGCAGCG TCCCGAGAGG AGCGCCTCTT    240
```

```
                                                      -continued

TTCAGGGACC CCGCCGGCTG GCGGACGCGC GGGAAAGCGG CGTCGCGAAC AGAGCCAGAT           300

TGAGGGCCCG CGGGTGGAGA GAGCGACGCC CGAGGGG ATG GCG GCA GCG TCC CGG           355
                                        Met Ala Ala Ala Ser Arg
                                         1               5

AGC GCC TCT GGC TGG GCG CTA CTG CTG CTG GTG GCA CTT TGG CAG CAG           403
Ser Ala Ser Gly Trp Ala Leu Leu Leu Leu Val Ala Leu Trp Gln Gln
            10              15                  20

CGC GCG GCC GGC TCC GGC GTC TTC CAG CTG CAG CTG CAG GAG TTC ATC           451
Arg Ala Ala Gly Ser Gly Val Phe Gln Leu Gln Leu Gln Glu Phe Ile
        25              30              35

AAC GAG CGC GGC GTA CTG GCC AGT GGG CGG CCT TGC GAG CCC GGC TGC           499
Asn Glu Arg Gly Val Leu Ala Ser Gly Arg Pro Cys Glu Pro Gly Cys
    40              45              50

CGG ACT TTC TTC CGC GTC TGC CTT AAG CAC TTC CAG GCG GTC GTC TCG           547
Arg Thr Phe Phe Arg Val Cys Leu Lys His Phe Gln Ala Val Val Ser
55              60              65                  70

CCC GGA CCC TGC ACC TTC GGG ACC GTC TCC ACG CCG GTA TTG GGC ACC           595
Pro Gly Pro Cys Thr Phe Gly Thr Val Ser Thr Pro Val Leu Gly Thr
            75              80              85

AAC TCC TTC GCT GTC CGG GAC GAC AGT AGC GGC GGG GGG CGC AAC CCT           643
Asn Ser Phe Ala Val Arg Asp Asp Ser Ser Gly Gly Gly Arg Asn Pro
        90              95              100

CTC CAA CTG CCC TTC AAT TTC ACC TGG CCG GGT ACC TTC TCG CTC ATC           691
Leu Gln Leu Pro Phe Asn Phe Thr Trp Pro Gly Thr Phe Ser Leu Ile
    105             110             115

ATC GAA GCT TGG CAC GCG CCA GGA GAC GAC CTG CGG CCA GAG GCC TTG           739
Ile Glu Ala Trp His Ala Pro Gly Asp Asp Leu Arg Pro Glu Ala Leu
120             125             130

CCA CCA GAT GCA CTC ATC AGC AAG ATC GCC ATC CAG GGC TCC CTA GCT           787
Pro Pro Asp Ala Leu Ile Ser Lys Ile Ala Ile Gln Gly Ser Leu Ala
135             140             145             150

GTG GGT CAG AAC TGG TTA TTG GAT GAG CAA ACC AGC ACC CTC ACA AGG           835
Val Gly Gln Asn Trp Leu Leu Asp Glu Gln Thr Ser Thr Leu Thr Arg
            155             160             165

CTG CGC TAC TCT TAC CGG GTC ATC TGC AGT GAC AAC TAC TAT GGA GAC           883
Leu Arg Tyr Ser Tyr Arg Val Ile Cys Ser Asp Asn Tyr Tyr Gly Asp
        170             175             180

AAC TGC TCC CGC CTG TGC AAG AAG CGC AAT GAC CAC TTC GGC CAC TAT           931
Asn Cys Ser Arg Leu Cys Lys Lys Arg Asn Asp His Phe Gly His Tyr
    185             190             195

GTG TGC CAG CCA GAT GGC AAC TTG TCC TGC CTG CCC GGT TGG ACT GGG           979
Val Cys Gln Pro Asp Gly Asn Leu Ser Cys Leu Pro Gly Trp Thr Gly
200             205             210

GAA TAT TGC CAA CAG CCT ATC TGT CTT TCG GGC TGT CAT GAA CAG AAT          1027
Glu Tyr Cys Gln Gln Pro Ile Cys Leu Ser Gly Cys His Glu Gln Asn
215             220             225             230

GGC TAC TGC AGC AAG CCA GCA GAG TGC CTC TGC CGC CCA GGC TGG CAG          1075
Gly Tyr Cys Ser Lys Pro Ala Glu Cys Leu Cys Arg Pro Gly Trp Gln
            235             240             245

GGC CGG CTG TGT AAC GAA TGC ATC CCC CAC AAT GGC TGT CGC CAC GGC          1123
Gly Arg Leu Cys Asn Glu Cys Ile Pro His Asn Gly Cys Arg His Gly
        250             255             260

ACC TGC AGC ACT CCC TGG CAA TGT ACT TGT GAT GAG GGC TGG GGA GGC          1171
Thr Cys Ser Thr Pro Trp Gln Cys Thr Cys Asp Glu Gly Trp Gly Gly
    265             270             275

CTG TTT TGT GAC CAA GAT CTC AAC TAC TGC ACC CAC CAC TCC CCA TGC          1219
Leu Phe Cys Asp Gln Asp Leu Asn Tyr Cys Thr His His Ser Pro Cys
280             285             290

AAG AAT GGG GCA ACG TGC TCC AAC AGT GGG CAG CGA AGC TAC ACC TGC          1267
```

```
                                                          -continued

Lys Asn Gly Ala Thr Cys Ser Asn Ser Gly Gln Arg Ser Tyr Thr Cys
295                 300                 305                 310

ACC TGT CGC CCA GGC TAC ACT GGT GTG GAC TGT GAG CTG GAG CTC AGC      1315
Thr Cys Arg Pro Gly Tyr Thr Gly Val Asp Cys Glu Leu Glu Leu Ser
                315                 320                 325

GAG TGT GAC AGC AAC CCC TGT CGC AAT GGA GGC AGC TGT AAG GAC CAG      1363
Glu Cys Asp Ser Asn Pro Cys Arg Asn Gly Gly Ser Cys Lys Asp Gln
                330                 335                 340

GAG GAT GGC TAC CAC TGC CTG TGT CCT CCG GGC TAC TAT GGC CTG CAT      1411
Glu Asp Gly Tyr His Cys Leu Cys Pro Pro Gly Tyr Tyr Gly Leu His
                345                 350                 355

TGT GAA CAC AGC ACC TTG AGC TGC GCC GAC TCC CCC TGC TTC AAT GGG      1459
Cys Glu His Ser Thr Leu Ser Cys Ala Asp Ser Pro Cys Phe Asn Gly
360                 365                 370

GGC TCC TGC CGG GAG CGC AAC CAG GGG GCC AAC TAT GCT TGT GAA TGT      1507
Gly Ser Cys Arg Glu Arg Asn Gln Gly Ala Asn Tyr Ala Cys Glu Cys
375                 380                 385                 390

CCC CCC AAC TTC ACC GGC TCC AAC TGC GAG AAG AAA GTG GAC AGG TGC      1555
Pro Pro Asn Phe Thr Gly Ser Asn Cys Glu Lys Lys Val Asp Arg Cys
                395                 400                 405

ACC AGC AAC CCC TGT GCC AAC GGG GGA CAG TGC CTG AAC CGA GGT CCA      1603
Thr Ser Asn Pro Cys Ala Asn Gly Gly Gln Cys Leu Asn Arg Gly Pro
                410                 415                 420

AGC CGC ATG TGC CGC TGC CGT CCT GGA TTC ACG GGC ACC TAC TGT GAA      1651
Ser Arg Met Cys Arg Cys Arg Pro Gly Phe Thr Gly Thr Tyr Cys Glu
                425                 430                 435

CTC CAC GTC AGC GAC TGT GCC CGT AAC CCT TGC GCC CAC GGT GGC ACT      1699
Leu His Val Ser Asp Cys Ala Arg Asn Pro Cys Ala His Gly Gly Thr
                440                 445                 450

TGC CAT GAC CTG GAG AAT GGG CTC ATG TGC ACC TGC CCT GCC GGC TTC      1747
Cys His Asp Leu Glu Asn Gly Leu Met Cys Thr Cys Pro Ala Gly Phe
455                 460                 465                 470

TCT GGC CGA CGC TGT GAG GTG CGG ACA TCC ATC GAT GCC TGT GCC TCG      1795
Ser Gly Arg Arg Cys Glu Val Arg Thr Ser Ile Asp Ala Cys Ala Ser
                475                 480                 485

AGT CCC TGC TTC AAC AGG GCC ACC TGC TAC ACC GAC CTC TCC ACA GAC      1843
Ser Pro Cys Phe Asn Arg Ala Thr Cys Tyr Thr Asp Leu Ser Thr Asp
                490                 495                 500

ACC TTT GTG TGC AAC TGC CCT TAT GGC TTT GTG GGC AGC CGC TGC GAG      1891
Thr Phe Val Cys Asn Cys Pro Tyr Gly Phe Val Gly Ser Arg Cys Glu
                505                 510                 515

TTC CCC GTG GGC TTG CCG CCC AGC TTC CCC TGG GTG GCC GTC TCG CTG      1939
Phe Pro Val Gly Leu Pro Pro Ser Phe Pro Trp Val Ala Val Ser Leu
                520                 525                 530

GGT GTG GGG CTG GCA GTG CTG CTG GTA CTG CTG GGC ATG GTG GCA GTG      1987
Gly Val Gly Leu Ala Val Leu Leu Val Leu Leu Gly Met Val Ala Val
535                 540                 545                 550

GCT GTG CGG CAG CTG CGG CTT CGA CGG CCG GAC GAC GGC AGC AGG GAA      2035
Ala Val Arg Gln Leu Arg Leu Arg Arg Pro Asp Asp Gly Ser Arg Glu
                555                 560                 565

GCC ATG AAC AAC TTG TCG GAC TTC CAG AAG GAC AAC CTG ATT CCT GCC      2083
Ala Met Asn Asn Leu Ser Asp Phe Gln Lys Asp Asn Leu Ile Pro Ala
                570                 575                 580

GCC CAG CTT AAA AAC ACA AAC CAG AAG AAG GAG CTG GAA GTG GAC TGT      2131
Ala Gln Leu Lys Asn Thr Asn Gln Lys Lys Glu Leu Glu Val Asp Cys
                585                 590                 595

GGC CTG GAC AAG TCC AAC TGT GGC AAA CAG CAA AAC CAC ACA TTG GAC      2179
Gly Leu Asp Lys Ser Asn Cys Gly Lys Gln Gln Asn His Thr Leu Asp
                600                 605                 610
```

-continued

```
TAT AAT CTG GCC CCA GGG CCC CTG GGG CGG GGG ACC ATG CCA GGA AAG      2227
Tyr Asn Leu Ala Pro Gly Pro Leu Gly Arg Gly Thr Met Pro Gly Lys
615                 620                 625                 630

TTT CCC CAC AGT GAC AAG AGC TTA GGA GAG AAG GCG CCA CTG CGG TTA      2275
Phe Pro His Ser Asp Lys Ser Leu Gly Glu Lys Ala Pro Leu Arg Leu
                635                 640                 645

CAC AGT GAA AAG CCA GAG TGT CGG ATA TCA GCG ATG TGC TCC CCC AGG      2323
His Ser Glu Lys Pro Glu Cys Arg Ile Ser Ala Met Cys Ser Pro Arg
            650                 655                 660

GAC TCC ATG TAC CAG TCT GTG TGT TTG ATA TCA GAG GAG AGG AAT GAA      2371
Asp Ser Met Tyr Gln Ser Val Cys Leu Ile Ser Glu Glu Arg Asn Glu
        665                 670                 675

TGT GTC ATT GCC ACG GAG GTA TAAGGCAGGA GCCTACCTGG ACATCCCTGC         2422
Cys Val Ile Ala Thr Glu Val
    680                 685

TCAGCCCCGC GGCTGGACCT TCCTTCTGCA TTGTTTACAT TGCATCCTGG ATGGGACGTT    2482

TTTCATATGC AACGTGCTGC TCTCAGGAGG AGGAGGGAAT GGCAGGAACC GGACAGACTG    2542

TGAACTTGCC AAGAGATGCA ATACCCTTCC ACACCTTTGG GTGTCTGTCT GGCATCAGAT    2602

TGGCAGCTGC ACCAACCAGA GGAACAGAAG AGAAGAGAGT GGCAGTAGCC CCATGGGGCC    2662

CGGAGCTGCT GTGGCCTCCA CTGGCATCCG TGTTTCCAAA AGTGCCTTTG GCCCAGCCAA    2722

GGGTGCCAGG CCTAACTGGG GCACTCAGGG CAGTGTGTTG GAAATTCCAC TGAGGGGAA     2782

ATCAGGTGCT GCGGCCGC                                                  2800
```

(2) INFORMATION FOR SEQ ID NO:2:

(i) SEQUENCE CHARACTERISTICS:
        (A) LENGTH: 685 amino acids
        (B) TYPE: amino acid
        (D) TOPOLOGY: linear (ii) MOLECULE TYPE: protein (xi) SEQUENCE DESCRIPTION: SEQ ID NO:2:

```
Met Ala Ala Ser Arg Ser Ala Ser Gly Trp Ala Leu Leu Leu
1               5                   10                  15

Val Ala Leu Trp Gln Gln Arg Ala Ala Gly Ser Gly Val Phe Gln Leu
                20                  25                  30

Gln Leu Gln Glu Phe Ile Asn Glu Arg Gly Val Leu Ala Ser Gly Arg
            35                  40                  45

Pro Cys Glu Pro Gly Cys Arg Thr Phe Arg Val Cys Leu Lys His
        50                  55                  60

Phe Gln Ala Val Val Ser Pro Gly Pro Cys Thr Phe Gly Thr Val Ser
65                  70                  75                  80

Thr Pro Val Leu Gly Thr Asn Ser Phe Ala Val Arg Asp Asp Ser Ser
                85                  90                  95

Gly Gly Gly Arg Asn Pro Leu Gln Leu Pro Phe Asn Phe Thr Trp Pro
            100                 105                 110

Gly Thr Phe Ser Leu Ile Ile Glu Ala Trp His Ala Pro Gly Asp Asp
        115                 120                 125

Leu Arg Pro Glu Ala Leu Pro Pro Asp Ala Leu Ile Ser Lys Ile Ala
    130                 135                 140

Ile Gln Gly Ser Leu Ala Val Gly Gln Asn Trp Leu Leu Asp Glu Gln
145                 150                 155                 160

Thr Ser Thr Leu Thr Arg Leu Arg Tyr Ser Tyr Arg Val Ile Cys Ser
                165                 170                 175
```

-continued

```
Asp Asn Tyr Tyr Gly Asp Asn Cys Ser Arg Leu Cys Lys Lys Arg Asn
            180                 185                 190

Asp His Phe Gly His Tyr Val Cys Gln Pro Asp Gly Asn Leu Ser Cys
            195                 200                 205

Leu Pro Gly Trp Thr Gly Glu Tyr Cys Gln Gln Pro Ile Cys Leu Ser
            210                 215                 220

Gly Cys His Glu Gln Asn Gly Tyr Cys Ser Lys Pro Ala Glu Cys Leu
225                 230                 235                 240

Cys Arg Pro Gly Trp Gln Gly Arg Leu Cys Asn Glu Cys Ile Pro His
                245                 250                 255

Asn Gly Cys Arg His Gly Thr Cys Ser Thr Pro Trp Gln Cys Thr Cys
            260                 265                 270

Asp Glu Gly Trp Gly Gly Leu Phe Cys Asp Gln Asp Leu Asn Tyr Cys
            275                 280                 285

Thr His His Ser Pro Cys Lys Asn Gly Ala Thr Cys Ser Asn Ser Gly
            290                 295                 300

Gln Arg Ser Tyr Thr Cys Thr Cys Arg Pro Gly Tyr Thr Gly Val Asp
305                 310                 315                 320

Cys Glu Leu Glu Leu Ser Glu Cys Asp Ser Asn Pro Cys Arg Asn Gly
                325                 330                 335

Gly Ser Cys Lys Asp Gln Glu Asp Gly Tyr His Cys Leu Cys Pro Pro
            340                 345                 350

Gly Tyr Tyr Gly Leu His Cys Glu His Ser Thr Leu Ser Cys Ala Asp
            355                 360                 365

Ser Pro Cys Phe Asn Gly Gly Ser Cys Arg Glu Arg Asn Gln Gly Ala
            370                 375                 380

Asn Tyr Ala Cys Glu Cys Pro Pro Asn Phe Thr Gly Ser Asn Cys Glu
385                 390                 395                 400

Lys Lys Val Asp Arg Cys Thr Ser Asn Pro Cys Ala Asn Gly Gly Gln
                405                 410                 415

Cys Leu Asn Arg Gly Pro Ser Arg Met Cys Arg Cys Arg Pro Gly Phe
            420                 425                 430

Thr Gly Thr Tyr Cys Glu Leu His Val Ser Asp Cys Ala Arg Asn Pro
            435                 440                 445

Cys Ala His Gly Gly Thr Cys His Asp Leu Glu Asn Gly Leu Met Cys
            450                 455                 460

Thr Cys Pro Ala Gly Phe Ser Gly Arg Arg Cys Glu Val Arg Thr Ser
465                 470                 475                 480

Ile Asp Ala Cys Ala Ser Ser Pro Cys Phe Asn Arg Ala Thr Cys Tyr
                485                 490                 495

Thr Asp Leu Ser Thr Asp Thr Phe Val Cys Asn Cys Pro Tyr Gly Phe
            500                 505                 510

Val Gly Ser Arg Cys Glu Phe Pro Val Gly Leu Pro Pro Ser Phe Pro
            515                 520                 525

Trp Val Ala Val Ser Leu Gly Val Gly Leu Ala Val Leu Leu Val Leu
            530                 535                 540

Leu Gly Met Val Ala Val Ala Val Arg Gln Leu Arg Leu Arg Arg Pro
545                 550                 555                 560

Asp Asp Gly Ser Arg Glu Ala Met Asn Asn Leu Ser Asp Phe Gln Lys
                565                 570                 575

Asp Asn Leu Ile Pro Ala Ala Gln Leu Lys Asn Thr Asn Gln Lys Lys
            580                 585                 590

Glu Leu Glu Val Asp Cys Gly Leu Asp Lys Ser Asn Cys Gly Lys Gln
```

```
                 595                 600                 605

Gln Asn His Thr Leu Asp Tyr Asn Leu Ala Pro Gly Pro Leu Gly Arg
        610                 615                 620

Gly Thr Met Pro Gly Lys Phe Pro His Ser Asp Lys Ser Leu Gly Glu
625                 630                 635                 640

Lys Ala Pro Leu Arg Leu His Ser Glu Lys Pro Glu Cys Arg Ile Ser
                645                 650                 655

Ala Met Cys Ser Pro Arg Asp Ser Met Tyr Gln Ser Val Cys Leu Ile
        660                 665                 670

Ser Glu Glu Arg Asn Glu Cys Val Ile Ala Thr Glu Val
            675                 680                 685

(2) INFORMATION FOR SEQ ID NO:3:

(i) SEQUENCE CHARACTERISTICS:
        (A) LENGTH: 2055 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:3:

ATGGCGGCAG CGTCCCGGAG CGCCTCTGGC TGGGCGCTAC TGCTGCTGGT GGCACTTTGG      60

CAGCAGCGCG CGGCCGGCTC CGGCGTCTTC CAGCTGCAGC TGCAGGAGTT CATCAACGAG     120

CGCGGCGTAC TGGCCAGTGG GCGGCCTTGC GAGCCCGGCT GCCGGACTTT CTTCCGCGTC     180

TGCCTTAAGC ACTTCCAGGC GGTCGTCTCG CCCGGACCCT GCACCTTCGG GACCGTCTCC     240

ACGCCGGTAT TGGGCACCAA CTCCTTCGCT GTCCGGACG ACAGTAGCGG CGGGGGGCGC     300

AACCCTCTCC AACTGCCCTT CAATTTCACC TGGCCGGGTA CCTTCTCGCT CATCATCGAA     360

GCTTGGCACG CGCCAGGAGA CGACCTGCGG CCAGAGGCCT GCCACCAGA TGCACTCATC     420

AGCAAGATCG CCATCCAGGG CTCCCTAGCT GTGGGTCAGA ACTGGTTATT GGATGAGCAA     480

ACCAGCACCC TCACAAGGCT GCGCTACTCT TACCGGGTCA TCTGCAGTGA CAACTACTAT     540

GGAGACAACT GCTCCCGCCT GTGCAAGAAG CGCAATGACC ACTTCGGCCA CTATGTGTGC     600

CAGCCAGATG GCAACTTGTC CTGCCTGCCC GGTTGGACTG GGAATATTG CCAACAGCCT     660

ATCTGTCTTT CGGGCTGTCA TGAACAGAAT GGCTACTGCA GCAAGCCAGC AGAGTGCCTC     720

TGCCGCCCAG GCTGGCAGGG CCGGCTGTGT AACGAATGCA TCCCCACAA TGGCTGTCGC     780

CACGGCACCT GCAGCACTCC CTGGCAATGT ACTTGTGATG AGGGCTGGGG AGGCCTGTTT     840

TGTGACCAAG ATCTCAACTA CTGCACCCAC CACTCCCCAT GCAAGAATGG GGCAACGTGC     900

TCCAACAGTG GGCAGCGAAG CTACACCTGC ACCTGTCGCC CAGGCTACAC TGGTGTGGAC     960

TGTGAGCTGG AGCTCAGCGA GTGTGACAGC AACCCCTGTC GCAATGGAGG CAGCTGTAAG    1020

GACCAGGAGG ATGGCTACCA CTGCCTGTGT CCTCCGGGCT ACTATGGCCT GCATTGTGAA    1080

CACAGCACCT TGAGCTGCGC CGACTCCCCC TGCTTCAATG GGGCTCCTG CCGGGAGCGC    1140

AACCAGGGGG CCAACTATGC TTGTGAATGT CCCCCCAACT TCACCGGCTC CAACTGCGAG    1200

AAGAAAGTGG ACAGGTGCAC CAGCAACCCC TGTGCCAACG GGGACAGTG CCTGAACCGA    1260

GGTCCAAGCC GCATGTGCCG CTGCCGTCCT GGATTCACGG GCACCTACTG TGAACTCCAC    1320

GTCAGCGACT GTGCCCGTAA CCCTTGCGCC CACGGTGGCA CTTGCCATGA CCTGGAGAAT    1380

GGGCTCATGT GCACCTGCCC TGCCGGCTTC TCTGGCCGAC GCTGTGAGGT GCGGACATCC    1440

ATCGATGCCT GTGCCTCGAG TCCCTGCTTC AACAGGGCCA CCTGCTACAC CGACCTCTCC    1500
```

```
ACAGACACCT TTGTGTGCAA CTGCCCTTAT GGCTTTGTGG GCAGCCGCTG CGAGTTCCCC    1560

GTGGGCTTGC CGCCCAGCTT CCCCTGGGTG GCCGTCTCGC TGGGTGTGGG GCTGGCAGTG    1620

CTGCTGGTAC TGCTGGGCAT GGTGGCAGTG GCTGTGCGGC AGCTGCGGCT TCGACGGCCG    1680

GACGACGGCA GCAGGGAAGC CATGAACAAC TTGTCGGACT TCCAGAAGGA CAACCTGATT    1740

CCTGCCGCCC AGCTTAAAAA CACAAACCAG AAGAAGGAGC TGGAAGTGGA CTGTGGCCTG    1800

GACAAGTCCA ACTGTGGCAA ACAGCAAAAC CACACATTGG ACTATAATCT GGCCCCAGGG    1860

CCCCTGGGGC GGGGGACCAT GCCAGGAAAG TTTCCCCACA GTGACAAGAG CTTAGGAGAG    1920

AAGGCGCCAC TGCGGTTACA CAGTGAAAAG CCAGAGTGTC GGATATCAGC GATGTGCTCC    1980

CCCAGGGACT CCATGTACCA GTCTGTGTGT TTGATATCAG AGGAGAGGAA TGAATGTGTC    2040

ATTGCCACGG AGGTA                                                    2055
```

(2) INFORMATION FOR SEQ ID NO:4:

(i) SEQUENCE CHARACTERISTICS:
        (A) LENGTH: 720 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:4:

```
Met Gly Arg Arg Ser Ala Leu Ala Leu Ala Val Val Ser Ala Leu Leu
 1               5                  10                  15

Cys Gln Val Trp Ser Ser Gly Val Phe Glu Leu Lys Leu Gln Glu Phe
            20                  25                  30

Val Asn Lys Lys Gly Leu Leu Gly Asn Arg Asn Cys Cys Arg Gly Gly
        35                  40                  45

Ser Gly Pro Pro Cys Ala Cys Arg Thr Phe Phe Arg Val Cys Leu Lys
    50                  55                  60

His Gln Ala Ser Val Ser Pro Glu Pro Pro Cys Thr Tyr Gly Ser Ala
65                  70                  75                  80

Val Thr Pro Val Leu Gly Val Asp Ser Phe Ser Leu Pro Asp Gly Ala
                85                  90                  95

Gly Ile Asp Pro Ala Phe Ser Asn Pro Ile Arg Phe Pro Phe Gly Phe
            100                 105                 110

Thr Trp Pro Gly Thr Phe Ser Leu Ile Ile Glu Ala Leu His Thr Asp
        115                 120                 125

Ser Pro Asp Asp Leu Ala Thr Glu Asn Pro Glu Arg Leu Ile Ser Arg
    130                 135                 140

Leu Thr Thr Gln Arg His Thr Val Gly Glu Glu Trp Ser Gln Asp Leu
145                 150                 155                 160

His Ser Ser Gly Arg Thr Asp Leu Arg Tyr Ser Tyr Arg Phe Val Cys
                165                 170                 175

Asp Glu His Tyr Tyr Gly Glu Gly Cys Ser Val Phe Cys Arg Pro Arg
            180                 185                 190

Asp Asp Ala Phe Gly His Phe Thr Cys Gly Asp Arg Gly Glu Lys Met
        195                 200                 205

Cys Asp Pro Gly Trp Lys Gly Gln Tyr Cys Thr Asp Pro Ile Cys Leu
    210                 215                 220

Pro Gly Cys Asp Asp Gln His Gly Tyr Cys Asp Lys Pro Gly Glu Cys
225                 230                 235                 240
```

-continued

```
Lys Cys Arg Val Gly Trp Gln Gly Arg Tyr Cys Asp Glu Cys Ile Arg
                245                 250                 255

Tyr Pro Gly Cys Leu His Gly Thr Cys Gln Gln Pro Trp Gln Cys Asn
            260                 265                 270

Cys Gln Glu Gly Trp Gly Gly Leu Phe Cys Asn Gln Asp Leu Asn Tyr
        275                 280                 285

Cys Thr His His Lys Pro Cys Arg Asn Gly Ala Thr Cys Thr Asn Thr
    290                 295                 300

Gly Gln Gly Ser Tyr Thr Cys Ser Cys Arg Pro Gly Tyr Thr Gly Ala
305                 310                 315                 320

Asn Cys Glu Leu Glu Val Asp Glu Cys Ala Pro Ser Pro Cys Lys Asn
                325                 330                 335

Gly Ala Ser Cys Thr Asp Leu Glu Asp Ser Phe Ser Cys Thr Cys Pro
            340                 345                 350

Pro Gly Phe Tyr Gly Lys Val Cys Glu Leu Ser Ala Met Thr Cys Ala
        355                 360                 365

Asp Gly Pro Cys Phe Asn Gly Arg Cys Ser Asp Asn Pro Asp Gly
    370                 375                 380

Gly Tyr Thr Cys His Cys Pro Leu Gly Phe Ser Gly Phe Asn Cys Glu
385                 390                 395                 400

Lys Lys Met Asp Leu Cys Gly Ser Ser Pro Cys Ser Asn Gly Ala Lys
                405                 410                 415

Cys Val Asp Leu Gly Asn Ser Tyr Leu Cys Arg Cys Gln Ala Gly Phe
            420                 425                 430

Ser Gly Arg Tyr Cys Glu Asp Asn Val Asp Asp Cys Ala Ser Ser Pro
        435                 440                 445

Cys Ala Asn Gly Gly Thr Cys Arg Asp Ser Val Asn Asp Phe Ser Cys
    450                 455                 460

Thr Cys Pro Pro Gly Tyr Thr Gly Lys Asn Cys Ser Ala Pro Val Ser
465                 470                 475                 480

Arg Cys Glu His Ala Pro Cys His Asn Gly Ala Thr Cys His Gln Arg
                485                 490                 495

Gly Gln Arg Tyr Met Cys Glu Cys Ala Gln Gly Tyr Gly Gly Pro Asn
            500                 505                 510

Cys Gln Phe Leu Leu Pro Glu Pro Pro Pro Gly Pro Met Val Val Asp
        515                 520                 525

Leu Ser Glu Arg His Met Glu Ser Gln Gly Gly Pro Phe Pro Trp Val
    530                 535                 540

Ala Val Cys Ala Gly Val Val Leu Val Leu Leu Leu Leu Leu Gly Cys
545                 550                 555                 560

Ala Ala Val Val Val Cys Val Arg Leu Lys Leu Gln Lys His Gln Pro
                565                 570                 575

Pro Pro Glu Pro Cys Gly Gly Glu Thr Glu Thr Met Asn Asn Leu Ala
            580                 585                 590

Asn Cys Gln Arg Glu Lys Asp Val Ser Val Ser Ile Ile Gly Ala Thr
        595                 600                 605

Gln Ile Lys Asn Thr Asn Lys Lys Ala Asp Phe His Gly Asp His Gly
    610                 615                 620

Ala Lys Lys Ser Ser Phe Lys Val Arg Tyr Pro Thr Val Asp Tyr Asn
625                 630                 635                 640

Leu Val Arg Asp Leu Lys Gly Asp Glu Ala Thr Val Arg Asp Thr His
                645                 650                 655

Ser Lys Arg Asp Thr Lys Cys Gln Ser Gln Ser Ser Ala Gly Glu Glu
```

```
                660                 665                 670
Lys Ile Ala Pro Thr Leu Arg Gly Gly Glu Ile Pro Asp Arg Lys Arg
            675                 680                 685
Pro Glu Ser Val Tyr Ser Thr Ser Lys Asp Thr Lys Tyr Gln Ser Val
        690                 695                 700
Tyr Val Leu Ser Ala Glu Lys Asp Glu Cys Val Ile Ala Thr Glu Val
705                 710                 715                 720
```

(2) INFORMATION FOR SEQ ID NO:5:

(i) SEQUENCE CHARACTERISTICS:
        (A) LENGTH: 713 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:5:

```
Met Gly Arg Arg Ser Ala Leu Ala Leu Ala Val Val Ser Ala Leu Leu
1               5                   10                  15
Cys Gln Val Trp Ser Ser Gly Val Phe Glu Leu Lys Leu Gln Glu Phe
            20                  25                  30
Val Asn Lys Lys Gly Leu Leu Gly Asn Arg Asn Cys Cys Arg Gly Gly
        35                  40                  45
Ser Gly Pro Pro Cys Ala Cys Arg Thr Phe Phe Arg Val Cys Leu Lys
50                  55                  60
His Tyr Gln Ala Ser Val Ser Pro Glu Pro Pro Cys Thr Tyr Gly Ser
65                  70                  75                  80
Ala Val Thr Ala Val Leu Gly Val Asp Ser Phe Ser Leu Pro Asp Gly
                85                  90                  95
Ala Gly Ile Asp Pro Ala Phe Ser Asn Pro Ile Arg Phe Pro Phe Gly
            100                 105                 110
Phe Thr Trp Pro Gly Thr Phe Ser Leu Ile Ile Glu Ala Leu His Thr
        115                 120                 125
Asp Ser Pro Asp Asp Leu Ala Thr Glu Asn Pro Glu Arg Leu Ile Ser
130                 135                 140
Arg Leu Thr Thr Gln Arg His Thr Val Gly Glu Glu Trp Ser Gln Asp
145                 150                 155                 160
Leu His Ser Ser Gly Arg Thr Asp Leu Arg Tyr Ser Tyr Arg Phe Val
                165                 170                 175
Cys Asp Glu His Tyr Tyr Gly Glu Gly Cys Ser Val Phe Cys Arg Pro
            180                 185                 190
Arg Asp Asp Ala Phe Gly His Phe Thr Cys Gly Glu Arg Gly Glu Lys
        195                 200                 205
Met Cys Asp Pro Gly Trp Lys Gly Gln Tyr Cys Thr Asp Pro Ile Cys
210                 215                 220
Leu Pro Gly Cys Asp Asp Gln His Gly Tyr Cys Asp Lys Pro Gly Glu
225                 230                 235                 240
Cys Lys Cys Arg Val Gly Trp Gln Gly Arg Tyr Cys Asp Glu Cys Ile
                245                 250                 255
Arg Tyr Pro Gly Cys Leu His Gly Thr Cys Gln Gln Pro Trp Gln Cys
            260                 265                 270
Asn Cys Gln Glu Gly Trp Gly Gly Leu Phe Cys Asn Gln Asp Leu Asn
        275                 280                 285
Tyr Cys Thr His His Lys Pro Cys Arg Asn Gly Ala Thr Cys Thr Asn
```

```
        290                 295                 300
Thr Gly Gln Gly Ser Tyr Thr Cys Ser Cys Arg Pro Gly Tyr Thr Gly
305                 310                 315                 320
Ala Asn Cys Glu Leu Glu Val Asp Glu Cys Ala Pro Ser Pro Cys Lys
                325                 330                 335
Asn Gly Gly Ser Cys Thr Asp Leu Glu Asp Ser Tyr Ser Cys Thr Cys
                340                 345                 350
Pro Pro Gly Phe Tyr Gly Lys Val Cys Glu Leu Ser Ala Met Thr Cys
            355                 360                 365
Ala Asp Gly Pro Cys Phe Asn Gly Gly Arg Cys Ser Asp Asn Pro Asp
        370                 375                 380
Gly Gly Tyr Thr Cys His Cys Pro Ala Gly Phe Ser Gly Phe Asn Cys
385                 390                 395                 400
Glu Lys Lys Ile Asp Leu Cys Ser Ser Ser Pro Cys Ser Asn Gly Ala
                405                 410                 415
Lys Cys Val Asp Leu Gly Asn Ser Tyr Leu Cys Arg Cys Gln Thr Gly
                420                 425                 430
Phe Ser Gly Arg Tyr Cys Glu Asp Asn Val Asp Cys Ala Ser Ser
            435                 440                 445
Pro Cys Ala Asn Gly Gly Thr Cys Arg Asp Ser Val Asn Asp Phe Ser
        450                 455                 460
Cys Thr Cys Pro Pro Gly Tyr Thr Gly Lys Asn Cys Ser Ala Pro Val
465                 470                 475                 480
Ser Arg Cys Glu His Ala Pro Cys His Asn Gly Ala Thr Cys His Gln
                485                 490                 495
Arg Gly Gln Arg Tyr Met Cys Glu Cys Ala Gln Gly Tyr Gly Gly Ala
            500                 505                 510
Asn Cys Gln Phe Leu Leu Pro Glu Pro Pro Asp Leu Ile Val Ala
            515                 520                 525
Ala Gln Gly Gly Ser Phe Pro Trp Val Ala Val Cys Ala Gly Val Val
        530                 535                 540
Leu Val Leu Leu Leu Leu Leu Gly Cys Ala Ala Val Val Val Cys Val
545                 550                 555                 560
Arg Leu Lys Leu Gln Lys His Gln Pro Pro Asp Pro Cys Gly Gly
            565                 570                 575
Glu Thr Glu Thr Met Asn Asn Leu Ala Asn Cys Gln Arg Glu Lys Asp
            580                 585                 590
Val Ser Val Ser Ile Ile Gly Ala Thr Gln Ile Lys Asn Thr Asn Lys
        595                 600                 605
Lys Ala Asp Phe His Gly Asp His Gly Ala Asp Lys Ser Ser Phe Lys
610                 615                 620
Ala Arg Tyr Pro Thr Val Asp Tyr Asn Leu Ile Arg Asp Leu Lys Gly
625                 630                 635                 640
Asp Glu Ala Thr Val Arg Asp Ala His Ser Lys Arg Asp Thr Lys Cys
                645                 650                 655
Gln Ser Gln Gly Ser Ala Gly Glu Glu Lys Ser Thr Ser Thr Leu Arg
            660                 665                 670
Gly Gly Glu Val Pro Asp Arg Lys Arg Pro Glu Ser Val Tyr Ser Thr
            675                 680                 685
Ser Lys Asp Thr Lys Tyr Gln Ser Val Tyr Val Leu Ser Ala Glu Lys
        690                 695                 700
Asp Glu Cys Val Ile Ala Thr Glu Val
705                 710
```

(2) INFORMATION FOR SEQ ID NO:6:

(i) SEQUENCE CHARACTERISTICS:
        (A) LENGTH: 157 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:6:

```
Glu Asn Ser Tyr Ser Cys Thr Cys Pro Pro Gly Phe Tyr Gly Lys Ile
 1               5                  10                  15
Cys Glu Leu Ser Ala Met Thr Cys Ala Asp Gly Pro Cys Phe Asn Gly
            20                  25                  30
Gly Arg Cys Ser Asp Ser Pro Asp Gly Gly Tyr Ser Cys Arg Cys Pro
        35                  40                  45
Val Cys Tyr Ser Gly Phe Asn Cys Glu Lys Lys Ile Asp Tyr Cys Ser
 50                  55                  60
Ser Ser Pro Cys Ser Asn Gly Ala Lys Cys Val Asp Leu Gly Asp Ala
 65                  70                  75                  80
Tyr Leu Cys Arg Cys Gln Ala Gly Phe Ser Cys Arg His Cys Asp Asp
                85                  90                  95
Asn Val Asp Asp Cys Ala Ser Ser Pro Cys Ala Asn Gly Gly Thr Cys
            100                 105                 110
Arg Asp Gly Val Asn Asp Phe Ser Cys Thr Cys Pro Pro Gly Tyr Thr
        115                 120                 125
Gly Arg Asn Cys Ser Ala Pro Ala Ser Arg Cys Glu His Ala Pro Cys
130                 135                 140
His Asn Gly Ala Thr Cys His Glu Arg Gly His Arg Tyr
145                 150                 155
```

(2) INFORMATION FOR SEQ ID NO:7:

(i) SEQUENCE CHARACTERISTICS:
        (A) LENGTH: 721 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:7:

```
Met Gly Gln Gln Arg Met Leu Thr Leu Leu Val Leu Ser Ala Val Leu
 1               5                  10                  15
Cys Gln Ile Ser Cys Ser Gly Leu Phe Glu Leu Arg Leu Gln Glu Phe
            20                  25                  30
Val Asn Lys Lys Gly Leu Leu Gly Asn Met Asn Cys Cys Arg Pro Gly
        35                  40                  45
Ser Leu Ala Ser Leu Gln Arg Cys Glu Cys Lys Thr Phe Phe Arg Ile
 50                  55                  60
Cys Leu Lys His Tyr Gln Ser Asn Val Ser Pro Glu Pro Pro Cys Thr
 65                  70                  75                  80
Tyr Gly Gly Ala Val Thr Pro Val Leu Gly Thr Asn Ser Phe Val Val
                85                  90                  95
Pro Glu Ser Ser Asn Ala Asp Pro Thr Phe Ser Asn Pro Ile Arg Phe
            100                 105                 110
Pro Phe Gly Phe Thr Trp Pro Gly Thr Phe Ser Leu Ile Ile Glu Ala
```

-continued

```
            115                 120                 125
Ile His Ala Asp Ser Ala Asp Asp Leu Asn Thr Glu Asn Pro Glu Arg
            130                 135                 140
Leu Ile Ser Arg Leu Ala Thr Gln Arg His Leu Thr Val Gly Glu Gln
145                 150                 155                 160
Trp Ser Gln Asp Leu His Ser Ser Asp Arg Thr Glu Leu Lys Tyr Ser
                        165                 170                 175
Tyr Arg Phe Val Cys Asp Glu Tyr Tyr Gly Glu Gly Cys Ser Asp
                    180                 185                 190
Tyr Cys Arg Pro Arg Asp Asp Ala Phe Gly His Phe Ser Cys Gly Glu
                195                 200                 205
Lys Gly Glu Asn Leu Cys Asn Pro Gly Trp Lys Gly Leu Tyr Cys Thr
            210                 215                 220
Glu Pro Ile Cys Leu Pro Gly Cys Asp Glu His His Gly Tyr Cys Asp
225                 230                 235                 240
Lys Pro Gly Glu Cys Lys Cys Arg Val Gly Trp Gln Gly Arg Tyr Cys
                    245                 250                 255
Asp Glu Cys Ile Arg Tyr Pro Gly Cys Leu His Gly Thr Cys Gln Gln
                260                 265                 270
Pro Trp Gln Cys Asn Cys Gln Glu Gly Trp Gly Gly Leu Phe Cys Asn
            275                 280                 285
Gln Asp Leu Asn Tyr Cys Thr His His Lys Pro Cys Glu Asn Gly Ala
            290                 295                 300
Thr Cys Thr Asn Thr Gly Gln Gly Ser Tyr Thr Cys Ser Cys Arg Pro
305                 310                 315                 320
Gly Tyr Thr Gly Ser Asn Cys Glu Ile Glu Val Asn Glu Cys Asp Ala
                    325                 330                 335
Asn Pro Cys Lys Asn Gly Gly Ser Cys Ser Asp Leu Glu Asn Ser Tyr
                340                 345                 350
Thr Cys Ser Cys Pro Pro Gly Phe Tyr Gly Lys Asn Cys Glu Leu Ser
            355                 360                 365
Ala Met Thr Cys Ala Asp Gly Pro Cys Phe Asn Gly Gly Arg Cys Ala
            370                 375                 380
Asp Asn Pro Asp Gly Gly Tyr Ile Cys Pro Cys Pro Val Gly Tyr Ser
385                 390                 395                 400
Gly Phe Asn Cys Glu Lys Lys Ile Asp Tyr Cys Ser Ser Asn Pro Cys
                    405                 410                 415
Ala Asn Gly Ala Arg Cys Glu Asp Leu Gly Asn Ser Tyr Ile Cys Gln
                420                 425                 430
Cys Gln Glu Gly Phe Ser Gly Arg Asn Cys Asp Asp Asn Leu Asp Asp
            435                 440                 445
Cys Thr Ser Phe Pro Cys Gln Asn Gly Gly Thr Cys Gln Asp Gly Ile
            450                 455                 460
Asn Asp Tyr Ser Cys Thr Cys Pro Pro Gly Tyr Ile Gly Lys Asn Cys
465                 470                 475                 480
Ser Met Pro Ile Thr Lys Cys Glu His Asn Pro Cys His Asn Gly Ala
                    485                 490                 495
Thr Cys His Glu Arg Asn Asn Arg Tyr Val Cys Gln Cys Ala Arg Gly
                500                 505                 510
Tyr Gly Gly Asn Asn Cys Gln Phe Leu Leu Pro Glu Leu Lys Pro Val
            515                 520                 525
Val Val Asp Leu Thr Glu Lys Tyr Thr Glu Gly Gln Ser Gly Gln Phe
            530                 535                 540
```

```
Pro Trp Ile Ala Val Cys Ala Gly Ile Val Leu Val Leu Met Leu Leu
545                 550                 555                 560

Leu Gly Cys Ala Ala Val Val Val Cys Val Arg Val Arg Val Gln Lys
                565                 570                 575

Arg Arg His Gln Pro Glu Ala Cys Arg Gly Glu Ser Lys Thr Met Asn
            580                 585                 590

Asn Leu Ala Asn Cys Gln Arg Glu Lys Asp Ile Ser Val Ser Phe Ile
            595                 600                 605

Gly Thr Thr Gln Ile Lys Asn Thr Asn Lys Lys Ile Asp Phe Leu Ser
        610                 615                 620

Glu Ser Asn Asn Glu Lys Asn Gly Tyr Lys Pro Arg Tyr Pro Ser Val
625                 630                 635                 640

Asp Tyr Asn Leu Val His Glu Leu Lys Asn Glu Asp Ser Pro Lys Glu
                645                 650                 655

Glu Arg Ser Lys Cys Glu Ala Lys Cys Ser Ser Asn Asp Ser Asp Ser
                660                 665                 670

Glu Asp Val Asn Ser Val His Ser Lys Arg Asp Ser Ser Glu Arg Arg
            675                 680                 685

Arg Pro Asp Ser Ala Tyr Ser Thr Ser Lys Asp Thr Lys Tyr Gln Ser
            690                 695                 700

Val Tyr Val Ile Ser Asp Glu Lys Asp Glu Cys Ile Ile Ala Thr Glu
705                 710                 715                 720

Val (2) INFORMATION FOR SEQ ID NO:8:

(i) SEQUENCE CHARACTERISTICS:
        (A) LENGTH: 729 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:8:

Met Gly Gly Arg Phe Leu Leu Thr Leu Ala Leu Leu Ser Ala Leu Leu
1               5                   10                  15

Cys Arg Cys Gln Val Asp Gly Ser Gly Val Phe Glu Leu Lys Leu Gln
                20                  25                  30

Glu Phe Val Asn Lys Lys Gly Leu Leu Ser Asn Arg Asn Cys Cys Arg
            35                  40                  45

Gly Gly Gly Pro Gly Gly Ala Gly Gln Gln Cys Asp Cys Lys Thr
        50                  55                  60

Phe Phe Arg Val Cys Leu Lys His Tyr Gln Ala Ser Val Ser Pro Glu
65                  70                  75                  80

Pro Pro Cys Thr Tyr Gly Ser Ala Ile Thr Pro Val Leu Gly Ala Asn
                85                  90                  95

Ser Phe Ser Val Pro Asp Gly Ala Gly Gly Ala Asp Pro Ala Phe Ser
                100                 105                 110

Asn Pro Ile Arg Phe Pro Phe Gly Phe Thr Trp Pro Gly Thr Phe Ser
            115                 120                 125

Leu Ile Ile Glu Ala Leu His Thr Asp Ser Pro Asp Asp Leu Thr Thr
130                 135                 140

Glu Asn Pro Glu Arg Leu Ile Ser Arg Leu Ala Thr Gln Arg His Leu
145                 150                 155                 160
```

-continued

Ala Val Gly Glu Glu Trp Ser Gln Asp Leu His Ser Ser Gly Arg Thr
            165                 170                 175

Asp Leu Lys Tyr Ser Tyr Arg Phe Val Cys Asp Glu His Tyr Tyr Gly
            180                 185                 190

Glu Gly Cys Ser Val Phe Cys Arg Pro Arg Asp Asp Arg Phe Gly His
            195                 200                 205

Phe Thr Cys Gly Glu Arg Gly Glu Lys Val Cys Asn Pro Gly Trp Lys
    210                 215                 220

Gly Gln Tyr Cys Thr Glu Pro Ile Cys Leu Pro Gly Cys Asp Glu Gln
225                 230                 235                 240

His Gly Phe Cys Asp Lys Pro Gly Glu Cys Lys Cys Arg Val Gly Trp
            245                 250                 255

Gln Gly Arg Tyr Cys Asp Glu Cys Ile Arg Tyr Pro Gly Cys Leu His
            260                 265                 270

Gly Thr Cys Gln Gln Pro Trp Gln Cys Asn Cys Gln Glu Gly Trp Gly
    275                 280                 285

Gly Leu Phe Cys Asn Gln Asp Leu Asn Tyr Cys Thr His His Lys Pro
    290                 295                 300

Cys Lys Asn Gly Ala Thr Cys Thr Asn Thr Gly Gln Gly Ser Tyr Thr
305                 310                 315                 320

Cys Ser Cys Arg Pro Gly Tyr Thr Gly Ser Ser Cys Glu Ile Glu Ile
            325                 330                 335

Asn Glu Cys Asp Ala Asn Pro Cys Lys Asn Gly Gly Ser Cys Thr Asp
            340                 345                 350

Leu Glu Asn Ser Tyr Ser Cys Thr Cys Pro Pro Gly Phe Tyr Gly Lys
            355                 360                 365

Asn Cys Glu Leu Ser Ala Met Thr Cys Ala Asp Gly Pro Cys Phe Asn
            370                 375                 380

Gly Gly Arg Cys Thr Asp Asn Pro Asp Gly Gly Tyr Ser Cys Arg Cys
385                 390                 395                 400

Pro Leu Gly Tyr Ser Gly Phe Asn Cys Glu Lys Lys Ile Asp Tyr Cys
            405                 410                 415

Ser Ser Ser Pro Cys Ala Asn Gly Ala Gln Ala Cys Val Asp Leu Gly
            420                 425                 430

Asn Ser Tyr Ile Cys Gln Cys Gln Ala Gly Phe Thr Gly Arg His Cys
            435                 440                 445

Asp Asp Asn Val Asp Cys Ala Ser Phe Pro Cys Val Asn Gly Gly
            450                 455                 460

Thr Cys Gln Asp Gly Val Asn Asp Tyr Ser Cys Thr Cys Pro Pro Gly
465                 470                 475                 480

Tyr Asn Gly Lys Asn Cys Ser Thr Pro Val Ser Arg Cys Glu His Asn
            485                 490                 495

Pro Cys His Asn Gly Ala Thr Cys His Glu Arg Ser Asn Arg Tyr Val
            500                 505                 510

Cys Glu Cys Ala Arg Gly Tyr Gly Gly Leu Asn Cys Gln Phe Leu Leu
            515                 520                 525

Pro Glu Pro Pro Gln Gly Pro Val Ile Val Asp Phe Thr Glu Lys Tyr
            530                 535                 540

Thr Glu Gly Gln Asn Ser Gln Phe Pro Trp Ile Ala Val Cys Ala Gly
545                 550                 555                 560

Ile Ile Leu Val Leu Met Leu Leu Gly Cys Ala Ala Ile Val Val
            565                 570                 575

Cys Val Arg Leu Lys Val Gln Lys Arg His His Gln Pro Glu Ala Cys

```
                    580                 585                 590
Arg Ser Glu Thr Glu Thr Met Asn Asn Leu Ala Asn Cys Gln Arg Glu
                595                 600                 605
Lys Asp Ile Ser Ile Ser Val Ile Gly Ala Thr Gln Ile Lys Asn Thr
            610                 615                 620
Asn Lys Lys Val Asp Phe His Ser Asp Asn Ser Asp Lys Asn Gly Tyr
625                 630                 635                 640
Lys Val Arg Tyr Pro Ser Val Asp Tyr Asn Leu Val His Glu Leu Lys
                645                 650                 655
Asn Glu Asp Ser Val Lys Glu His Gly Lys Cys Glu Ala Lys Cys
            660                 665                 670
Glu Thr Tyr Asp Ser Glu Ala Glu Lys Ser Ala Val Gln Leu Lys
            675                 680                 685
Ser Ser Asp Thr Ser Glu Arg Lys Arg Pro Asp Ser Val Tyr Ser Thr
    690                 695                 700
Ser Lys Asp Thr Lys Tyr Gln Ser Val Tyr Val Ile Ser Glu Glu Lys
705                 710                 715                 720
Asp Glu Cys Ile Ile Ala Thr Glu Val
                725

(2) INFORMATION FOR SEQ ID NO:9:

(i) SEQUENCE CHARACTERISTICS:
        (A) LENGTH: 717 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:9:

Met Gly Arg Leu Met Ile Ala Val Leu Leu Cys Val Met Ile Ser Gln
1               5                   10                  15
Gly Phe Cys Ser Gly Val Phe Glu Leu Lys Leu Gln Glu Phe Leu Asn
            20                  25                  30
Lys Lys Gly Val Thr Gly Asn Ala Asn Cys Cys Lys Gly Ser Ala Ala
        35                  40                  45
Glu Gly His Gln Cys Glu Cys Lys Thr Phe Phe Arg Ile Cys Leu Lys
50                  55                  60
His Tyr Gln Ala Asn Val Ser Pro Asp Pro Cys Thr Tyr Gly Gly
65                  70                  75                  80
Ala Val Thr Pro Val Leu Gly Ser Asn Ser Phe Gln Val Pro Glu Ser
                85                  90                  95
Phe Pro Asp Ser Ser Phe Thr Asn Pro Ile Pro Phe Ala Phe Gly Phe
            100                 105                 110
Thr Trp Pro Gly Thr Phe Ser Leu Ile Ile Glu Ala Leu His Thr Asp
            115                 120                 125
Ser Thr Asp Asp Leu Ser Thr Glu Asn Pro Asp Arg Leu Ile Ser Arg
    130                 135                 140
Met Thr Thr Gln Arg His Leu Thr Val Gly Glu Glu Trp Ser Gln Asp
145                 150                 155                 160
Leu Gln Val Gly Gly Arg Thr Glu Leu Lys Tyr Ser Tyr Arg Phe Val
                165                 170                 175
Cys Asp Glu His Tyr Tyr Gly Glu Gly Cys Ser Val Phe Cys Arg Pro
            180                 185                 190
Arg Asp Asp Thr Phe Gly His Phe Thr Cys Gly Glu Arg Gly Glu Ile
```

```
                   195                 200                 205
Ile Cys Asn Ser Gly Trp Lys Gly Gln Tyr Cys Thr Glu Pro Ile Cys
210                 215                 220

Leu Pro Gly Cys Asp Glu Asp His Gly Phe Cys Asp Lys Pro Gly Glu
225                 230                 235                 240

Cys Lys Cys Arg Val Gly Phe Ser Gly Lys Tyr Cys Asp Asp Cys Ile
                245                 250                 255

Arg Tyr Pro Gly Cys Leu His Gly Thr Cys Gln Gln Pro Trp Gln Cys
                260                 265                 270

Asn Cys Gln Glu Gly Trp Gly Gly Leu Phe Cys Asn Gln Asp Leu Asn
                275                 280                 285

Tyr Cys Thr His His Lys Pro Cys Gln Asn Gly Ala Thr Cys Thr Asn
290                 295                 300

Thr Gly Gln Gly Ser Tyr Thr Cys Ser Cys Arg Pro Gly Phe Thr Gly
305                 310                 315                 320

Asp Ser Cys Glu Ile Glu Val Asn Glu Cys Ser Gly Ser Pro Cys Arg
                325                 330                 335

Asn Gly Gly Ser Cys Thr Asp Leu Glu Asn Thr Tyr Ser Cys Thr Cys
                340                 345                 350

Pro Pro Gly Phe Tyr Gly Arg Asn Cys Glu Leu Ser Ala Met Thr Cys
                355                 360                 365

Ala Asp Gly Pro Cys Phe Asn Gly Gly His Cys Ala Asp Asn Pro Glu
370                 375                 380

Gly Gly Tyr Phe Cys Gln Cys Pro Met Gly Tyr Ala Gly Phe Asn Cys
385                 390                 395                 400

Glu Lys Lys Ile Asp His Cys Ser Ser Asn Pro Cys Ser Asn Asp Ala
                405                 410                 415

Gln Cys Leu Asp Leu Val Asp Ser Tyr Leu Cys Gln Cys Pro Glu Gly
                420                 425                 430

Phe Thr Gly Thr His Cys Glu Asp Asn Ile Asp Glu Cys Ala Thr Tyr
                435                 440                 445

Pro Cys Gln Asn Gly Gly Thr Cys Gln Asp Gly Leu Ser Asp Tyr Thr
                450                 455                 460

Cys Thr Cys Pro Pro Gly Tyr Thr Gly Lys Asn Cys Thr Ser Ala Val
465                 470                 475                 480

Asn Lys Cys Leu His Asn Pro Cys His Asn Gly Ala Thr Cys His Glu
                485                 490                 495

Met Asp Asn Arg Tyr Val Cys Ala Cys Ile Pro Gly Tyr Gly Gly Arg
                500                 505                 510

Asn Cys Gln Phe Leu Leu Pro Glu Asn Pro Gln Gly Gln Ala Ile Val
                515                 520                 525

Glu Gly Ala Asp Lys Arg Tyr Ser Tyr Glu Glu Asp Asp Gly Gly Phe
530                 535                 540

Pro Trp Thr Ala Val Cys Ala Gly Ile Ile Leu Val Leu Leu Val Leu
545                 550                 555                 560

Ile Gly Gly Ser Val Phe Val Ile Tyr Ile Arg Leu Lys Leu Gln Gln
                565                 570                 575

Arg Ser Gln Gln Ile Asp Ser His Ser Glu Ile Glu Thr Met Asn Asn
                580                 585                 590

Leu Thr Asn Asn Arg Ser Arg Glu Lys Asp Leu Ser Val Ser Ile Ile
                595                 600                 605

Gly Ala Thr Gln Val Lys Asn Ile Asn Lys Lys Val Asp Phe Gln Ser
610                 615                 620
```

```
Asp Gly Asp Lys Asn Gly Phe Lys Ser Arg Tyr Ser Leu Val Asp Tyr
625                 630                 635                 640

Asn Leu Val His Glu Leu Lys Gln Glu Asp Leu Gly Lys Glu Asp Ser
            645                 650                 655

Glu Arg Ser Glu Ala Thr Lys Cys Glu Pro Leu Asp Ser Asp Ser Glu
        660                 665                 670

Glu Lys His Arg Asn His Leu Lys Ser Asp Ser Glu Arg Lys Arg
    675                 680                 685

Thr Glu Ser Leu Cys Lys Asp Thr Lys Tyr Gln Ser Val Phe Val Leu
    690                 695                 700

Ser Glu Glu Lys Asp Glu Cys Ile Ile Ala Thr Glu Val
705                 710                 715

(2) INFORMATION FOR SEQ ID NO:10:

(i) SEQUENCE CHARACTERISTICS:
         (A) LENGTH: 642 amino acids
         (B) TYPE: amino acid
         (C) STRANDEDNESS:
         (D) TOPOLOGY: linear (ii) MOLECULE TYPE: protein (xi) SEQUENCE DESCRIPTION: SEQ ID NO:10:

Met Ala Ser Pro Leu Leu Val Tyr Val Ala Ala Thr Leu Cys Leu
1               5                   10                  15

Pro Leu Val Tyr Pro Ala Gly Val Phe Glu Leu Lys Ile His Ser Phe
            20                  25                  30

Ser Thr Pro Arg Pro Ala Cys Ala Ala Gly Lys Ser Cys Asn Ile Phe
            35                  40                  45

Phe Arg Val Cys Leu Lys His Ala Gln Pro Val Val Ser Pro Asp Pro
    50                  55                  60

Pro Cys Thr Phe Gly Ser Ala Val Ser Asp Ile Leu Pro Ser Asp Ser
65              70                  75                  80

Lys Ala Ile Thr Asp Ser Ser Pro Ile Arg Val Pro Phe His Phe Lys
                85                  90                  95

Trp Pro Gly Ile Phe Ser Leu Ile Ile Glu Ser Trp Thr Thr Asn Ser
            100                 105                 110

Ala Glu Gln Ser Thr Glu Asn Pro Asp Asn Leu Leu Ser Arg Leu Ala
        115                 120                 125

Thr Arg Arg Arg Leu Ser Ile Gly Glu Asp Trp Ser Gln Asp Ile His
    130                 135                 140

Leu Gly Gln Gln Ser Glu Leu Arg Tyr Ser Tyr His Val Ser Cys Asp
145                 150                 155                 160

Glu His Tyr Tyr Gly Asp Ser Cys Ser Asp Tyr Cys Arg Pro Arg Asp
                165                 170                 175

Asp Asn Phe Gly His Tyr Thr Cys Asp Glu Gln Gly Asn Arg Leu Cys
            180                 185                 190

Met Ser Gly Trp Lys Gly Glu Tyr Cys Ala Glu Pro Ile Cys Leu Pro
        195                 200                 205

Gly Cys Ser Glu Ser His Gly Phe Cys Glu Leu Pro Gly Glu Cys Lys
    210                 215                 220

Cys Arg Met Gly Trp Gln Gly Glu Leu Cys Asp Glu Cys Leu Arg Tyr
225                 230                 235                 240

Pro Gly Cys Gln His Gly Ser Cys Ser Gln Pro Trp Glu Cys Ile Cys
                245                 250                 255
```

```
Gln Glu Gly Trp Gly Gly Leu Phe Cys Asn Gln Asp Leu Asn Tyr Cys
            260                 265                 270

Thr Asn His Gln Pro Cys Arg Asn Gly Ala Ser Cys Ile Asn Ile Gly
        275                 280                 285

Gln Gly Ser Tyr Ser Cys Ser Cys Arg Ala Gly Phe Thr Gly Thr Asn
        290                 295                 300

Cys Glu Ile Asp Ile Asn Glu Cys Ala Ser Asn Pro Cys Lys Asn Gly
305                 310                 315                 320

Gly Ser Cys Asn Asp Leu Glu Asn Asp Tyr Glu Cys Val Cys Pro Arg
            325                 330                 335

Gly Phe Tyr Gly Lys Asn Cys Asp Ile Ser Ala Met Thr Cys Glu Asp
            340                 345                 350

Gly Pro Cys Phe Asn Gly Gly Thr Cys Ile Glu Lys Ser Ser Gly Val
            355                 360                 365

Gly Tyr Val Cys Arg Cys Pro Pro Asn Tyr His Gly Ser Asn Cys Glu
            370                 375                 380

Lys Lys Ile Asp Arg Cys Thr Asn Ser Pro Cys Leu Asn Gly Gly Gln
385                 390                 395                 400

Cys Leu Asp Met Gly Arg Asn Val Leu Cys Lys Cys Arg Pro Gly Pro
            405                 410                 415

Ser Gly Pro Arg Cys Glu Leu Asn Ile Asp Asp Cys Ala Ser Ser Pro
            420                 425                 430

Cys Ala Asn Gly Gly Thr Cys Val Asp Ala Val Asn Ser Tyr Thr Cys
            435                 440                 445

Ser Cys Thr Leu Gly Tyr Gly Gly Lys Asp Cys Thr Leu Arg Val Asp
450                 455                 460

Ala Cys Ser Ser Lys Pro Cys Lys Asn Gly Gly Thr Cys Tyr Thr Lys
465                 470                 475                 480

Phe Thr Gly Asn Val Cys Gln Cys Pro Thr Gly Phe Met Gly Thr Ser
            485                 490                 495

Cys Glu Phe Arg Val His Asp Pro Thr Pro Ala Ser His Arg Ala Asp
            500                 505                 510

Ser Ser Asn Thr Leu Thr Met Val Val Cys Leu Gly Leu Leu Thr Phe
            515                 520                 525

Phe Leu Leu Gly Cys Gly Val Phe Met Val Met Arg Gly Met Arg Arg
            530                 535                 540

Gly His Phe Asn Glu Lys Gly Arg Val Asn Asn Asp Leu Glu Pro Lys
545                 550                 555                 560

Asn Asn Leu Ile Glu Lys Glu Pro His Phe Lys Met Pro Asn Pro Asp
            565                 570                 575

Tyr Leu Arg Glu Lys Ser Ser Lys Gln Lys Leu Leu Gln Gly Ser
            580                 585                 590

Glu Ser Glu Glu Glu Arg Ser Gly Arg Arg Thr Asp Arg Lys Pro Asp
            595                 600                 605

Thr Lys Gln Cys Asn Pro Thr Ser Arg Tyr Pro Glu Asp Gly Ala Tyr
            610                 615                 620

His Pro Ile Tyr Ile Leu Pro Glu Pro Glu Gln Cys Ile Phe Ala Thr
625                 630                 635                 640

Glu Val
```

(2) INFORMATION FOR SEQ ID NO:11:

(i) SEQUENCE CHARACTERISTICS:

(A) LENGTH: 830 amino acids
(B) TYPE: amino acid
(C) STRANDEDNESS:
(D) TOPOLOGY: linear (ii) MOLECULE TYPE: protein (xi) SEQUENCE DESCRIPTION: SEQ ID NO:11:

```
Met His Trp Ile Lys Cys Leu Leu Thr Ala Phe Ile Cys Phe Thr Val
1               5                   10                  15

Ile Val Gln Val His Ser Ser Gly Ser Phe Glu Leu Arg Leu Lys Tyr
                20                  25                  30

Phe Ser Asn Asp His Gly Arg Asp Asn Glu Gly Arg Cys Cys Ser Gly
            35                  40                  45

Glu Ser Asp Gly Ala Thr Gly Lys Cys Leu Gly Ser Cys Lys Thr Arg
    50                  55                  60

Phe Arg Val Cys Leu Lys His Tyr Gln Ala Thr Ile Asp Thr Thr Ser
65                  70                  75                  80

Gln Cys Thr Tyr Gly Asp Val Ile Thr Pro Ile Leu Gly Glu Asn Ser
                85                  90                  95

Val Asn Leu Thr Asp Ala Gln Arg Phe Gln Asn Lys Gly Phe Thr Asn
                100                 105                 110

Pro Ile Gln Phe Pro Phe Ser Phe Ser Trp Pro Gly Thr Phe Ser Leu
            115                 120                 125

Ile Val Glu Ala Trp His Asp Thr Asn Asn Ser Gly Asn Ala Arg Thr
130                 135                 140

Asn Lys Leu Leu Ile Gln Arg Leu Leu Val Gln Gln Val Leu Glu Val
145                 150                 155                 160

Ser Ser Glu Trp Lys Thr Asn Lys Ser Glu Ser Gln Tyr Thr Ser Leu
                165                 170                 175

Glu Tyr Asp Phe Arg Val Thr Cys Asp Leu Asn Tyr Tyr Gly Ser Gly
            180                 185                 190

Cys Ala Lys Phe Cys Arg Pro Arg Asp Asp Ser Phe Gly His Ser Thr
            195                 200                 205

Cys Ser Glu Thr Gly Glu Ile Ile Cys Leu Thr Gly Trp Gln Gly Asp
    210                 215                 220

Tyr Cys His Ile Pro Lys Cys Ala Lys Gly Cys Glu His Gly His Cys
225                 230                 235                 240

Asp Lys Pro Asn Gln Cys Val Cys Gln Leu Gly Trp Lys Gly Ala Leu
                245                 250                 255

Cys Asn Glu Cys Val Leu Glu Pro Asn Cys Ile His Gly Thr Cys Asn
            260                 265                 270

Lys Pro Trp Thr Cys Ile Cys Asn Glu Gly Trp Gly Gly Leu Tyr Cys
        275                 280                 285

Asn Gln Asp Leu Asn Tyr Cys Thr Asn His Arg Pro Cys Lys Asn Gly
    290                 295                 300

Gly Thr Cys Phe Asn Thr Gly Glu Gly Leu Tyr Thr Cys Lys Cys Ala
305                 310                 315                 320

Pro Gly Tyr Ser Gly Asp Asp Glu Asn Glu Ile Tyr Ser Cys Asp Ala
                325                 330                 335

Asp Val Asn Pro Cys Gln Asn Gly Gly Thr Cys Ile Asp Glu Pro His
            340                 345                 350

Thr Lys Thr Gly Lys Cys His Cys Ala Asn Gly Trp Ser Gly Lys Met
        355                 360                 365

Cys Glu Glu Lys Val Leu Thr Cys Ser Asp Lys Pro Cys His Gln Gly
```

-continued

```
          370                 375                 380
Ile Cys Arg Asn Val Arg Pro Gly Leu Gly Ser Lys Gly Gln Gly Tyr
385                 390                 395                 400
Gln Cys Glu Cys Pro Ile Gly Tyr Ser Gly Pro Asn Cys Asp Leu Gln
                405                 410                 415
Leu Asp Asn Cys Ser Pro Asn Pro Cys Ile Asn Gly Gly Ser Cys Gln
                420                 425                 430
Pro Ser Gly Lys Cys Ile Cys Pro Ala Gly Phe Ser Gly Thr Arg Cys
                435                 440                 445
Glu Thr Asn Ile Asp Asp Cys Leu Gly His Gln Cys Glu Asn Gly Gly
                450                 455                 460
Thr Cys Ile Asp Met Val Asn Gln Tyr Arg Cys Gln Cys Val Pro Gly
465                 470                 475                 480
Phe His Gly Thr His Cys Ser Ser Lys Val Asp Leu Cys Leu Ile Arg
                485                 490                 495
Pro Cys Ala Asn Gly Gly Thr Cys Leu Asn Leu Asn Asn Asp Tyr Gln
                500                 505                 510
Cys Thr Cys Arg Ala Gly Phe Thr Gly Lys Asp Cys Ser Val Asp Ile
                515                 520                 525
Asp Glu Cys Ser Ser Gly Pro Cys His Asn Gly Gly Thr Cys Met Asn
                530                 535                 540
Arg Val Asn Ser Phe Glu Cys Val Cys Ala Asn Gly Phe Arg Gly Lys
545                 550                 555                 560
Gln Cys Asp Glu Glu Ser Tyr Asp Ser Val Thr Phe Asp Ala His Gln
                565                 570                 575
Tyr Gly Ala Thr Thr Gln Ala Arg Ala Asp Gly Leu Thr Asn Ala Gln
                580                 585                 590
Val Val Leu Ile Ala Val Phe Ser Val Ala Met Pro Leu Val Ala Val
                595                 600                 605
Ile Ala Ala Cys Val Val Phe Cys Met Lys Arg Lys Arg Lys Arg Ala
                610                 615                 620
Gln Glu Lys Asp Asp Ala Glu Ala Arg Lys Gln Asn Glu Gln Asn Ala
625                 630                 635                 640
Val Ala Thr Met His His Asn Gly Ser Gly Val Gly Val Ala Leu Ala
                645                 650                 655
Ser Ala Ser Leu Gly Gly Lys Thr Gly Ser Asn Ser Gly Leu Thr Phe
                660                 665                 670
Asp Gly Gly Asn Pro Asn Ile Ile Lys Asn Thr Trp Asp Lys Ser Val
                675                 680                 685
Asn Asn Ile Cys Ala Ser Ala Ala Ala Ala Ala Ala Ala Ala Ala Ala
                690                 695                 700
Ala Asp Glu Cys Leu Met Tyr Gly Gly Tyr Val Ala Ser Val Ala Asp
705                 710                 715                 720
Asn Asn Asn Ala Asn Ser Asp Phe Cys Val Ala Pro Leu Gln Arg Ala
                725                 730                 735
Lys Ser Gln Lys Gln Leu Asn Thr Asp Pro Thr Leu Met His Arg Gly
                740                 745                 750
Ser Pro Ala Gly Ser Ser Ala Lys Gly Ala Ser Gly Gly Gly Pro Gly
                755                 760                 765
Ala Ala Glu Gly Lys Arg Ile Ser Val Leu Gly Glu Gly Ser Tyr Cys
                770                 775                 780
Ser Gln Arg Trp Pro Ser Leu Ala Ala Ala Gly Val Ala Gly Ala Cys
785                 790                 795                 800
```

```
Ser Ser Gln Leu Met Ala Ala Ser Ala Ala Gly Thr Asp Gly Thr
            805                 810                 815

Ala Gln Gln Gln Arg Ser Val Val Cys Gly Thr Pro His Met
        820                 825                 830
```

(2) INFORMATION FOR SEQ ID NO:12:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:12:

AGCGCCTCTG GCTGGGCGCT                                      20

(2) INFORMATION FOR SEQ ID NO:13:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:13:

CGGCCAGAGG CCTTGCCACC                                      20

(2) INFORMATION FOR SEQ ID NO:14:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:14:

TTGCGCTCCC GGCTGGAGCC                                      20

(2) INFORMATION FOR SEQ ID NO:15:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:15:

ATGCGGCTTG GACCTCGGTT                                      20

(2) INFORMATION FOR SEQ ID NO:16:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide"

(xi) SEQUENCE DESCRIPTION: SEQ ID NO:16:

TGCCGCCATC CCTCGGGGCG T                                                 21

(2) INFORMATION FOR SEQ ID NO:17:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide"

(xi) SEQUENCE DESCRIPTION: SEQ ID NO:17:

GGACGCTGCC GCCATCCCCT                                                   20

(2) INFORMATION FOR SEQ ID NO:18:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide"

(xi) SEQUENCE DESCRIPTION: SEQ ID NO:18:

GGACGCTGCC GCCATCCCCT CGGGGCGT                                          28

(2) INFORMATION FOR SEQ ID NO:19:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:19:

TCAATCTGGC TCTGTTCGCG                                                   20

(2) INFORMATION FOR SEQ ID NO:20:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:20:

CGCTCTCTCC ACCCGCGGGC CCTCAA                                            26

(2) INFORMATION FOR SEQ ID NO:21:

(i) SEQUENCE CHARACTERISTICS:
        (A) LENGTH: 171 base pairs
        (B) TYPE: nucleic acid
        (C) STRANDEDNESS: single -continued

```
        (D) TOPOLOGY: linear (ii) MOLECULE TYPE: cDNA (xi) SEQUENCE DESCRIPTION: SEQ ID NO:21:

GCCCAGGCNG ACCCTGGTGT GGACTGTGAG CTGGAGCTCA GCGAGTGTGA CAGCAACCCC        60

TGTCGCANTG GAGGCAGCTG TAAGGACCAN GAGGATGGCT ACCACTGCCT GTGTCCTCCG       120

GGCTACTACG GCNTGCATCG TGAACACNGC ACCTCTTAGC TGNGCCGACT C                171

(2) INFORMATION FOR SEQ ID NO:22:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:22:

GTTTACATTG CATCCTGGAT                                                    20

(2) INFORMATION FOR SEQ ID NO:23:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:23:

CTCTTCTGTT CCTCTGGTTG                                                    20
```